(12) United States Patent
Zhang et al.

(10) Patent No.: US 11,225,492 B2
(45) Date of Patent: Jan. 18, 2022

(54) HETEROCYCLES USEFUL AS ANTI-CANCER AGENTS

(71) Applicant: Hangzhou Innogate Pharma Co., Ltd., Zhejiang (CN)

(72) Inventors: Hancheng Zhang, Zhejiang (CN); Shifeng Liu, Zhejiang (CN)

(73) Assignee: Hangzhou Innogate Pharma Co., Ltd., Zhejiang (CN)

( * ) Notice: Subject to any disclaimer, the term of this patent is extended or adjusted under 35 U.S.C. 154(b) by 17 days.

(21) Appl. No.: 16/061,747

(22) PCT Filed: Dec. 13, 2016

(86) PCT No.: PCT/CN2016/109754
§ 371 (c)(1),
(2) Date: Jun. 13, 2018

(87) PCT Pub. No.: WO2017/101763
PCT Pub. Date: Jun. 22, 2017

(65) Prior Publication Data
US 2018/0370991 A1    Dec. 27, 2018

Related U.S. Application Data

(60) Provisional application No. 62/266,634, filed on Dec. 13, 2015.

(51) Int. Cl.
| | |
|---|---|
| *A61K 31/519* | (2006.01) |
| *C07D 487/04* | (2006.01) |
| *C07D 519/00* | (2006.01) |
| *C07D 471/04* | (2006.01) |
| *A61P 35/02* | (2006.01) |
| *C07B 59/00* | (2006.01) |

(52) U.S. Cl.
CPC .......... *C07D 519/00* (2013.01); *A61P 35/02* (2018.01); *C07D 471/04* (2013.01); *C07B 59/002* (2013.01)

(58) Field of Classification Search
CPC .. C07D 471/04; C07D 519/00; C07D 487/04; A61K 31/519; A61P 35/00
USPC ................ 544/279; 514/264.1, 24.1
See application file for complete search history.

(56) References Cited

U.S. PATENT DOCUMENTS 7,208,489 B2 * 4/2007 Barvian ............... A61K 31/519
514/217.06

FOREIGN PATENT DOCUMENTS

| CN | 1433417 | A | 7/2003 |
| CN | 101001857 | A | 7/2007 |
| CN | 105294736 | A | 2/2016 |
| WO | 2014183520 | A1 | 11/2014 |

OTHER PUBLICATIONS

Atzrodt et al. Angew. Chem. Int. Ed. 2007, 46, 7744-7765.*
Wolff Manfred E. "Burger's Medicinal Chemistry, 5ed, Part 1", John Wiley & Sons, 1995, pp. 975-977.*
Banker, G.S. etal, "Modern Pharmaceutices, 3ed.", Marcel Dekker, New York. 1996, pp. 451 and 596.*
Cecil Textbook of Medicine, edited by Bennet, J.C., and Plum F., 20th edition,vol. 1, 1004-1010, 1996.*
Cohen et al., Current Opinion in Chemical Biology, 3,459-465, 1999.*
Dermeret al., Bio/Technology, 1994, 12:320.*
Freshney et al.,Culture of Animal Cells, A Manual of Basic Technique, Alan R. Liss, Inc., 1983, New York, p. 4.*
International Search Report and Written Opinion dated Mar. 14, 2017 in International Application No. PCT/CN2016/109754.
Zhang et al., "The research progress of selective histone deacetylase inihibitors," Chinese Journal of Medicinal Chemistry, vol. 23, No. 4, pp. 321-330 (Aug. 31, 2013) (English Abstract attached).

* cited by examiner

*Primary Examiner* — Douglas M Willis
(74) *Attorney, Agent, or Firm* — Ice Miller LLP

(57) ABSTRACT

The present invention provides compounds of Formula (I), and the pharmaceutically acceptable salts, hydrates, and solvates thereof. It also provides pharmaceutical compositions, preparation and utilities thereof in treating diseases and disorders including cancers.

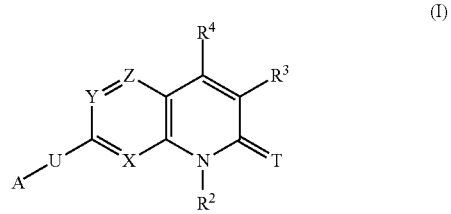

(I)

14 Claims, No Drawings

HETEROCYCLES USEFUL AS ANTI-CANCER AGENTS

CROSS-REFERENCE TO RELATED APPLICATION

This application is a Section 371 of International Application No. PCT/CN2016/109754, filed Dec. 13, 2016, which was published in the English language on Jun. 22, 2017, under International Publication No. WO 2017/101763 A1, which claims priority under 35 U.S.C. § 119(b) to U.S. Provisional Application No. 62/266,634, filed Dec. 13, 2015, the disclosures of which are incorporated herein by reference in their entirety.

BACKGROUND OF THE INVENTION

Cyclin-dependent kinases (CDKs) are protein kinases involved in important cellular processes, such as cell cycle or transcription regulation. There are 13 CDKs and different CDKs responsible for the activation of the cell cycle of quiescent cells, as well as for the progression of the cell cycle from G1 to mitosis. Each of the CDKs controls a specific checkpoint of the cell cycle. CDKs are activated by the binding to the cyclins and thus form specific complexes. In many human cancers, CDKs are overactive or CDK-inhibiting proteins are not functional. Therefore, it is rational to target CDK function to prevent unregulated proliferation of cancer cells (Nature Reviews, 2009, 9, 153-166). For example, CDK4 is the key regulator of the G1-S transition. In complex with Cyclin D, CDK4 phosphorylates Rb and drives cell cycle progression, a process inhibited by p16. The p16-CDK4-cyclin D-Rb is aberrant in the majority of cancers and thus is an attractive target for anti-cancer therapy.

Histone deacetylases (HDACs) are a class of enzymes that remove the acetyl group from the 8-amino groups of lysine residues located in the $NH_2$ terminal tails of core histones. There are 18 known human histone deacetylases, grouped into four classes based on the structure of their accessory domains. Class I includes HDAC1, HDAC2, HDAC3, and HDAC8 and have homology to yeast RPD3. HDAC4, HDAC5, HDAC7, and HDAC9 belong to class II and have homology to yeast HDA1. HDAC6 and HDAC10 contain two catalytic sites and are classified as class IIa, whereas HDAC11 has conserved residues in its catalytic center that are shared by both class I and class II deacetylases and is sometimes placed in class IV. Histone deacetylase inhibitors (HDACIs) are emerging as a new class of potential anticancer agents and have been shown to induce differentiation, cell-cycle arrest, and apoptosis and to inhibit migration, invasion, and angiogenesis in many cancer cell lines. In addition, HDAC inhibitors inhibit tumor growth in animal models and show antitumor activity in patients (Mol. Cancer Res. Oct. 2007, 5; 981).

There is also growing evidence that HDAC inhibitors have potential therapeutic application in nonmalignant diseases, such as for treatment of inflammatory and neurodegenerative diseases.

SUMMARY OF THE INVENTION

The present invention provides, among others, novel heterocyclic compounds and their uses, e.g., as inhibitors for protein kinases (e.g., CDKs) and HDACs.

In one aspect, the present invention provides a compound of Formula (I), its diastereomer or its enantiomer when possible, its deuterium derivative, and/or their corresponding pharmaceutically acceptable salt, prodrug, hydrate, solvate thereof.

A compound of Formula (I) shown below, its deuterium derivatives at any available position of the molecule, its diastereomer and enantiomer (when available):

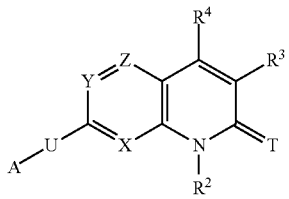

(I)

or their corresponding pharmaceutically acceptable salt, prodrug, hydrate, solvate thereof, wherein:

U is $NR^7$, O, or S;

each of X, Y and Z independently is N or $CR^8$, and each $R^8$ independently is hydrogen, halogen, $C_{1-8}$ alkyl, $C_{2-8}$ alkenyl, $C_{2-8}$ alkynyl, $OR^5$, $SR^5$, $NR^5R^6$, CN, $C(O)R^5$, or $C(O)OR^5$;

T is O;

$R^2$ is hydrogen, $C_{1-8}$ alkyl, $C_{2-8}$ alkenyl, $C_{2-8}$ alkynyl, cycloalkyl, heterocyclyl, aryl, or heteroaryl;

$R^3$ is hydrogen, halogen, $C_{1-8}$ alkyl, $C_{2-8}$ alkenyl, $C_{2-8}$ alkynyl, cycloalkyl, heterocyclyl, aryl, heteroaryl, CN, $NO_2$, $(CR^9R^{10})_mOR^5$, $(CR^9R^{10})_mSR^5$, $(CR^9R^{10})_mNR^5R^6$, $(CR^9R^{10})_mC(O)R^5$, $(CR^9R^{10})_mC(O)OR^5$, $(CR^9R^{10})_mC(O)NR^5R^6$, $(CR^9R^{10})_mOC(O)R^5$, $(CR^9R^{10})_mOC(O)OR^5$, $(CR^9R^{10})_mOC(O)NR^5R^6$, $(CR^9R^{10})_mNR^7C(O)R^5$, $(CR^9R^{10})_mNR^7C(O)OR^5$, $(CR^9R^{10})_mNR^7C(O)NR^5R^6$, $(CR^9R^{10})_mS(O)R^5$, or $(CR^9R^{10})_mS(O)_2R^5$;

m is 0, 1, 2, or 3;

$R^4$ is hydrogen, halogen, $C_{1-8}$ alkyl, $C_{2-8}$ alkenyl, $C_{2-8}$ alkynyl, cycloalkyl, heterocyclyl, aryl, heteroaryl, $OR^5$, $NR^5R^6$, or CN;

each of $R^5$ and $R^6$, independently, is hydrogen, $C_{1-8}$ alkyl, $C_{2-8}$ alkenyl, $C_{2-8}$ alkynyl, cycloalkyl, heterocyclyl, aryl, or heteroaryl;

or, $R^5$ and $R^6$, together with the nitrogen to which they are attached to, form a 3- to 9-membered ring that optionally contains 0-3 additional heteroatoms each independently being N, O, or S;

$R^7$ is hydrogen or $C_{1-4}$ alkyl;

each of $R^9$ and $R^{10}$, independently, is hydrogen or $C_{1-8}$ alkyl; or, $R^9$ and $R^{10}$, together with the carbon to which they are attached to, form a 3- to 9-membered ring that optionally contains 0-3 additional heteroatoms each independently being N, O, or S;

A is of Formula (II), Formula (III), Formula (IV), or Formula (V):

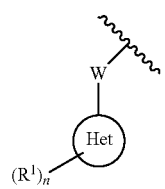

(II)

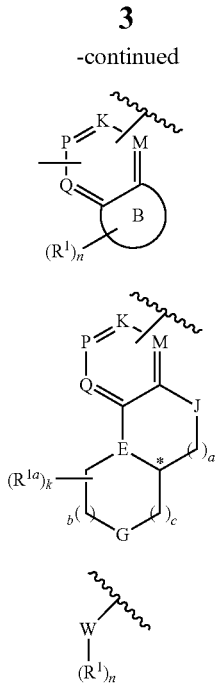

wherein:

" ~~~ " indicates the point of attachment in Formula (II), Formula (III), Formula (IV), or Formula (V) to U in Formula (I);

W is aryl or heteroaryl;

When referring to Formula (II), Het is a 4- to 15-membered mono- or polycyclic heterocycle or a cycloalkyl (wherein the polycyclic heterocycle or a cycloalky comprise bridge ring structure or spiro ring structure) containing 0-5 heteroatoms each independently being N, O, S, S(O), or $S(O)_2$;

n is 0, 1, 2 or 3;

each $R^1$ independently is halogen, $C_{1-8}$ alkyl, $C_{2-8}$ alkenyl, $C_{2-8}$ alkynyl, cycloalkyl, heterocyclyl, aryl, heteroaryl, CN, $OR^5$, $SR^5$, $NR^5R^6$, $C(O)R^5$, $C(O)OR^5$, $C(O)NR^5R^6$, $OC(O)R^5$, $NR^6C(O)R^5$, $S(O)_2R^5$, or $(CH_2)_p$—V—$(CH_2)_qC(O)NH(OH)$; provided that when n is 1, $R^1$ is $(CH_2)_p$—V—$(CH_2)_qC(O)NH(OH)$; or when n is 2 or 3, one $R^1$ is $(CH_2)_p$—V—$(CH_2)_qC(O)NH(OH)$, and the other $R^1$ is selected from groups other than $(CH_2)_p$—V—$(CH_2)_qC(O)NH(OH)$;

or when n is 0, Formula (II) is selected from:

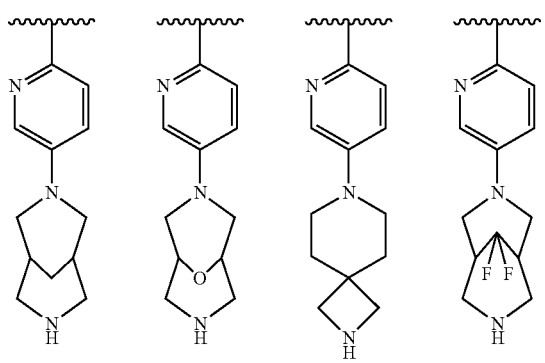

each of p and q independently is 0, 1, 2, 3, 4, 5, 6, 7, 8, 9, or 10;

V is $CH_2$, CH=CH, C≡C, O, S, $NR^{13}$, C(O), OC(O), C(O)O, OC(O)O, C(O)NH, NHC(O), NHC(O)NH, S(O), $S(O)_2$, $S(O)_2NH$, $NHS(O)_2$, $C_{1-8}$ alkyl, cycloalkyl, heterocyclyl, aryl, heteroaryl, $CR^{14}R^{15}$, $V^1CH_2)_tV^2$;

$R^{13}$ is hydrogen, $C_{1-4}$ alkyl, $C(O)R^5$, or $S(O)_2R^5$;

$R^{14}$ and $R^{15}$ independently is hydrogen, halogen, $C_{1-4}$ alkyl, $C_{2-4}$ alkenyl, $C_{2-4}$ alkynyl, cycloalkyl, heterocyclyl, aryl, heteroaryl, CN, $OR^5$, $SR^5$, $NR^5R^6$, $C(O)R^5$, $C(O)OR^5$, $C(O)NR^5R^6$, $OC(O)R^5$, $NR^6C(O)R^5$, $S(O)_2R^5$; or, $R^{14}$ and $R^{15}$, together with the carbon to which they are attached to, form a 3- to 9-membered ring that optionally contains 0-3 heteroatoms each independently being N, O, or S;

$V^1$ and $V^2$ independently CH=CH, C≡C, O, S, $NR^{13}$, C(O)NH, NHC(O), $S(O)_2$, $S(O)_2NH$, $NHS(O)_2$, cycloalkyl, heterocyclyl, aryl, heteroaryl;

t is 0, 1, 2, 3, 4, 5;

Provided that the selection of V, $V^1$, $V^2$, p, q and t meets the requirement of forming a chemically stable structure;

When referring to Formula (III), B is a 5- to 15-membered ring containing 1-5 heteroatoms each independently being N, O, or S;

each of K, M, P, and Q independently is N or $CR^8$;

n and $R^1$ are the same as defined for Formula (II);

When referring to Formula (IV), E is N or $CR^{11}$, wherein $R^{11}$ is hydrogen, $C_{1-4}$ alkyl, or $OR^5$;

J is O, S, $NR^{12}$, $CR^9R^{10}$, C(O), S(O), or $S(O)_2$;

G is $NR^{12}$, O, S, S(O), $S(O)_2$, or $CR^9R^{10}$;

k is 0, 1, 2 or 3;

each $R^{1a}$ independently is hydrogen, halogen, $C_{1-4}$alkyl; or two $R^{1a}$, together with the carbon to which they are attached to, form a carbonyl (=O);

$R^{12}$ is hydrogen, $C_{1-8}$ alkyl, $C_{2-8}$ alkenyl, $C_{2-8}$ alkynyl, cycloalkyl, heterocyclyl, aryl, heteroaryl, $C(O)R^5$, $C(O)OR^5$, $C(O)NR^5R^6$, $S(O)_2R^5$, or $(CH_2)_p$—V—$(CH_2)_qC(O)NH(OH)$;

each of a, b and c, independently, is 0, 1, 2, or 3;

"*" denotes a chiral center;

When referring to Formula (V), W, n, and $R^1$ are the same as defined for Formula (II); and wherein each alkyl, alkenyl, alkynyl, cycloalkyl, heterocyclyl, aryl, or heteroaryl, can be optionally and independently substituted by 1-3 substituents selected from the following group: halogen, $C_{1-8}$ alkyl, $C_{2-8}$ alkenyl, $C_{2-8}$ alkynyl, $C_{3-10}$ cycloalkyl, heterocyclyl, aryl, heteroaryl, CN, $NO_2$, $OR^5$, $SR^5$, $NR^5R^6$, $C(O)R^5$, $C(O)OR^5$, $C(O)NR^5R^6$, or $S(O)_2R^5$.

Unless otherwise indicated, the above mentioned aryl comprises 6-12 carbon atoms; heteroaryl is 5- to 15-membered heteroaryl; cycloalkyl is $C_{3-8}$ cycloalkyl; and heterocyclyl is 3- to 12-membered heterocyclyl;

In another preferred embodiment, $R^2$ is $C_{3-8}$cycloalkyl; $R^3$ is $C(O)C_{1-8}$ alkyl, $R^4$ is $C_{1-8}$ alkyl; X and Y are both N; Z is CH; and U is NH.

In another preferred embodiment, $R^2$ is cyclopentyl; $R^3$ is $C(O)CH_3$, $R^4$ is methyl; X and Y are both N; Z is CH; and U is NH.

In another preferred embodiment, referring to Formula (II), wherein Het is a 4- to 8-membered mono-heterocycle or a 9- to 15-membered bridged or spiro bicyclic ring containing 1-4 heteroatoms each independently being N or O; n is 1; and $R^1$ is $(CH_2)_p$—V—$(CH_2)_q C(O)NH(OH)$.

In another preferred embodiment, W is phenyl or pyridinyl.

In another preferred embodiment, Formula (II) is

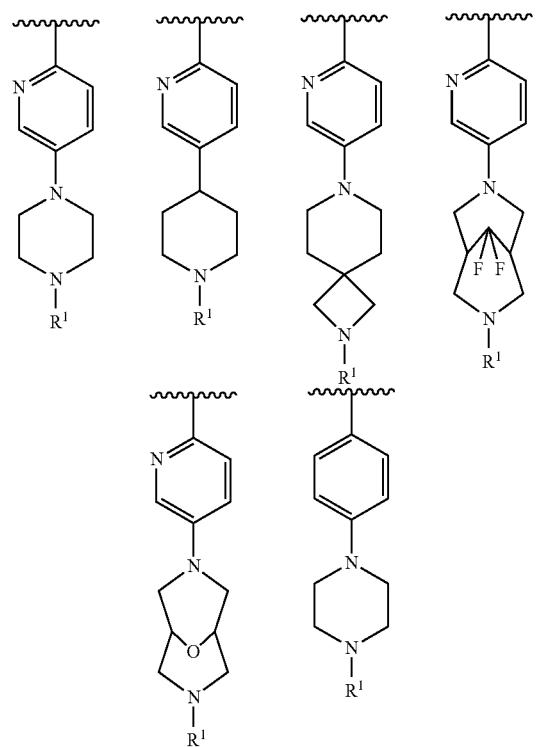

wherein $R^1$ is $(CH_2)_p$—V—$(CH_2)_q C(O)NH(OH)$.

In another preferred embodiment, Formula (II) is

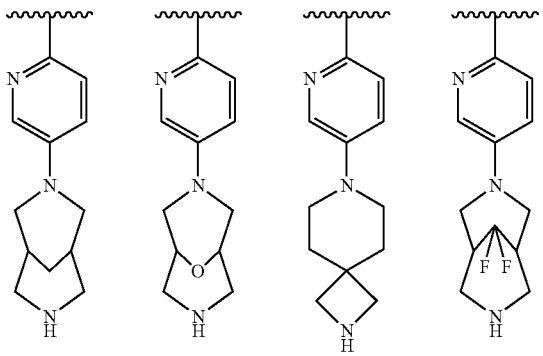

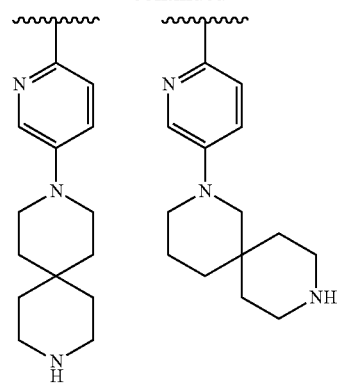

In another preferred embodiment, referring to Formula (III), wherein B is a 5- to 12-membered non-aromatic monocyclic ring containing 1-4 heteroatoms each independently being N or O; n is 1; and $R^1$ is $(CH_2)_p$—V—$(CH_2)_q C(O)NH(OH)$.

In another preferred embodiment, when referring to Formula (III), wherein at most one of K, M, P, and Q is N.

In another preferred embodiment, Formula (III) is

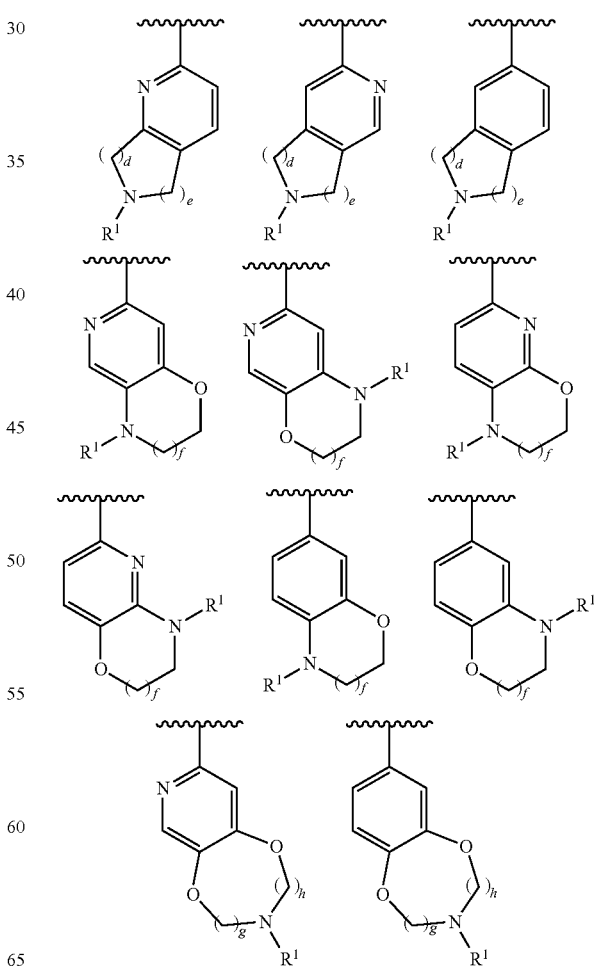

wherein

R¹ is $(CH_2)_p$—V—$(CH_2)_q C(O)NH(OH)$;

each of d and e independently is 0, 1, 2, or 3, provided the sum of d and e is equal to or greater than 2;

each f independently is 1, 2, or 3; and each of g and h independently is 2, 3, or 4.

In another preferred embodiment, when referring to Formula (IV), wherein at most one of K, M, P, and Q is N.

In another preferred embodiment, J is O, NH, $NCH_3$, $NC(O)CH_3$, or $CH_2$; E is N; and G is $NR^{12}$, O, S, S(O), $S(O)_2$, or $CR^9R^{10}$; a, b and c each independently is 1; $R^9$, $R^{10}$ and $R^{12}$ are the same as defined in claim 1.

In another preferred embodiment, J is O; E is N; and G is $NR^{12}$ or O; a, b and c each independently is 1; k is 0, 1, or 2; $R^{1a}$ independently is hydrogen, or two $R^{1a}$, together with the carbon to which they are attached to, form a carbonyl (C=O);

$R^{12}$ is hydrogen, $C_{1-4}$ alkyl, $C_{2-4}$ alkenyl, $C_{2-4}$ alkynyl, cycloalkyl, heterocyclyl, aryl, heteroaryl, $C(O)R^5$, $C(O)OR^5$, $C(O)NR^5R^6$, $S(O)_2R^5$, or $(CH_2)_p$—V—$(CH_2)_q C(O)NH(OH)$.

In another preferred embodiment, Formula (IV) is:

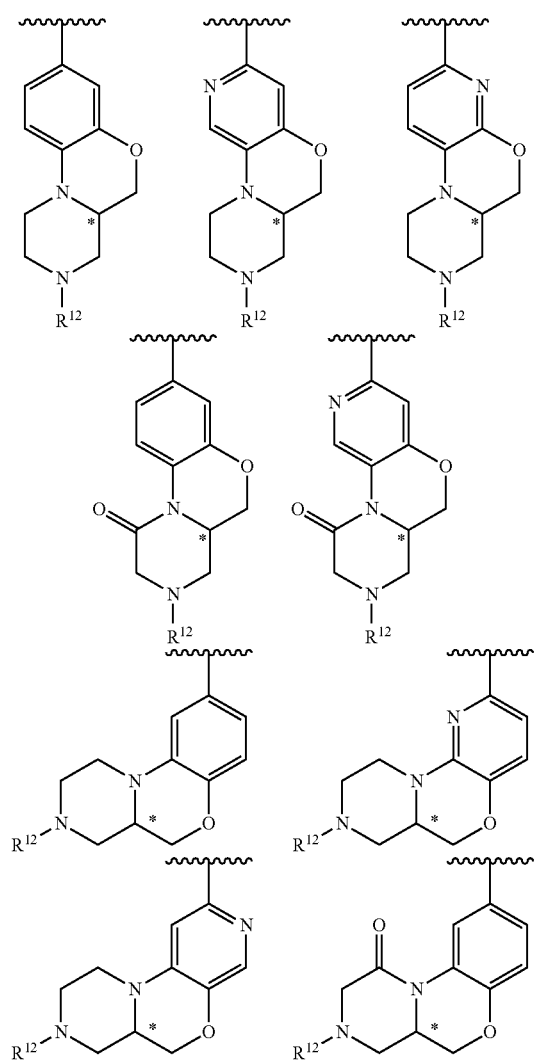

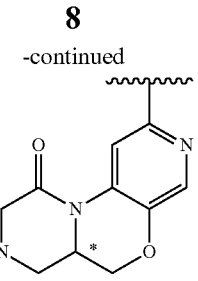

Wherein $R^{12}$ is defined as above.

In another preferred embodiment, W in Formula (V) is phenyl or pyridinyl, n is 1, and R¹ is $(CH_2)_p$—V—$(CH_2)_q C(O)NH(OH)$.

In another preferred embodiment, each of p and q independently is 0, 1, 2, 3, 4, 5, 6, or V is $CH_2$, CH=CH, C≡C, O, $NR^{13}$, C(O), C(O)O, C(O)NH, $S(O)_2$, $S(O)_2NH$, cycloalkyl, heterocyclyl, aryl, heteroaryl, $V^1(CH_2)_tV^2$; wherein $V^1$ and $V^2$ independently CH=CH, O, $NR^{13}$, cycloalkyl, heterocyclyl, aryl, heteroaryl; t is 0, 1, 2, or 3; and $R^{13}$ is hydrogen, $C_{1-4}$ alkyl; Provided that the selection of V, $V^1$, $V^2$, p, q and t meets the requirement of forming a chemically stable structure.

In another preferred embodiment, a compound of Formula (I) is:

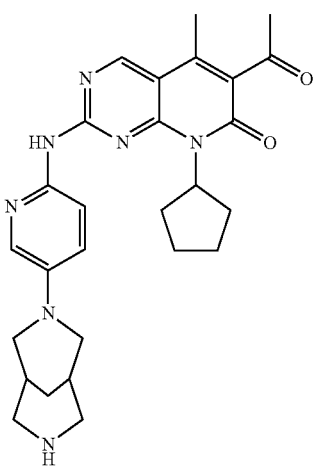

1

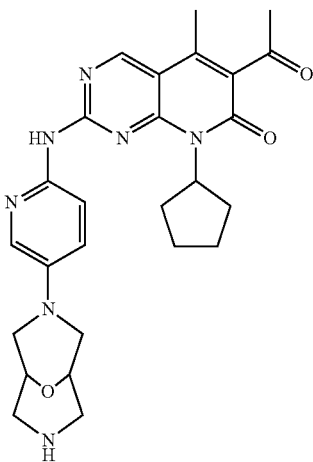

2

3
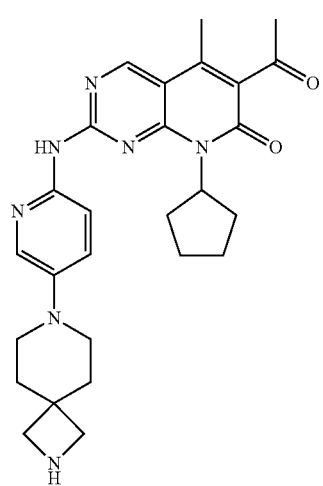
4
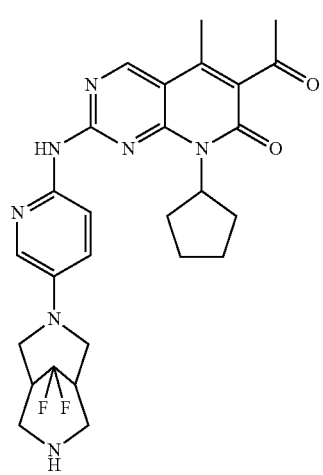
5
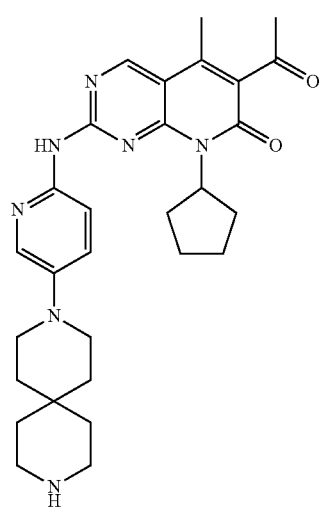
6
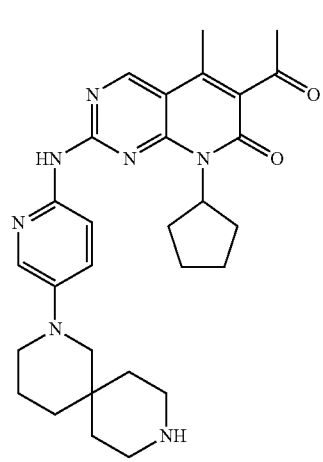
7
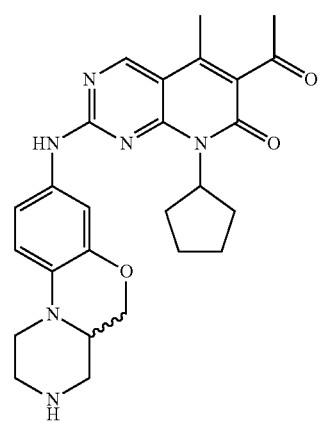
7R
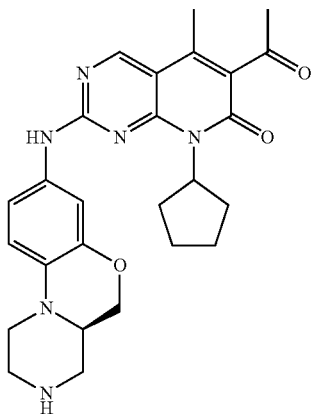

11
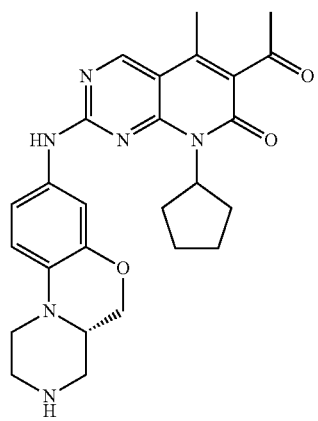
12
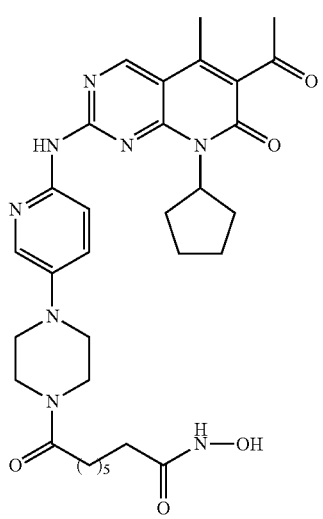
13
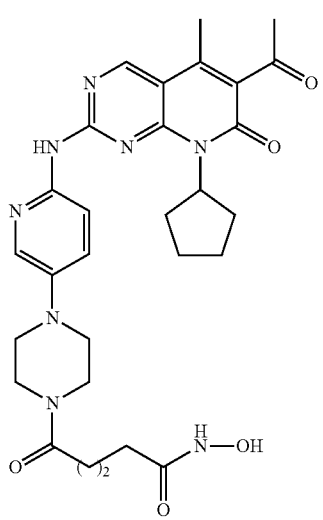
7S
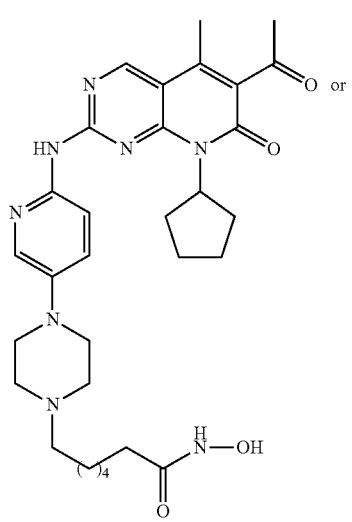
14
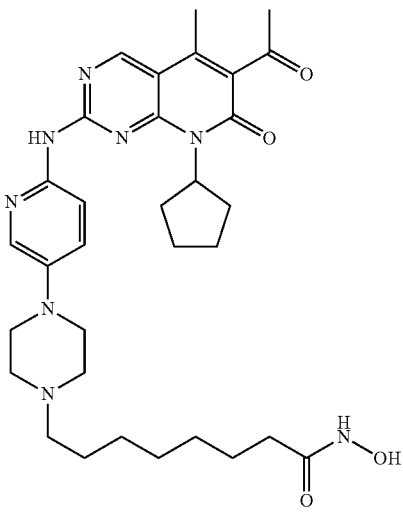
or
15
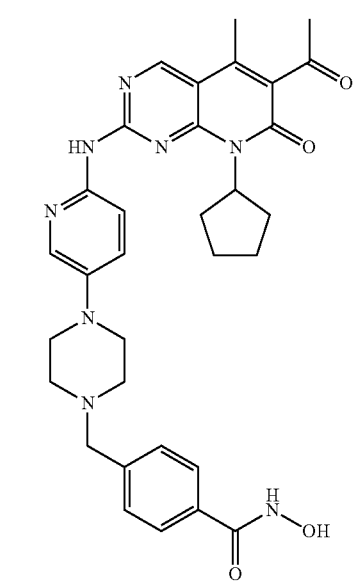
16
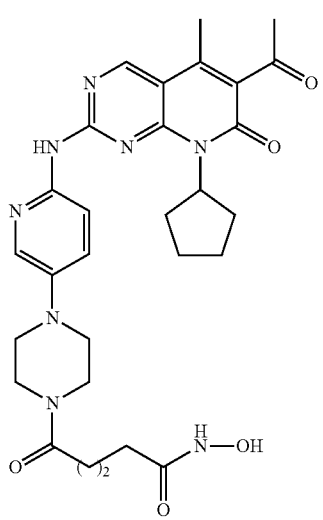

17
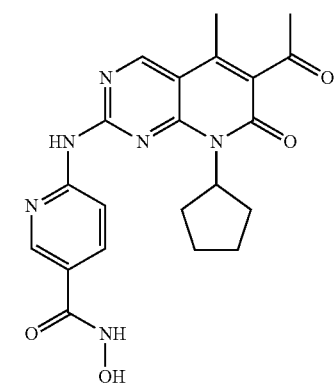
18
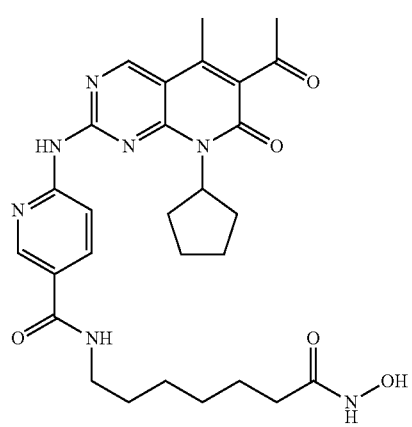
19
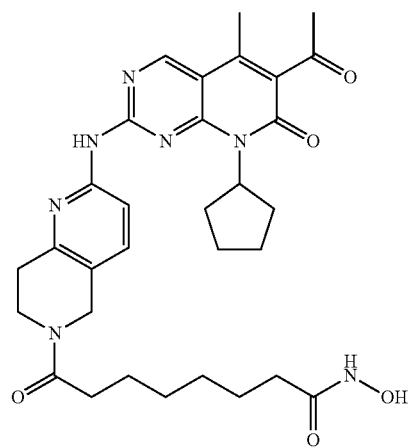
20
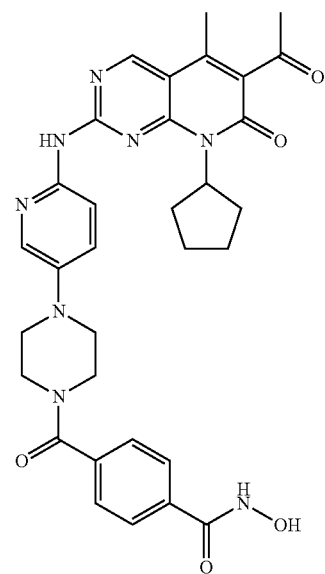
21
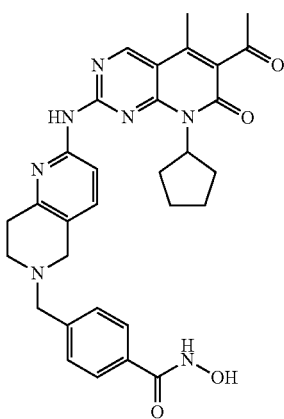
22
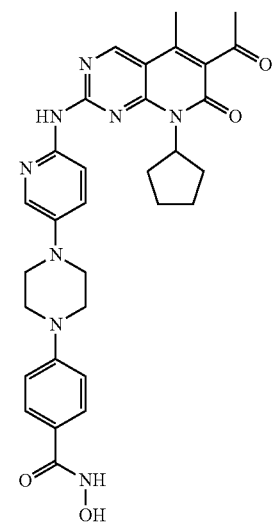

-continued

23

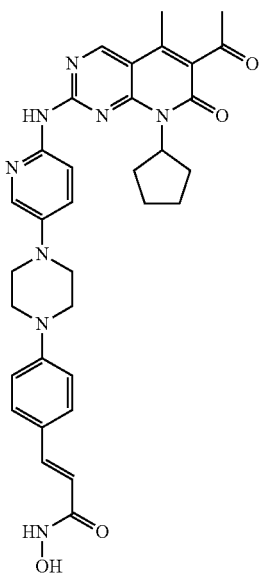

The second aspect of the invention, provided a pharmaceutical composition, wherein comprising the compound of the first aspect of the present invention and a pharmaceutically acceptable carrier or excipient.

The third aspect of the invention, provided a use of a compound of the first aspect of the present invention for the manufacture of a pharmaceutical composition for treating and/or preventing a disease or condition mediated by a cyclin-dependent kinase or a histone deacetylase.

The third aspect of the invention, provided a method for treating a disease or condition mediated by a cyclin-dependent kinase or a histone deacetylase in a subject, comprising administering to the subject in need thereof a therapeutically effective amount of a compound of the first aspect of the present invention or a composition of the second aspect of the present invention.

In another preferred embodiment, the disease or condition is selected from the following group: breast cancer, lymph cancer, leukemia, lung cancer, ovarian cancer, liver cancer, melanoma, colon cancers, rectal cancer, renal-cell carcinoma, cancer of the small intestine and cancer of the esophagus, bladder cancer, prostate cancer, or pharynx cancer.

It should be understood that in the present invention, the technical features specifically described above and below (such as the Examples) can be combined with each other, thereby constituting a new or preferred technical solution, which needs not be specified.

DETAILED DESCRIPTION OF THE INVENTION

Definitions

As use herein, unless clearly indicated otherwise, use of the terms "a", "an" and the like refers to one or more.

As used herein, the word "or" has the meaning of both "or" and "and" and is equivalent to "and/or"—unless otherwise specifically limited to just "or."

As used herein, unless otherwise stated, a chiral carbon atom (or chiral center) of the compound(s) in the invention is optionally R-type, S-type, or a combination thereof.

As used herein, unless otherwise stated, the term "alkyl" by itself or as part of another substituent (which may include the short form of "alk," e.g., alkoxy), refers to a straight (i.e. unbranched), branched chain, or cyclic hydrocarbon radical, or combination thereof, which may be fully saturated, mono- or polyunsaturated and can include di- and multivalent radicals. When an alkyl is preceded by a carbon-number modifier, e.g., $C_{1-10}$, its means the alkyl group contains 1 to 10 carbon atoms. For instance, examples of $C_{1-8}$ alkyl may include a linear or branched alkyl having 1-8 carbon atoms, such as methyl, ethyl, propyl, isopropyl, butyl, isobutyl, sec-butyl, and t-butyl.

As used herein, the term "alkenyl," by itself or as part of another substituent, refers to a straight chain, or branched hydrocarbon chains having at least one carbon-carbon double bond. An alkenyl group with one double bond can be denoted as —$C_nH_{2n-1}$ or —$C_nH_{2n-3}$ with two double bonds. When an alkenyl is preceded by a carbon-number modifier, e.g., $C_{2-8}$, it means the alkenyl group contains 2 to 8 carbon atoms. For instance, examples of $C_{2-8}$ alkenyl may include vinyl, allyl, 1,2-butenyl, 2,3-butenyl, and butadienyl etc.

As used herein, the term "alkynyl," by itself or as part of another substituent, refers to an aliphatic hydrocarbon group with at least one carbon-carbon triple bond. An alkynyl group may be linear or branched or combinations thereof. In some embodiments, it can contain 2 to 12 (e.g., 2 to 8, 2 to 6, or 2 to 4) carbon atoms. When an alkynyl is preceded by a carbon-number modifier, e.g., $C_{2-8}$, it means the alkynyl group contains 2 to 8 carbon atoms. Examples of an alkynyl group (e.g., $C_{2-8}$ alkynyl) may include acetenyl, propynyl, isopropynyl, 1-butynyl, isobutynl, and sec-butynyl etc.

As used herein, the term "cycloalkyl," by itself or as part of another substituent, refers to a saturated or partially saturated carbocyclic mono-, bi-, or tri-cyclic (fused or bridged or spiral) ring system. It can contain 3 to 12 (e.g., 3 to 10, or 5 to 10) carbon atoms. When a cycloalkyl group is preceded by a carbon-number modifier, e.g., $C_{3-10}$, it means the cycloalkyl group contains 3 to 10 carbon atoms. In some embodiments, the term "$C_{3-10}$ cycloalkyl" may refer to a saturated or partially saturated mono- or bicyclic alkyl ring system containing 3 to 10 carbon atoms, such as cyclopropyl, cyclobutyl, cyclopentyl, cyclohexyl, and cycloheptyl. Below are some examples of cycloalkyl group.

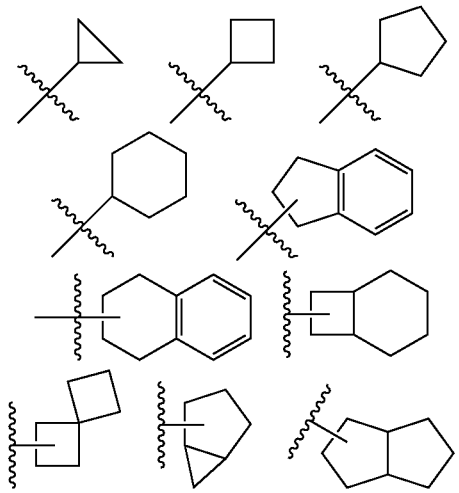

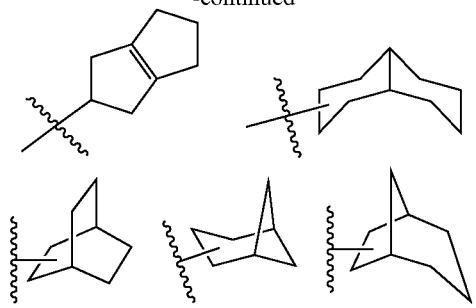

As used herein, the term "alkoxy" or "alkyloxy" refers to an alkyl group linked by an oxygen atom (i.e., —O-alkyl), wherein alkyl is as defined above. Specific examples of "alkoxy" include, but are not limited to, methoxy, ethoxy, n-propoxy, isopropoxy, n-butoxy, iso-butoxy, sec-butoxy, t-butoxy, cyclohexyloxy, and cyclopentyloxy. An alkoxy group can be optionally substituted with one or more appropriate substituents such as halogen, amino, cyano, or hydroxyl. An alkoxy group can be straight or branched. When an alkoxy group is preceded by a carbon-number modifier, e.g., $C_{1-8}$, it means the alkoxy group contains 1 to 8 carbon atoms.

As used herein, the term "halo" or "halogen," by itself or as part of another substituent (e.g., haloalkyl), may refer to and include F, Cl, Br, and/or I.

As used herein, a "carbonyl" group refers to —C(O)— or —C(=O)—.

As used herein, the term "aryl," by itself or as part of another substituent, refers to and includes monocyclic, bicyclic, or polycyclic aromatic hydrocarbon radicals. An aryl group can be substituted or unsubstituted. When an aryl group is preceded by a carbon-number modifier, e.g., $C_{6-12}$, it means the aryl group contains 6 to 12 carbon atoms. Aryl group can be fused with another all-carbon containing cyclic structure (including saturated, partial saturated, or aromatic ring). But the attaching point to the parent structure has to be from aromatic ring system to be able to qualify as aryl. When attaching point to parent structure is on a saturated carbon atom, it can be called as cycloalkyl instead of aryl. Examples of an aryl group include but are not limited to phenyl, biphenylyl, and naphthyl.

Below are some examples of cycloalkyl group.

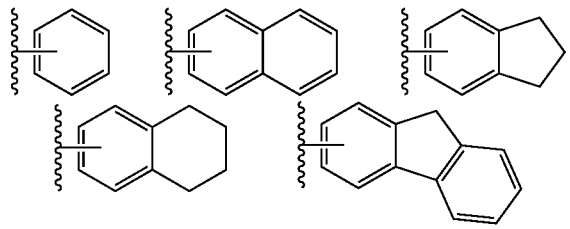

As used herein, the term "heteroaryl," by itself or as part of another substituent, refers to a monocyclic or polycyclic aromatic hydrocarbon radicals, having the number of annular carbon atoms designated (e.g., $C_{4-10}$ means four to ten annular carbon atoms) and containing at least one or more of the same or different heteroatoms each independently being N, O, or S. Each carbon atom may be optionally substituted. A heteroaryl group may be 5- to 15-membered aromatic group containing 1 to 4 heteroatoms each independently being N, O, or S. A heteroaryl group may include a nitrogen containing heteroaryl, an oxygen containing heteroaryl, a sulfur containing heteroaryl.

As used herein, the term "nitrogen containing heteroaryl" refers to an aromatic group having one or more nitrogen atoms in the ring(s). Preferably, it is $C_{4-10}$ nitrogen containing heteroaryl which is an aromatic group having 4 to 10 carbon atoms and one or more nitrogen atoms in the ring. Specific examples include but are not limited to substituted or unsubstituted pyridinyl, pyrimidinyl, and pyrrolyl.

As used herein, the term "oxygen containing heteroaryl" refers to an aromatic group having one or more oxygen atoms in the ring(s). Preferably, it is $C_{4-10}$ nitrogen-containing heteroaryl which is an aromatic group having 4 to 10 carbon atoms and one or more oxygen atoms in the ring(s), such as optionally substituted furyl and benzofuryl.

As used herein, the term "sulfur containing heteroaryl" refers to an aromatic group having one or more sulfur atoms in the ring(s). Preferably, it is $C_{4-10}$ sulfur containing heteroaryl which is an aromatic group having 4 to 10 carbon atoms and one or more sulfur atoms in the ring, such as optionally substituted thienyl.

Below are some examples of heteroaryl group.

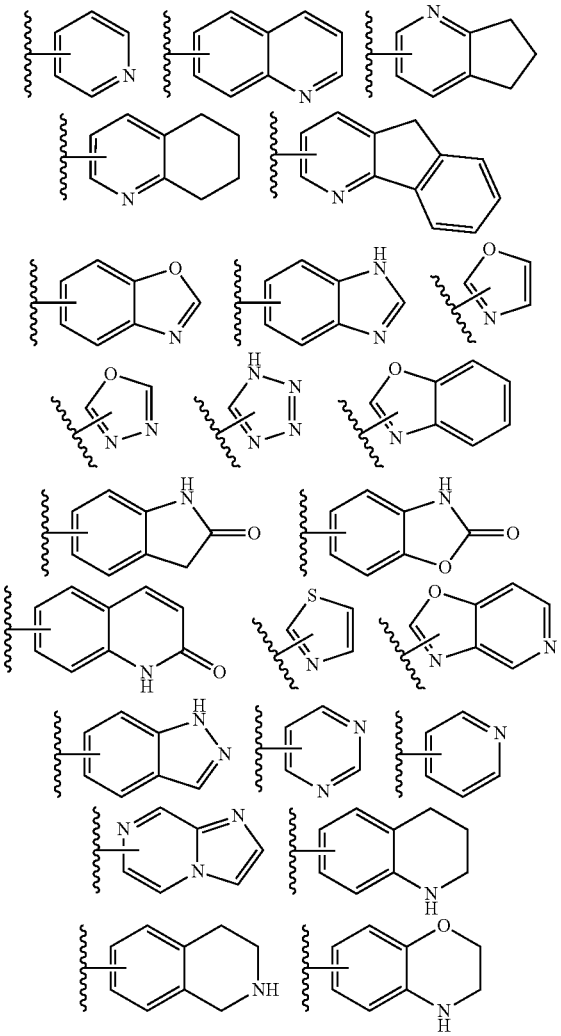

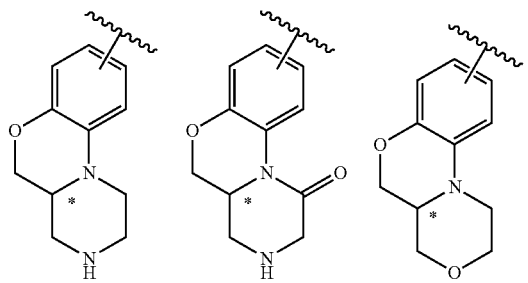
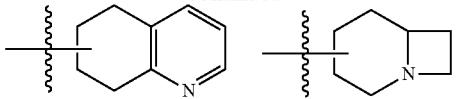

As used herein, the term "heterocyclyl," by itself or as part of another substituent, refers to mono- or polycyclic radicals which may be saturated, partially saturated, or fully unsaturated, having the number of annular carbon atoms designated (e.g., $C_{3-11}$ means three to eleven annular carbon atoms) and containing at least one or more of the same or different heteroatoms each independently being N, S, or O. A heterocyclyl group may be 3- to 15-membered group containing 1 to 4 heteroatoms each independently being N, O, or S. A heteroaryl group may include a nitrogen containing heterocyclyl, oxygen containing heterocyclyl, and sulfur containing heterocyclyl, nitrogen and oxygen containing heterocyclyl, nitrogen and sulfur containing heterocyclyl, sulfur and oxygen containing heterocyclyl, etc. Below are some examples of heterocycle.

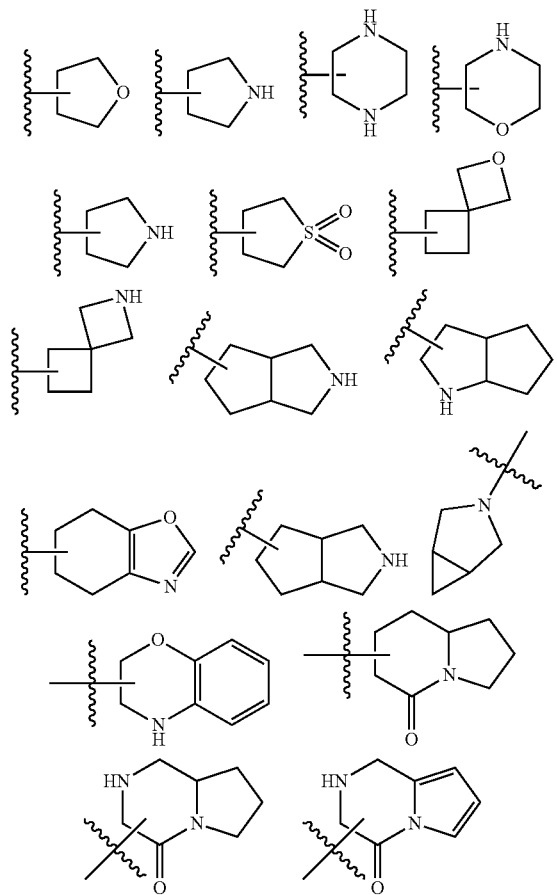

As used herein, the term "optionally" (e.g., as in "optionally substituted with") means that the moiety at issue is either substituted or not substituted, and that the substitution occurs only when it is chemically feasible. For instance, H cannot be substituted with a substituent and a covalent bond or —C(=O)— group cannot be substituted with a substituent.

As used herein, an "oxo" or "oxide" group refers to =O.

As used herein, the term "pharmaceutically acceptable salt"—unless otherwise specified—refers to salts which are suitable for use in contact with the tissues of a subject (e.g., human) without excessive adverse effect. In some embodiments, pharmaceutically acceptable salts include salts of a compound of the invention having an acidic group (e.g., potassium salts, sodium salts, magnesium salts, calcium salts) or a basic group (e.g., sulfate, hydrochloride, phosphate, nitrate, carbonate).

As used herein, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different in every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds. Examples of the substituents include but are not limited to $C_{1-8}$ alkyl, $C_{2-8}$ alkenyl, $C_{2-8}$ alkynyl, $C_{3-10}$ cycloalkyl, $C_{1-8}$ alkyloxy, halogen, hydroxyl, carboxyl(-COOH), $C_{1-8}$ aldehyde, $C_{2-10}$ acyl, $C_{2-10}$ ester, amino, amido, phenyl. For instance, a phenyl may be optionally substituted with 1-3 substituents each independently is halogen, $C_{1-10}$ alkyl, cyano, OH, nitro, $C_{3-10}$ cyclic hydrocarbyl, $C_{1-8}$ alkoxy, or amino.

For convenience and as commonly understood, the term "optionally substituted" only applies to the chemical entities that can be substituted with suitable substituents, not to those that cannot be substituted chemically.

Unless specifically otherwise defined, all the terms used herein have their common meanings as known to a skilled person in the art.

In one preferred embodiment, a compound of Formula (I) is selected from the compounds shown above.

In a preferred embodiment, each of $R^1$, $R^{1a}$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ in Formula (I) independently is selected from the corresponding groups included by the specific compounds shown above.

It should be understood that a deuterium-enriched derivative or different crystal forms of a compound of Formula (I) also fall with the scope of the present application.

GENERAL SYNTHETIC SCHEMES FOR THE COMPOUNDS OF THIS INVENTION

Abbreviation

Boc$_2$O=di-tert-butyl dicarbonate
Cs$_2$CO$_3$=cesium carbonate
DAST=diethylaminosulfur trifluoride
DCM=dichloromethane
DIPEA=N,N-diisopropylethylamine
DMAP=4-dimethylaminopyridine
DMF=N,N-dimethylformamide
DMSO=dimethyl sulphoxide
e.e.=enantiomeric access
EtOAc or EA=ethyl acetate
HATU=(1-[bis(dimethylamino)methylene]-1H-1,2,3-triazolo[4,5-b]pyridinium 3-oxid hexafluorophosphate)
MgCl$_2$=magnesium chloride
NH$_4$HCO$_3$=ammonium bicarbonate
Pd(OAc)$_2$=palladium(II) acetate
Pd$_2$dba$_3$=tris(dibenzylideneacetone)dipalladium(O)
PE=petroleum ether
RT=room temperature
TEA=triethylamine
TFA=trifluoroacetic acid Generally, the reaction is carried out in an inert solvent and at a temperature of −40 to reflux temperature (such as 100 or 120° C.) with a reaction time of from 1 min to 72 hours and preferably 0.1-24 hours or 0.2-12 hours. The exemplary solvents and temperature are those used in the Examples.

Scheme A illustrates a general synthesis of Compound A7.

Scheme A

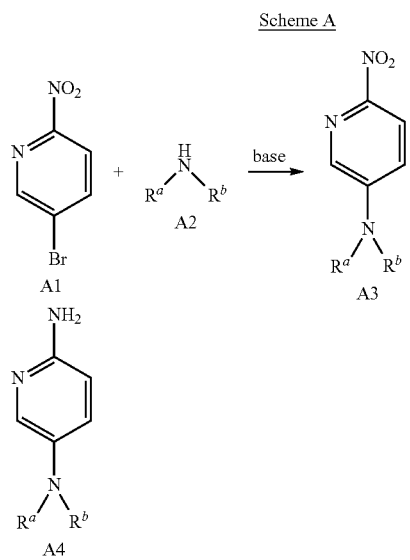

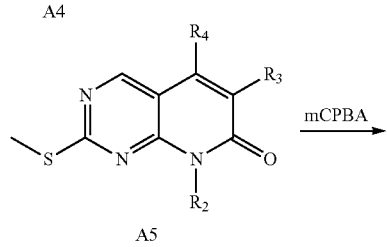

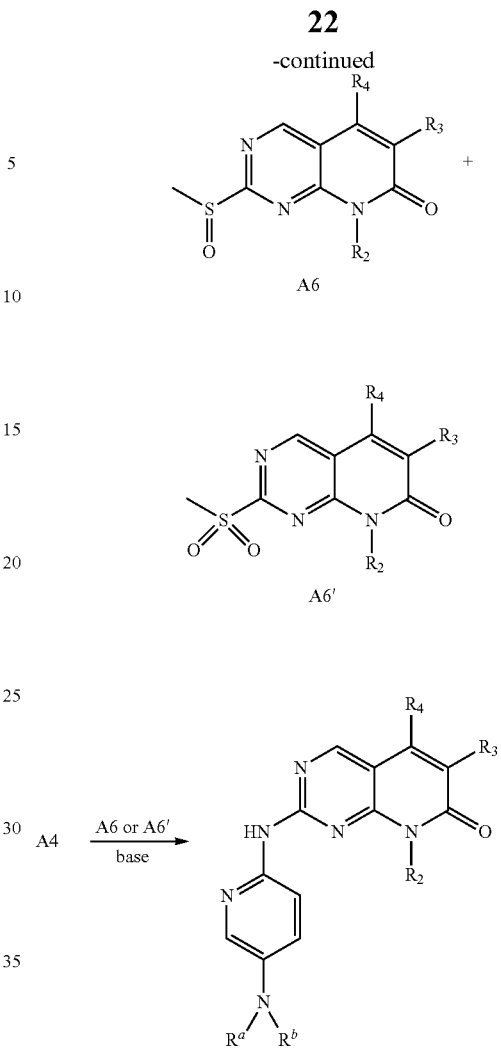

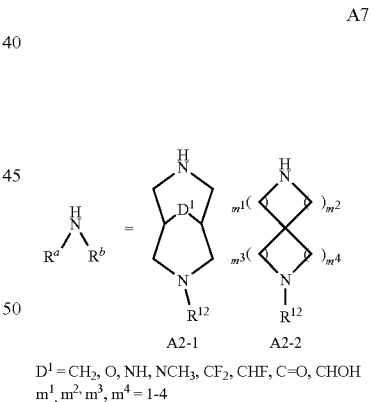

D$^1$ = CH$_2$, O, NH, NCH$_3$, CF$_2$, CHF, C=O, CHOH
m$^1$, m$^2$, m$^3$, m$^4$ = 1-4

Scheme B illustrates a general synthesis of Compound B4.

Scheme B

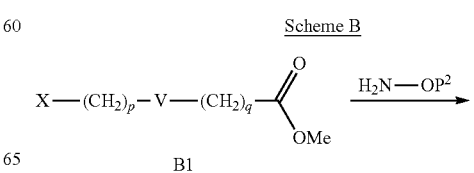

23
-continued
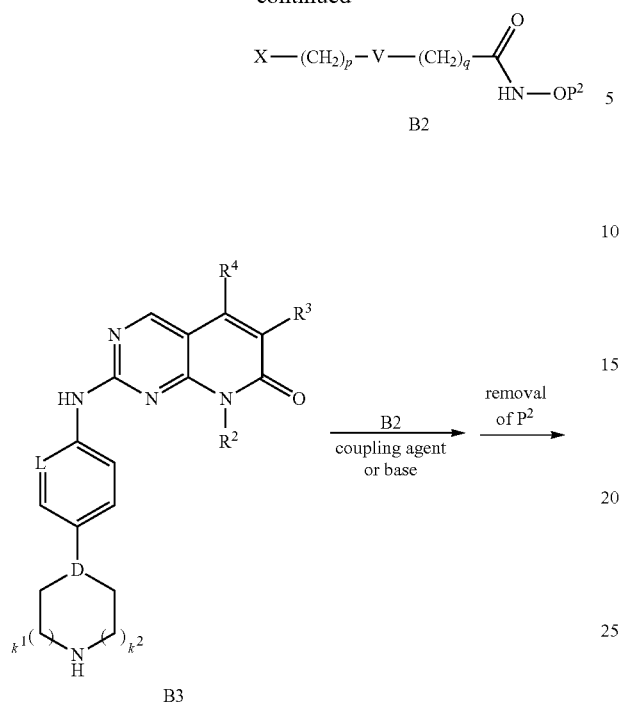
B3
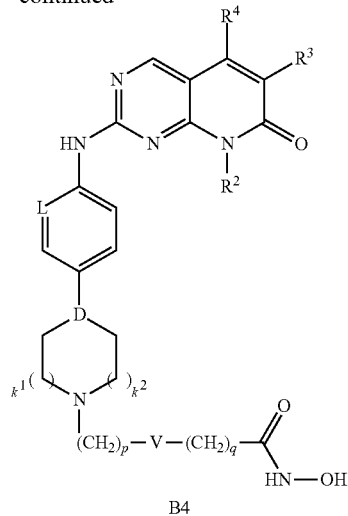
B2
removal of P²
→
24
-continued
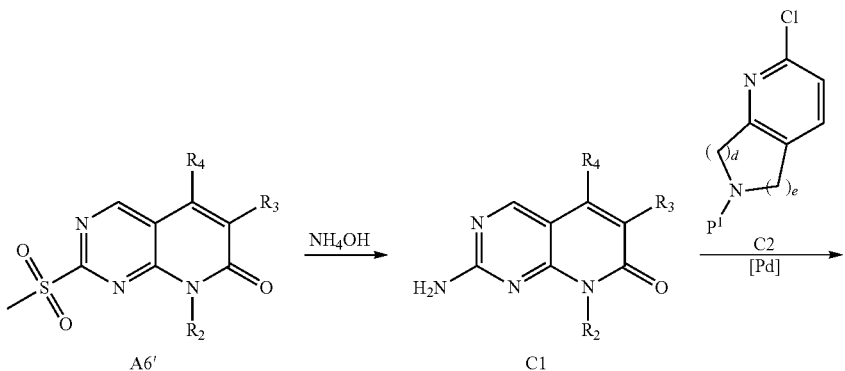
B4
X = Cl, Br, I
P² = protecting group
D = N, CH
L = N, CH
k¹, k² = 0-3
V, p, q as defined above
Scheme C illustrates a general synthesis of Compound C4.
Scheme C
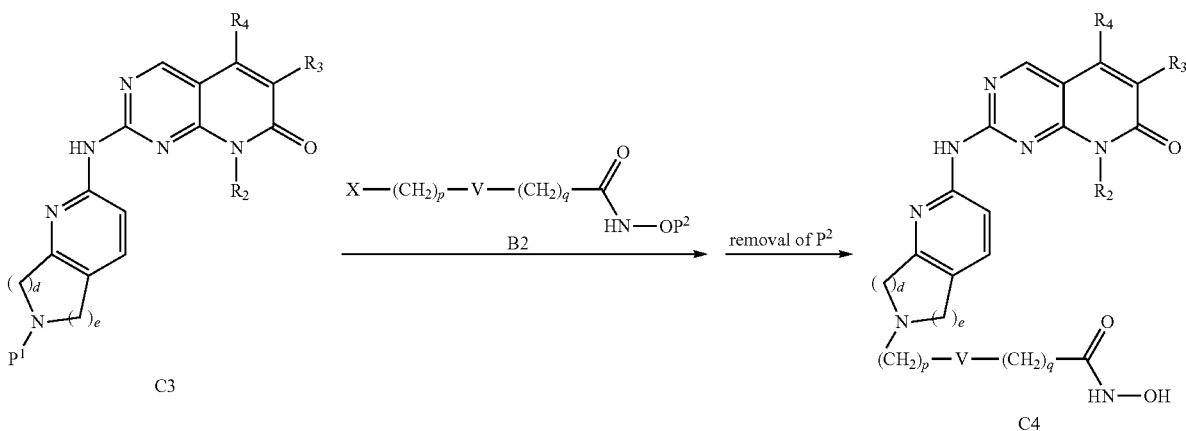

Scheme D illustrates a general synthesis of Compound D5A and D5B.
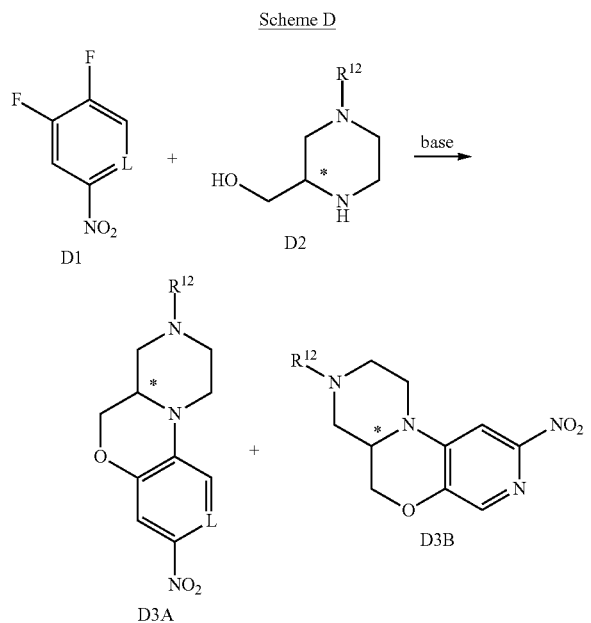
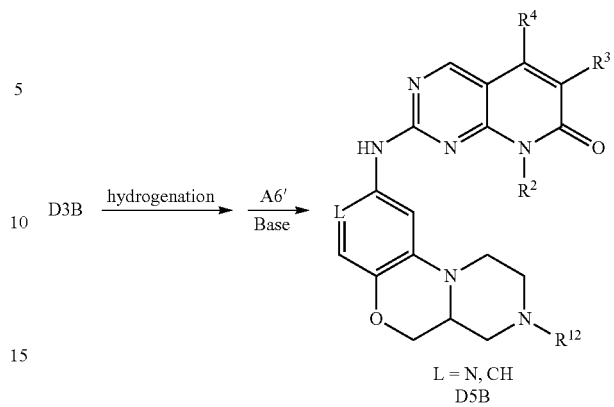
Alternatively, Compound D5A (L=N) and D5B (L=N) and can be prepared according to Scheme E.
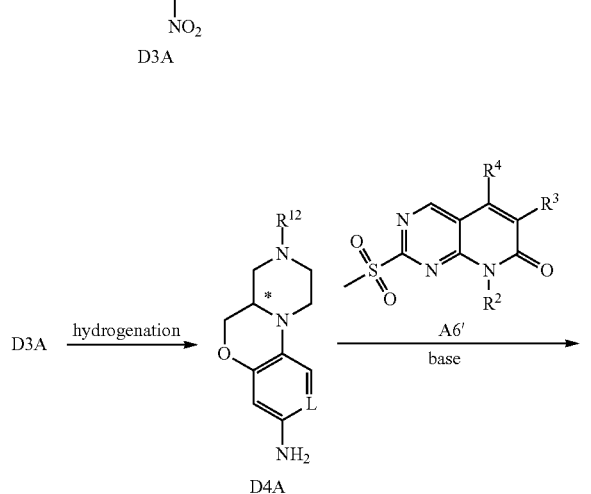
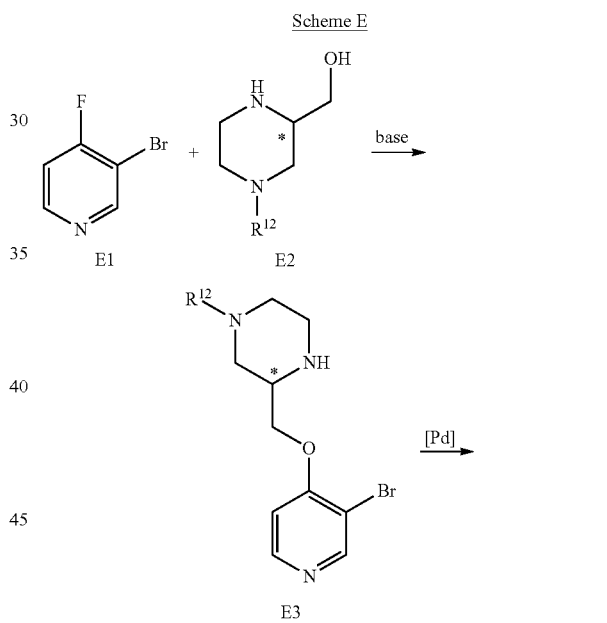
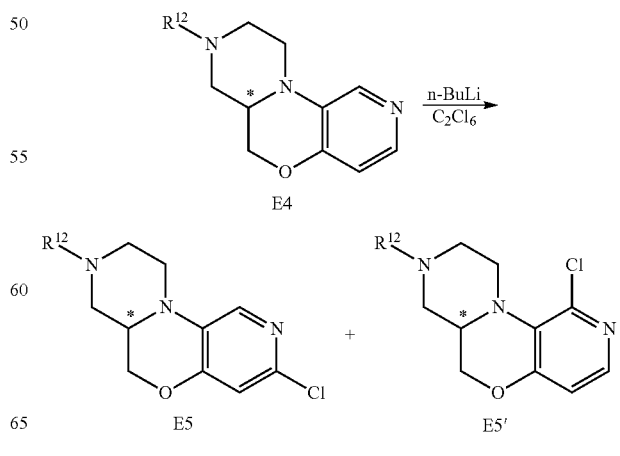

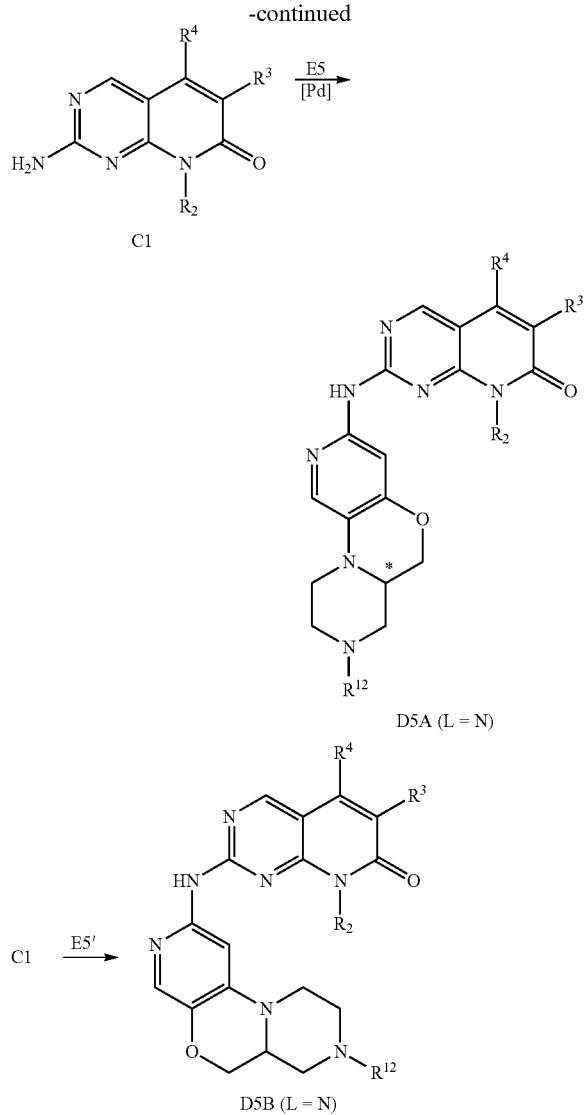

Pharmaceutical Compositions and Administration Thereof

The compounds provided by the present invention are useful as kinase inhibitors, especially as inhibitors of CDK4 and/or CDK6, and/or HDAC inhibitors. Therefore, these compounds possess outstanding therapeutic effect for cancer.

The pharmaceutical composition according to the present invention comprises (i) a safe and effective amount of the compounds of the invention or the pharmaceutical acceptable salts thereof and (ii) a pharmaceutically acceptable excipient or carrier. As used herein, the term "safe and effective amount" means an amount of the compounds which is sufficient to improve the patient's condition and will not induce any serious side effect. Generally, the pharmaceutical composition contains 0.01-100 mg compounds of the invention/dose, preferably 0.10-10 mg compounds of the invention/dose. In some embodiments, "one dose" refers to a capsule or tablet.

A "pharmaceutically acceptable carrier" means one or more compatible solid or liquid fillers or gel materials, which are suitable for human, and usually must have sufficient purity and sufficiently low toxicity. The term "compatibility" as used herein means that the components of the compositions can be blended with the compounds of the invention or with each other, and would not significantly reduce the efficacy of the compounds. Examples of pharmaceutically acceptable carriers include but are not limited to cellulose and the derivatives thereof (such as sodium carboxymethyl cellulose, sodium ethyl cellulose, cellulose acetate, etc.), gelatin, talc, solid lubricants (such as stearic acid and magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, and pyrogen-free water.

There is no special limitation to the route of administration for the compounds or pharmaceutical compositions of the invention. The representative administration route includes but is not limited to: oral, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and gum arabic; (c) humectant, such as, glycerol; (d) disintegrating agents such as agar, calcium carbonate, potato starch or tapioca starch, alginic acid, certain complex silicates, and sodium carbonate; (e) dissolution-retarding agents, such as paraffin; (f) absorption accelerators, for example, quaternary ammonium compounds; (g) wetting agents, such as cetyl alcohol and single glyceryl stearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffer.

The solid dosage forms such as tablets, sugar pills, capsules, pills and granules can be prepared by using coating and shell material, such as enteric coatings and other materials known in the art. They can contain opaque agent, and the release of the active compounds or compounds in such compositions can be delayed for releasing in certain portion of the digestive tract. Instance of the embedding components can be polymers and waxes. If necessary, the active compounds and one or more above excipients can be prepared into microcapsules.

Liquid dosage forms for oral administration include pharmaceutically acceptable emulsions, solutions, suspensions, syrups or tinctures. In addition to the active compounds, the liquid dosage forms may contain conventional inert diluent known in the art, such as water or other solvent, solubilizer and emulsifier, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the mixtures thereof and so on.

Besides the inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the mixtures thereof and so on.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and the suitable mixtures thereof.

The dosage forms of compounds of the invention for topical administration include ointments, powders, patches, aerosol, and inhalants. The active ingredients are mixed with physiologically acceptable carriers and any preservatives, buffers, or propellant if necessary, under sterile conditions.

The compounds of the invention can be administered alone, or in combination with other pharmaceutically acceptable compounds.

When the pharmaceutical compositions are used, a safe and effective amount of compounds of the present invention is administered or delivered to mammals in need thereof (such as human), wherein the dosage of administration is a pharmaceutically effective amount. For a person weighted about 60 kg, the daily dose is usually 1 to 2000 mg, preferably 20 to 500 mg. Of course, the particular dose should also depend on other factors, such as the route of administration, patient healthy status, etc., which are well within the skill of a skilled physician.

The compounds and pharmaceutical composition of the invention can be used for treating cancer. As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting prostate, lung, breast, lymphoid, gastrointestinal (e.g., colon), and genitourinary tract (e.g., renal, urothelial cells), pharynx. Adenocarcinomas include malignancies such as most colon cancers, rectal cancer, renal-cell carcinoma, liver cancer, non-small cell carcinoma of the lung, cancer of the small intestine and cancer of the esophagus. Metastatic lesions of the aforementioned cancers can also be treated or prevented using the methods and compositions of the invention. The subject method can be useful in treating malignancies of the various organ systems, such as those affecting lung, breast, lymphoid, gastrointestinal (e.g., colon), bladder, genitourinary tract (e.g., prostate), pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The examples of cancer include but are not limited to breast cancer, lymph cancer, lung cancer, ovarian cancer, liver cancer melanoma, colon cancers, rectal cancer, renal-cell carcinoma, cancer of the small intestine and cancer of the esophagus, bladder cancer, prostate cancer, or pharynx cancer, etc.

The main advantages of the present invention include at least the following:

(1) The invention provides novel heterocyclic compounds useful as kinase inhibitors and/or histone deacetylase inhibitors;

(2) The invention reveals that these novel heterocyclic compounds of Formula (I) possess outstanding effect for inhibiting activity of CDK4, CDK6, and/or HDACs.

The present invention will be further illustrated below with reference to the specific examples. It should be understood that these examples are only to illustrate the invention but not to limit the scope of the invention. Unless indicated otherwise, parts and percentage are calculated by weight.

Example 1. Preparation of 2-(5-(3,7-diazabicyclo[3.3.1]nonan-3-yl)pyridin-2-ylamino)-6-acetyl-8-cyclopentyl-5-methylpyrido[2,3-d]pyrimidin-7(8H)-one (Compound 1)

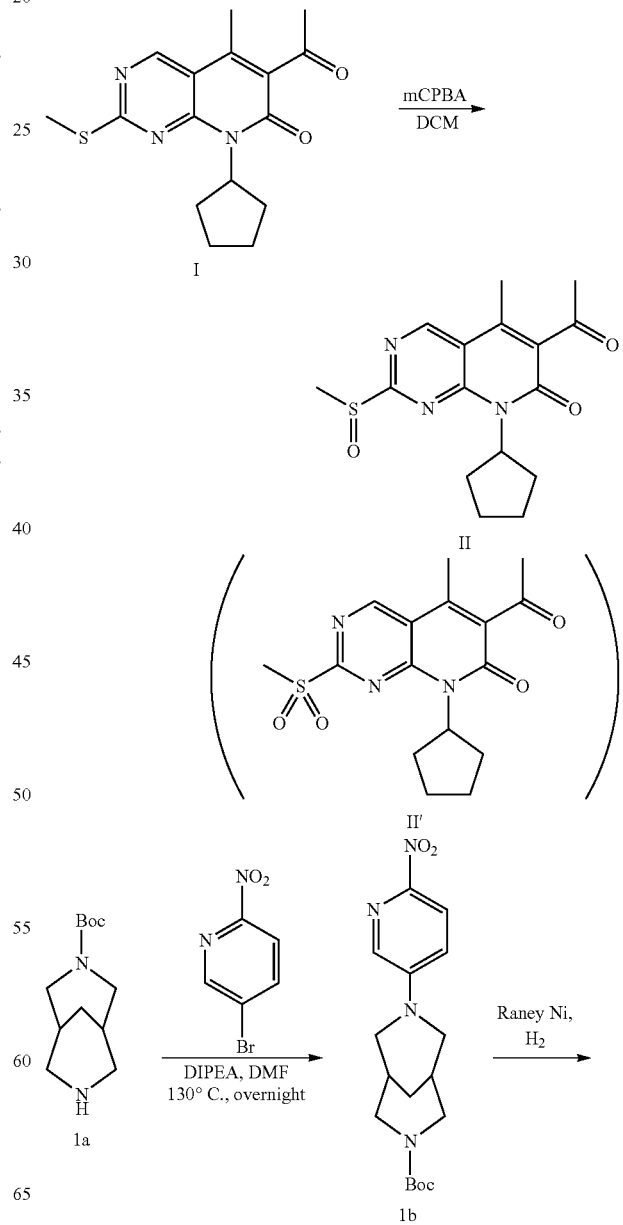

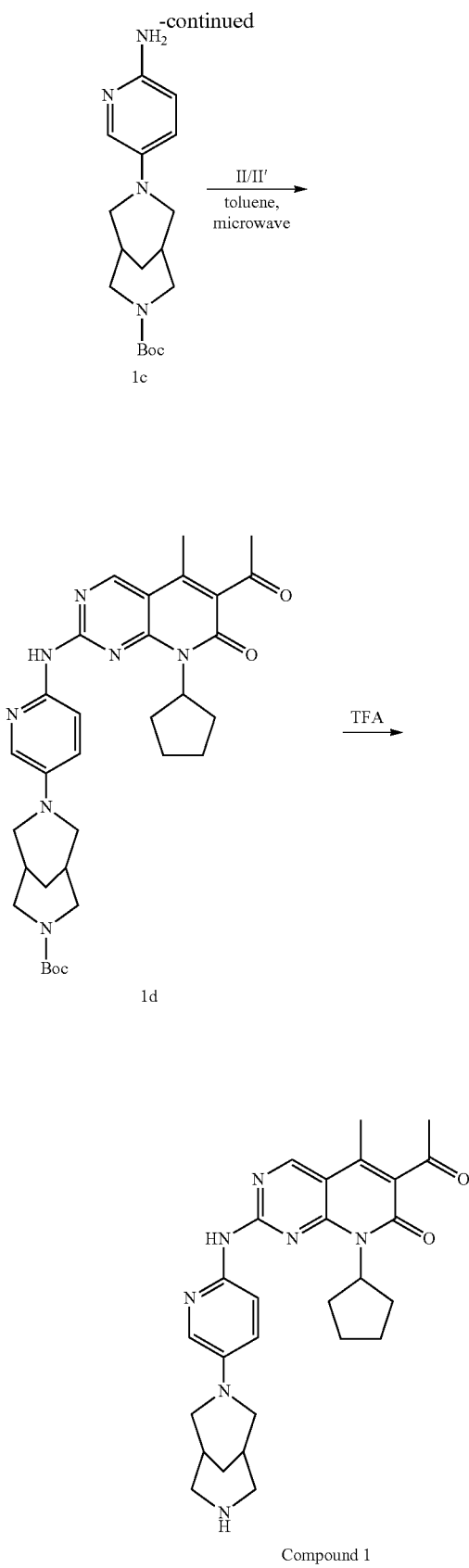

To a mixture of compound I (430 mg, 1.35 mmol, prepared according to J. Med. Chem., 2005, 48(7), 2371-2387) in methylene chloride (25 mL) was added m-chloroperbenzoic acid (mCPBA, >95%, 245 mg, 1.35 mmol) portionwise at 0° C. under nitrogen protection. The mixture was stirred at room temperature for 3 hours, and then was poured into sat. aq. NaHCO$_3$ (100 mL) and extracted with methylene chloride (3×100 mL). The combined organic solution was dried over MgSO$_4$ and concentrated in vacuo to give yellow oil, which was then purified by flash chromatography (25% EtOAc in petroleum ether) to give a mixture of compound II and II' (300 mg, yield 75%) as a yellow solid. The mixture of compounds II/II' was used for the next step without further separation. II: ESI$^+$ m/z 334.1 (M+1); II': ESI$^+$ m/z 350.1 (M+1).

A mixture of 5-bromo-2-nitropyridine (322 mg, 1.59 mmol), 3-Boc-3,7-diazabicyclo[3.3.1]nonane hydrochloride (1a, 500 mg, 1.90 mmol) and DIPEA (960 mg, 7.44 mmol) in DMF (5 mL) was stirred at 120° C. for 3 hours. The desired compound was detected by LC-MS and the reaction mixture was directly purified by prep-HPLC to give 3-Boc-7-(6-nitropyridin-3-yl)-3,7-diazabicyclo[3.3.1]nonane (1b) (258 mg, 47% yield) as a yellow solid. $^1$H NMR (400 MHz, CDCl$_3$) δ (ppm) 8.14 (d, J=9.2 Hz, 1H), 8.10 (d, J=2.8 Hz, 1H), 7.18 (dd, J=9.2 Hz and 2.8 Hz, 1H), 4.45 (d, J=13 Hz, 1H), 4.22 (d, J=13 Hz, 1H), 4.04 (d, J=13 Hz, 1H), 3.92 (d, J=13 Hz, 1H), 3.28 (d, J=13 Hz, 1H), 3.23 (d, J=13 Hz, 1H), 3.14 (d, J=13 Hz, 1H), 3.01 (d, J=13 Hz, 1H), 2.17-2.08 (m, 2H), 2.00-1.90 (m, 2H), 1.13 (s, 9H); ESI$^+$ m/z 371.1 (M+23 (Na$^+$)), 293.1 (M−55).

To a mixture of compound Tb (250 mg, 0.718 mmol) and Raney nickel (100 mg) in methanol (50 mL) was added hydrazine hydrate (50 mg) at 0° C., and the mixture was stirred at RT for an hour. Then the reaction mixture was filtered through celite. The filtrate was concentrated and the residue was extracted with methylene chloride (3×40 mL). The combined organic solution was dried over Na$_2$SO$_4$ and concentrated in vacuo to give 3-Boc-7-(6-aminopyridin-3-yl)-3,7-diazabicyclo[3.3.1]nonane (1c) (190 mg, yield 87%) as a brown solid. ESI$^+$ m/z 319.2 (M+1).

A mixture of 3-Boc-7-(6-aminopyridin-3-yl)-3,7-diazabicyclo[3.3.1]nonane (1c) (190 mg, 0.597 mmol) and the mixture of II/II' (200 mg, ~0.6 mmol) in toluene (20 mL) was stirred at 100° C. overnight. The volatiles were removed in vacuo and the residue was purified by prep-HPLC to give the title compound Id (28 mg, yield 8%) as a white solid. ESI$^+$ m/z 588.3 (M+1).

To a solution of compound Id (28 mg, 0.048 mmol) in methylene chloride (5 mL) was added TFA (1 mL). The reaction mixture was stirred at room temperature for 3 hours. The volatiles were removed in vacuo and the residue was added into sat. aq. NaHCO$_3$ (~4 mL, pH~7). The mixture was directly purified by prep-HPLC (Column: Xbridge Prep C18 10 um OBD, 19*250 mm; Mobile Phase: A: water+10 mm (NH$_4$HCO$_3$), B: acetonitrile; Gradient 32-52% B in 10 min) to give title compound 1 (12 mg, yield 51%) as a yellow solid (free base). $^1$H-NMR (500 MHz, CD$_3$OD) δ (ppm) 8.95 (s, 1H), 8.12 (d, J=3.0 Hz, 1H), 8.01 (d, J=9.0 Hz, 1H), 7.61 (dd, J=9.0 Hz and 3.0 Hz, 1H), 5.99-5.95 (m, 1H), 3.89 (d, J=12 Hz, 2H), 3.30-3.28 (m, 2H), 3.13-3.10 (m, 4H), 2.50-2.46 (m, 1H), 2.40 (s, 3H), 2.39-2.32 (m, 2H), 2.06-1.75 (m, 10H), 1.74-1.63 (m, 2H); ESI$^+$ m/z 488.4 (M+1).

Example 2. Preparation of 2-(5-(9-oxa-3,7-diazabicyclo[3.3.1]nonan-3-yl)pyridin-2-ylamino)-6-acetyl-8-cyclopentyl-5-methylpyrido[2,3-d]pyrimidin-7(8H)-one (Compound 2)

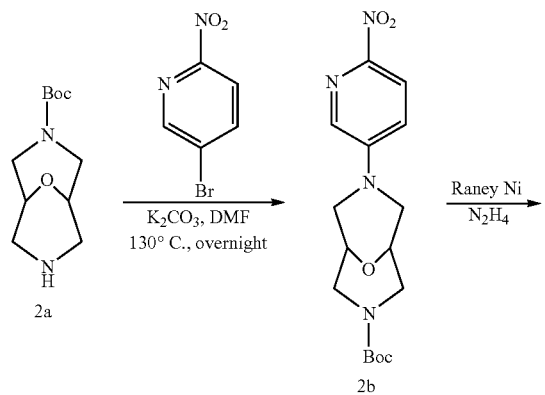

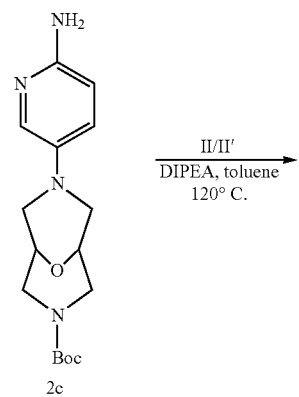

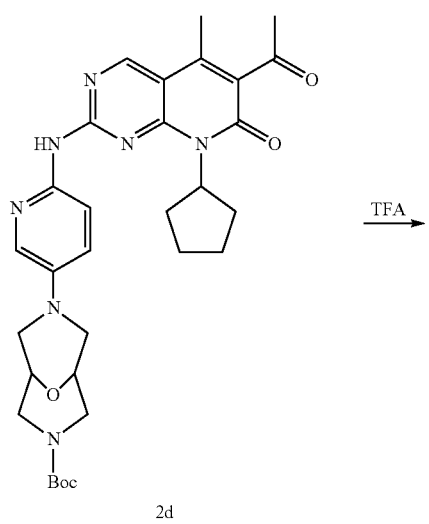

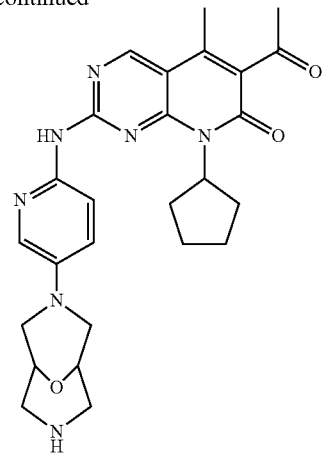

Compound 2

A mixture of 5-bromo-2-nitropyridine (250 mg, 1.24 mmol), potassium carbonate (342 mg, 2.48 mmol) and 3-Boc-9-oxa-3,7-diazabicyclo[3.3.1]nonane (2a) (339 mg, 1.49 mmol) in DMF (4 mL) was stirred at 120° C. overnight. The resulting mixture was diluted with water and extracted with ethyl acetate. The combined organic solution was dried over $Na_2SO_4$ and concentrated in vacuo. The residue was recrystallized from petroleum ether/ethyl acetate to give desired product compound 2b (240 mg, yield 55%) as a brown solid. $ESI^+$ m/z 373.0 (M+23 ($Na^+$)) (two isomers with similar polarity on TLC, Retention time:isomer 1:1.12 min, 66%, isomer 2: 1.24 min, 33%).

A mixture of compound 2b (240 mg, 0.68 mmol, two isomers), Raney Ni (5.87 mg, 0.10 mmol) and hydrazine hydrate (34.0 mg, 0.68 mmol) in methanol (15 mL) was stirred at RT for one hour. The resulting mixture was filtered through celite and the filtrate was concentrated in vacuo to give 3-Boc-7-(6-aminopyridin-3-yl)-9-oxa-3,7-diazabicyclo[3.3.1]nonane (2c) (210 mg, yield 95%) as a dark yellow solid, which was used for the next step without further purification: $ESI^+$ m/z 321.1 (M+1) (two isomers with similar polarity, Retention time:isomer 1:1.17 min, 72%, isomer 2:1.11 min, 27%).

A mixture of intermediate II/II' (200 mg, 0.60 mmol) and compound 2c (210 mg, 0.66 mmol, two isomers) and DIPEA (116 mg, 0.90 mmol) in toluene (3 mL) was stirred at 120° C. overnight. The volatiles were removed in vacuo and the residue was purified by prep-HPLC to give compound 2d (57 mg, 16% yield) as a yellow solid. $ESI^+$ m/z 590.2 (M+1) (two isomers with similar polarity, retention time:isomer 1:1.88 min, 76%, isomer 2: 1.91 min, 23%).

A mixture of compound 2d (57 mg, 0.10 mmol) and TFA (1 mL) in DCM (3 mL) was stirred at RT overnight. The volatiles were removed in vacuo and the residue was purified by prep-HPLC to give compound 2 (44 mg) as a yellow solid. The mixture was further purified using chiral HPLC (Column: CHIRALPAK AY—H20*250 mm, 5 um (Daicel); Mobile phase: 100% Ethanol (0.1% DEA) to give compound 2 (30 mg, yield 61%) as a yellow oil (free base). $^1$H NMR (400 MHz, $CDCl_3$) δ (ppm) 8.80 (s, 1H), 8.22 (d, J=9.0 Hz, 1H), 8.04 (d, J=3.0 Hz, 1H), 7.92 (s, 1H), 7.36-7.26 (m, 1H), 5.91-5.86 (m, 1H), 3.89 (m, 2H), 3.62 (d, J=11.7 Hz, 2H), 3.45 (d, J=13.6 Hz, 2H), 3.35 (d, J=11.0 Hz, 2H), 3.12 (d, J=14.0 Hz, 2H), 2.55 (s, 3H), 2.38-2.31 (m, 5H), 2.08-2.04 (m, 2H), 1.91-1.85 (m, 2H), 1.72-1.68 (m, 2H); ESI⁺ m/z 489.9 (M+1) (retention time: 7.19 min).

Example 3. Preparation of 2-(5-(2,7-Diazaspiro[3.5]nonan-7-yl)pyridin-2-ylamino)-6-acetyl-8-cyclopentyl-5-methylpyrido[2,3-d]pyrimidin-7(8H)-one (Compound 3)

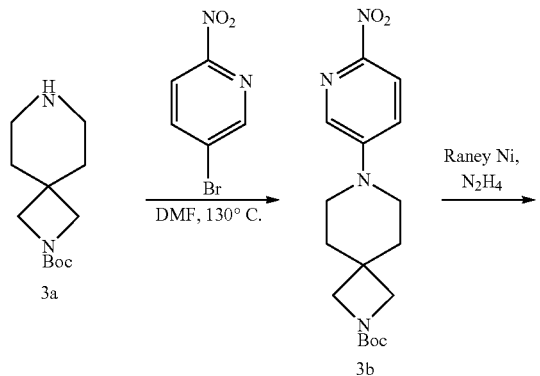

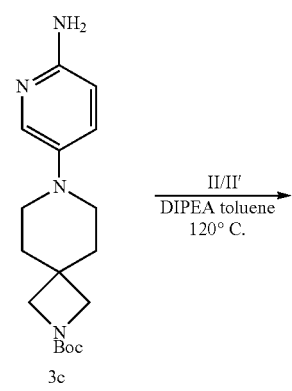

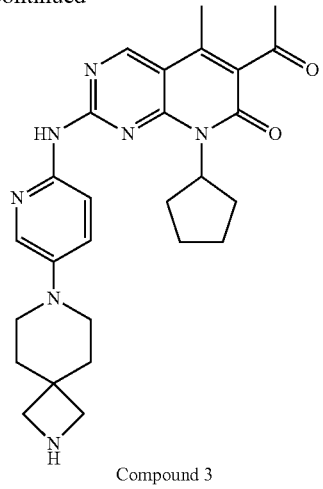

A mixture of 5-bromo-2-nitropyridine (400 mg, 1.77 mmol), 2-Boc-2,7-diazaspiro[3.5]nonane (3a) (428 mg, 2.12 mmol) and DIPEA (685 mg, 5.31 mmol) in DMF (4 mL) was stirred at 120° C. overnight. The resulting mixture was diluted with water (50 mL) and extracted with ethyl acetate (3×30 mL). The combined organic solution was dried over Na₂SO₄ and concentrated in vacuo. The residue was recrystallized from petroleum ether/ethyl acetate to give compound 3b (737 mg) as a yellow solid. ESI⁺ m/z 349.1 (M+1), 293.2 (M−55).

A mixture of 2-Boc-7-(6-nitropyridin-3-yl)-2,7-diazaspiro[3.5]nonane (3b) (0.45 g, 70%, 0.91 mmol), Raney Ni (5.9 mg, 0.10 mmol) and hydrazine hydrate (45.2 mg, 0.91 mmol) in methanol (15 mL) was stirred at room temperature for 1 hour. After filtrated through celite, the filtrate was concentrated to give the crude compound 3c (280 mg, yield 30% in 2 steps) as a yellow solid: ESI⁺ m/z 319.4 (M+1).

A mixture of II/II' (200 mg, 0.6 mmol) and 2-Boc-7-(6-aminopyridin-3-yl)-2,7-diazaspiro[3.5]nonane (3c) (280 mg, 0.78 mmol) and DIPEA (116 mg, 0.90 mmol) in toluene (3 mL) was stirred at 120° C. overnight. The volatiles were removed in vacuo and the residue was purified by prep-HPLC to give compound 3d (40 mg, 11% yield) as a yellow solid: ESI⁺ m/z 588.3 (M+1).

A mixture of compound 3d (30 mg, 0.05 mmol) and TFA (11 mg, 0.10 mmol) in DCM (1.5 mL) was stirred at RT overnight. The volatiles were removed in vacuo and the residue was purified by prep-HPLC (Column: Xbridge Prep C18 10 um OBD, 19*250 mm; Mobile Phase: A: water (0.01% NH₃)+10 mm (NH₄HCO₃), B: acetonitrile; Gradient 32-62% B in 10 min) to give compound 3 (5.6 mg, yield 23%) as a yellow solid (free base): ¹H NMR (500 MHz, CDCl₃) δ (ppm) 8.83 (s, 1H), 8.26 (br s, 1H), 8.15 (d, J=9.2 Hz, 1H), 8.06 (d, J=2.8 Hz, 1H), 7.34 (dd, J=9.2 Hz and 2.8 Hz, 1H), 5.88 (m, 1H), 3.60-3.40 (m, 4H), 3.18-3.05 (m, 4H), 2.56 (s, 3H), 2.38 (s, 3H), 2.39-2.25 (m, 4H), 2.18-2.05 (m, 2H), 2.04-1.96 (m, 4H), 1.95-1.80 (m, 2H), 1.78-1.62 (m, 2H); ESI⁺ m/z 488.3 (M+1).

Example 4. Preparation of 6-acetyl-8-cyclopentyl-2-(5-(9,9-difluoro-3,7-diazabicyclo[3.3.1]nonan-3-yl)pyridin-2-ylamino)-5-methylpyrido[2,3-d]pyrimidin-7(8H)-one (Compound 4-1 and Compound 4-2)
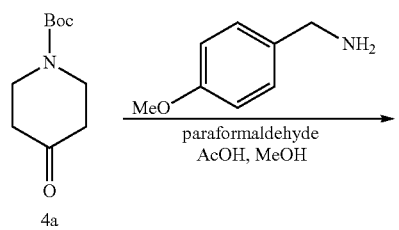
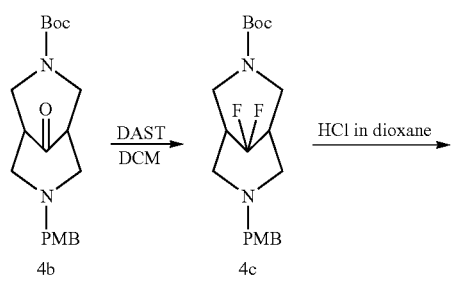
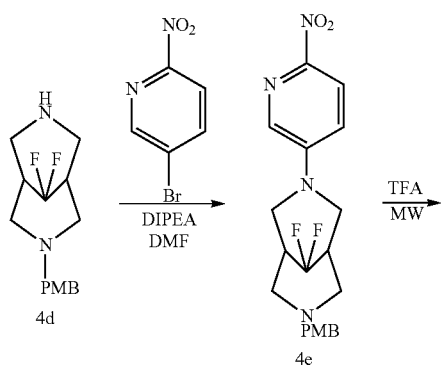
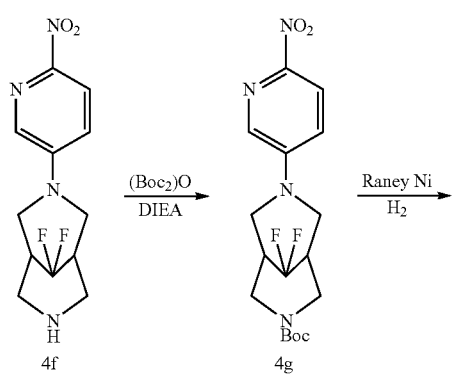
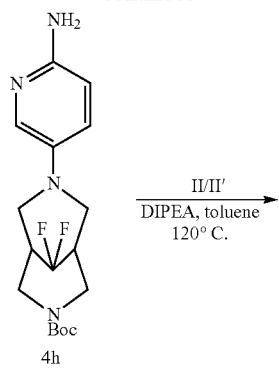
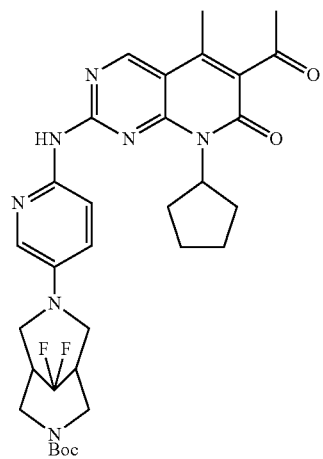
Compound 2

-continued

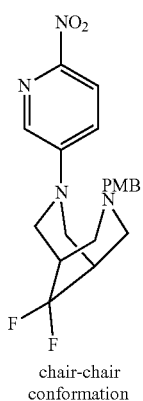
chair-chair conformation

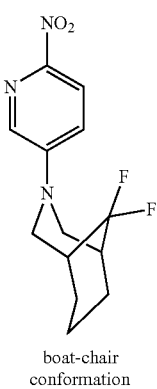
boat-chair conformation

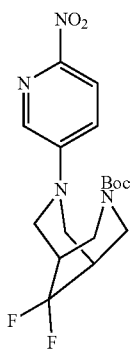

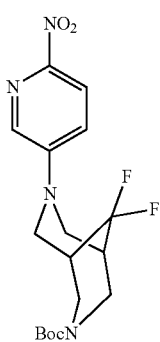

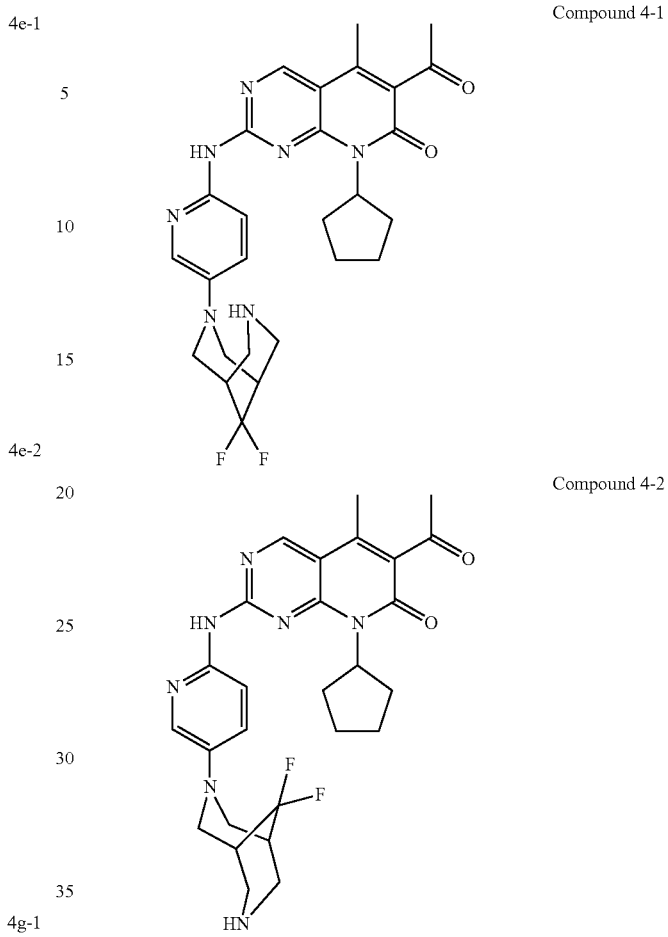

A solution of 1-Boc-4-piperidone (4a) (24 g, 120 mmol), 4-methoxybenzylamine (16.4 g, 120 mmol) and acetic acid (6.88 mL, 120 mmol) in methanol (120 mL) was added into a refluxed suspension of paraformaldehyde (8 g) in methanol (120 mL). The mixture was refluxed for 1 hour and another paraformaldehyde (8.0 g) was added. The reaction mixture was refluxed for 4 hours and was then cooled and concentrated. The residue was separated with ethyl acetate (200 mL) and sodium hydroxide (aq., 1 M, 160 mL). The aqueous solution was extracted with DCM (2×100 mL). The combined organic solution was dried ($Na_2SO_4$), filtered, and concentrated. The yellow residue was purified by silica gel column chromatography (PE/EtOAc=6:1) to give compound 4b (25 g, yield 58%) as yellow oil: $^1$H NMR (500 MHz, $CDCl_3$): δ 7.24 (d, J=8.4 Hz, 2H), 6.86 (d, J=8.9 Hz, 2H), 4.57 (d, J=13.2 Hz, 1H), 4.40 (d, J=13.3 Hz, 1H), 3.82 (s, 3H), 3.52 (d, J=13.4 Hz, 1H), 3.42 (d, J=13.1 Hz, 1H), 3.37 (d, J=13.5 Hz, 1H), 3.29 (d, J=13.4 Hz, 1H), 3.19 (d, J=12.5 Hz, 1H), 3.16 (d, J=12.9 Hz, 1H), 2.73 (dd, J=11.0, 3.4 Hz, 1H), 2.64 (dd, J=10.6, 2.8 Hz, 1H), 2.44 (d, J=17.3 Hz, 2H), 1.55 (s, 9H); ESI$^+$ m/z 361.1 (M+1).

A solution of compound 4b (25 g, 69 mmol) in DCM (50 mL) was slowly added DAST (27.8 g, 172.5 mmol) at 0° C. The mixture was then stirred at room temperature overnight and quenched with water (50 mL). The mixture was extracted with DCM (3×50 mL) and the combined organic solution was dried over $Na_2SO_4$ and concentrated. The yellow residue was purified by silica gel column chromatography (PE/EtOAc=50:1) to give compound 4c (2.3 g, yield 9%) as a yellow oil: ¹H NMR (400 MHz, CDCl₃) δ (ppm) 7.22 (d, J=8.8 Hz, 2H), 6.84 (d, J=8.8 Hz, 2H), 4.32 (d, J=12.0 Hz, 1H), 4.15 (d, J=12.8 Hz, 1H), 3.80 (s, 3H), 3.38 (s, 2H), 3.38-3.33 (m, 1H), 3.29-3.24 (m, 1H), 3.02-2.98 (m, 1H), 2.95-2.91 (m, 1H), 2.55-2.47 (m, 2H), 2.10-1.98 (m, 2H), 1.52 (s, 9H); ESI⁺ m/z 383.1 (M+1).

A mixture of 3-Boc-9,9-difluoro-7-(4-methoxybenzyl)-3,7-diazabicyclo[3.3.1]nonane (4c) (2.3 g, 6 mmol) and HCl in 1,4-dioxane (4 M, 15 mL, 60 mmol) was stirred at room temperature for 1 hour. The volatiles were removed in vacuo to give the crude product 4d (2.0 g, yield 93%) as a yellow solid: ESI⁺ m/z 283.0 (M+H)⁺.

A solution of 9,9-difluoro-3-(4-methoxybenzyl)-3,7-diazabicyclo[3.3.1]nonane hydrochloride (4d) (2.0 g, 5.6 mmol) in DMF (20 mL) was added DIPEA (4.6 mL, 28 mmol) and 5-bromo-2-nitropyridine (1.14 g, 5.6 mmol). The mixture was stirred at 100° C. overnight. After completion, the mixture was quenched with water (50 mL) and extracted with DCM (3×50 mL). The combined organic solution was concentrated in vacuo and the residue was purified by silica gel column chromatography (PE/EtOAc=50/1-5/1) to yield isomer-1 4e-1 (250 mg, yield 11%) and isomer-2 4e-2 (800 mg, yield 35%) as yellow oils. For 4e-1: ¹H NMR (400 MHz, CDCl₃) δ (ppm) 9.09 (d, J=2.8 Hz, 1H), 8.24 (dd, J=9.6 Hz and 2.8 Hz, 1H), 6.70-6.50 (m, 4H), 6.52 (d, J=9.6 Hz, 1H), 3.77 (s, 3H), 3.67-3.25 (m, 2H), 3.23 (s, 2H), 3.00-2.80 (m, 2H), 2.63-2.57 (m, 2H), 2.48-2.30 (m, 2H); ESI⁺ m/z 404.8 (M+1); For 4e-2: ¹H NMR (400 MHz, CDCl₃) δ (ppm) 8.22 (d, J=9.2 Hz, 1H), 8.06 (d, J=2.8 Hz, 1H), 7.07 (dd, J=9.2 Hz and 2.8 Hz, 1H), 6.86 (d, J=8.8 Hz, 2H), 6.68 (d, J=8.8 Hz, 2H), 3.95-3.90 (m, 2H), 3.75 (s, 3H), 3.67-3.60 (m, 2H), 3.34 (s, 2H), 2.96-2.92 (m, 2H), 2.65-2.60 (m, 2H), 2.45-2.35 (m, 2H); ESI⁺ m/z 404.8 (M+1).

The solution of 4e-1 (250 mg, 0.6 mmol) in TFA (4 mL) was heated in a microwave at 120° C. for 3 hours. After completion, the mixture was concentrated to give the crude compound 4f-1 (250 mg) as a brown oil. ESI⁺ m/z 284.9 (M+1).

The solution of 4e-2 (800 mg, 2 mmol) in TFA (4 mL) was heated in a microwave at 130° C. for 4 hours. After completion, the mixture was concentrated to give the crude compound 4f-2 (800 mg) as brown oil. ESI⁺ m/z 285.0 (M+1).

To the solution of 4f-1 (250 mg, 0.6 mmol) and DIPEA (232 mg, 1.8 mmol) in DCM (10 mL) was added Boc₂O (261 mg, 1.2 mmol) and DMAP (7 mg, 0.06 mmol), the mixture was stirred at rt for 1 h. After completion, the mixture was quenched with water (30 mL) and extracted with methylene chloride (3×30 mL). The combined organic solution was concentrated in vacuo and the residue was purified by silica gel column chromatography (PE/EtOAc=5/1) to yield the desired compounds 4g-1 (100 mg, yield 43%) as a yellow solid.

¹H NMR (400 MHz, CDCl₃) δ (ppm) 8.96 (d, J=2.8 Hz, 1H), 8.15 (dd, J=2.8, 9.2 Hz, 1H), 6.58 (d, J=9.6 Hz, 1H), 4.80-4.65 (m, 1H), 4.45-4.41 (m, 2H), 4.21-4.17 (m, 1H), 3.46-3.38 (m, 2H), 3.29-3.25 (m, 1H), 3.18-3.14 (m, 1H), 2.27-2.21 (m, 2H), 1.03 (s, 9H); ESI⁺ m/z 328.7 (M−Bu+1).

To the solution of 4f-2 (800 mg, 2.0 mmol) and DIPEA (774 mg, 6.0 mmol) in DCM (20 mL) was added Boc₂O (872 mg, 4.0 mmol) and DMAP (24 mg, 0.2 mmol), the mixture was stirred at rt for 1 h. After completion, the mixture was quenched with water (30 mL) and extracted with methylene chloride (3×30 mL). The combined organic solution was concentrated in vacuo and the residue was purified by silica gel column chromatography (PE/EtOAc=3/1) to yield the desired compounds 4g-2 (300 mg, yield 39%) as a yellow solid. ¹H NMR (400 MHz, CDCl₃) δ (ppm) 8.16 (d, J=9.6 Hz, 1H), 8.11 (d, J=3.2 Hz, 1H), 7.23 (dd, J=2.8, 9.2 Hz, 1H), 4.62-4.57 (m, 1H), 4.34-4.29 (m, 1H), 4.16-4.12 (m, 1H), 4.00-3.96 (m, 1H), 3.59-3.55 (m, 1H), 3.52-3.48 (m, 1H), 3.40-3.36 (m, 1H), 3.27-3.23 (m, 1H), 2.36 (m, 2H), 1.10 (s, 9H); ESI⁺ m/z 328.7 (M−Bu+1).

The mixture of 4g-1 (90 mg, 0.23 mmol) and Raney nickel (90 mg) in methanol (10 mL) was stirred under H₂ atmosphere at room temperature for 30 min. Then the reaction mixture was filtered, then concentrated. The residue was dissolved in DCM (20 mL), dried over Na₂SO₄ and concentrated in vacuo to give tert-butyl (1S,5R)-7-(6-aminopyridin-3-yl)-9,9-difluoro-3,7-diazabicyclo[3.3.1]nonane-3-carboxylate (4h-1, 70 mg, yield 87%) as a brown oil. ¹H NMR (400 MHz, CDCl₃) δ (ppm) 7.67 (s, 1H), 6.88 (d, J=8.0 Hz, 1H), 6.52 (d, J=8.4 Hz, 1H), 4.51-4.47 (m, 1H), 4.24-4.17 (m, 2H), 4.09-4.05 (m, 1H), 3.27-3.13 (m, 6H), 2.13 (br s, 2H), 1.06 (s, 9H); ESI⁺ m/z 355.0 (M+1).

The mixture of 4g-2 (60 mg, 0.16 mmol) and Raney nickel (60 mg) in methanol (10 mL) was stirred under H₂ atmosphere at room temperature for 10 min. Then the reaction mixture was filtered, then concentrated. The residue was dissolved in methylene chloride (20 mL), dried over Na₂SO₄ and concentrated in vacuo to give tert-butyl (1R,5S)-7-(6-aminopyridin-3-yl)-9,9-difluoro-3,7-diazabicyclo[3.3.1]nonane-3-carboxylate (4h-2, 30 mg, yield 53%) as a brown oil. ¹H NMR (400 MHz, CDCl₃) δ (ppm) 7.59 (s, 1H), 7.10 (d, J=8.8 Hz, 1H), 6.38 (d, J=8.8 Hz, 1H), 4.55-4.51 (m, 1H), 4.28-4.24 (m, 1H), 4.06 (s, 2H), 3.65-3.61 (m, 1H), 3.43-3.39 (m, 1H), 3.31-3.23 (m, 2H), 3.19-3.09 (m, 2H), 2.10 (br s, 2H), 1.16 (s, 9H); ESI⁺ m/z 355.0 (M+1).

A mixture of 4h-1 (70 mg, 0.20 mmol), DIPEA (26 mg, 0.20 mmol) and the mixture of II/II' (100 mg, ~0.29 mmol) in toluene (3 mL) was heated in a microwave at 130° C. for 3 hours. The volatiles were removed in vacuo and the residue was purified by prep-HPLC (Instrument PHG007; Column Xbridge Prep C18 10 um OBD, 19×250 mm; Mobile Phase A water (0.05% TFA), B acetonitrile; Gradient 55-65% B in 8.2 min, hold at 95% B for 4 min, stop at 12.3 min; Flow Rate (ml/min) 30; Detective Wavelength (nm) 214/254) to give the title compound 4i-1 (20 mg, 16% yield) as a yellow solid. ¹H NMR (400 MHz, CDCl₃) δ (ppm) 8.63 (s, 2H), 7.89 (m, 1H), 6.91 (d, J=9.2 Hz, 1H), 5.76-5.71 (m, 1H), 4.58-4.46 (m, 2H), 4.37-4.25 (m, 2H), 3.61-3.53 (m, 2H), 3.39-3.24 (m, 2H), 2.54 (s, 3H), 2.34-2.24 (m, 5H), 2.23-2.17 (m, 2H), 1.99-1.91 (m, 2H), 1.88-1.81 (m, 2H), 1.68-1.63 (m, 2H), 1.16 (s, 9H); ESI⁺ m/z 624.0 (M+1).

A mixture of 4h-2 (30 mg, 0.085 mmol), DIPEA (11 mg, 0.085 mmol) and the mixture of II/II' (54 mg, ~0.16 mmol) in toluene (3 mL) was heated in a microwave at 130° C. for 7 hours. The volatiles were removed in vacuo and the residue was purified by prep-HPLC (same conditions as for 4i-1) to give the title compound 4i-2 (15 mg, yield 28%) as a yellow solid. ¹H NMR (400 MHz, CDCl₃) δ (ppm) 9.10 (s, 1H), 8.15 (dd, J=2.8, 9.6 Hz, 1H), 7.82 (d, J=2.4 Hz, 1H), 7.54 (d, J=9.6 Hz, 1H), 6.05-5.95 (m, 1H), 4.56-4.52 (m, 1H), 4.43-4.39 (m, 1H), 4.10-4.06 (m, 1H), 3.90-3.86 (m, 1H), 3.41-3.37 (m, 3H), 3.30-3.25 (m, 1H), 2.50 (s, 3H), 2.43 (s, 3H), 2.40-2.34 (m, 2H), 2.34-2.26 (m, 2H), 2.11-2.05 (m, 2H), 1.92-1.86 (m, 2H), 1.71-1.67 (m, 2H), 1.33-1.28 (m, 2H), 1.20 (s, 9H); ESI⁺ m/z 623.7 (M+1).

A mixture of compound 4i-1 (20 mg, 32 umol) and HCl (in dioxane, 4M, 1 mL, 4 mmol) in methylene chloride (2 mL) was stirred at room temperature for 3 h. The volatiles were removed in vacuo and the residue was purified by prep-HPLC (Instrument PHG016; Column Xbridge Prep C18 10 um OBD, 19×250 mm; Mobile Phase A water (0.01% NH$_3$)+10 mm (NH$_4$HCO$_3$), B acetonitrile; Gradient 32-62% B in 10 min; Flow Rate (ml/min) 30; Detective Wavelength (nm) 214/254) to give compound 4-1 (13 mg, 79% yield) as a yellow solid (free base): $^1$H NMR (500 MHz, CDCl$_3$) δ (ppm) 8.71 (s, 1H), 8.31 (d, J=2.4 Hz, 1H), 7.82 (dd, J=2.0, 8.8 Hz, 1H), 7.23 (br s, 1H), 6.72 (d, J=9.2 Hz, 1H), 5.82-5.77 (m, 1H), 4.34-4.30 (m, 2H), 3.46-3.42 (m, 2H), 3.31-3.23 (m, 4H), 2.54 (s, 3H), 2.35 (s, 3H), 2.33-2.23 (m, 2H), 2.22-2.17 (m, 2H), 2.03-1.90 (m, 5H), 1.61 (m, 2H); ESI$^+$ m/z 524.1 (M+1).

A mixture of compound 4i-2 (15 mg, 24 umol) and HCl (in dioxane, 4 M, 1 mL, 4 mmol) in DCM (2 mL) was stirred at RT for 3 h. The volatiles were removed in vacuo and the residue was purified by prep-HPLC (same conditions as for 4-1) to give compound 4-2 (9 mg, yield 71%) as a yellow solid (free base): $^1$H NMR (400 MHz, CDCl$_3$) δ (ppm) 8.83 (s, 1H), 8.30-8.19 (m, 2H), 8.06 (s, 1H), 7.37-7.26 (m, 1H), 5.91-5.86 (m, 1H), 3.78-3.74 (m, 2H), 3.45-3.42 (m, 2H), 3.41-3.31 (m, 4H), 2.55 (s, 3H), 2.38-2.33 (m, 5H), 2.28-2.21 (m, 2H), 2.08-2.04 (m, 3H), 1.91-1.88 (m, 2H), 1.73-1.69 (m, 2H); ESI$^+$ m/z 524.0 (M+1).

Example 5: Preparation of 2-(5-(3,9-diazaspiro[5.5]undecan-3-yl)pyridin-2-ylamino)-6-acetyl-8-cyclopentyl-5-methylpyrido[2,3-d]pyrimidin-7(8H)-one (Compound 5)

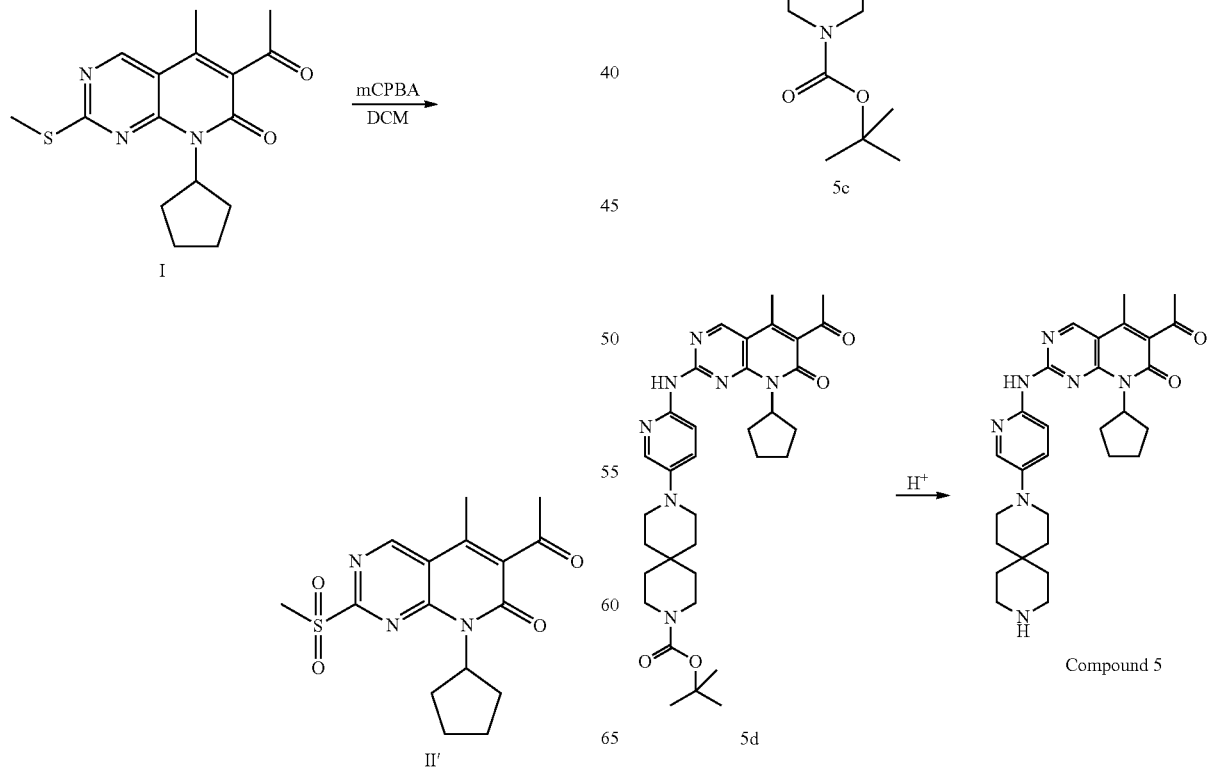

Example 6: Preparation of 2-(5-(2,9-diazaspiro[5.5]undecan-2-yl)pyridin-2-ylamino)-6-acetyl-8-cyclopentyl-5-methylpyrido[2,3-d]pyrimidin-7(8H)-one (Compound 6)

Compound 6 was synthesized using the same method as described for preparation of compound 5:

Example 7: Preparation of (R,S)-2-(1,2,3,4,4a,5-hexahydro-pyrazino[2,1-c][1,4]benzoxazine-8-amino)-6-acetyl-8-cyclopentyl-5-methylpyrido[2,3-d]pyrimidin-7(8H)-one (Compounds 7); (R)-2-(1,2,3,4,4a,5-hexahydro-pyrazino[2,1-c][1,4]benzoxazine-8-amino)-6-acetyl-8-cyclopentyl-5-methylpyrido[2,3-d]pyrimidin-7(8H)-one (Compound 7R); and (S)-2-(1,2,3,4,4a,5-hexahydro-pyrazino[2,1-c][1,4]benzoxazine-8-amino)-6-acetyl-8-cyclopentyl-5-methylpyrido[2,3-d]pyrimidin-7(8H)-one (Compound 7S)

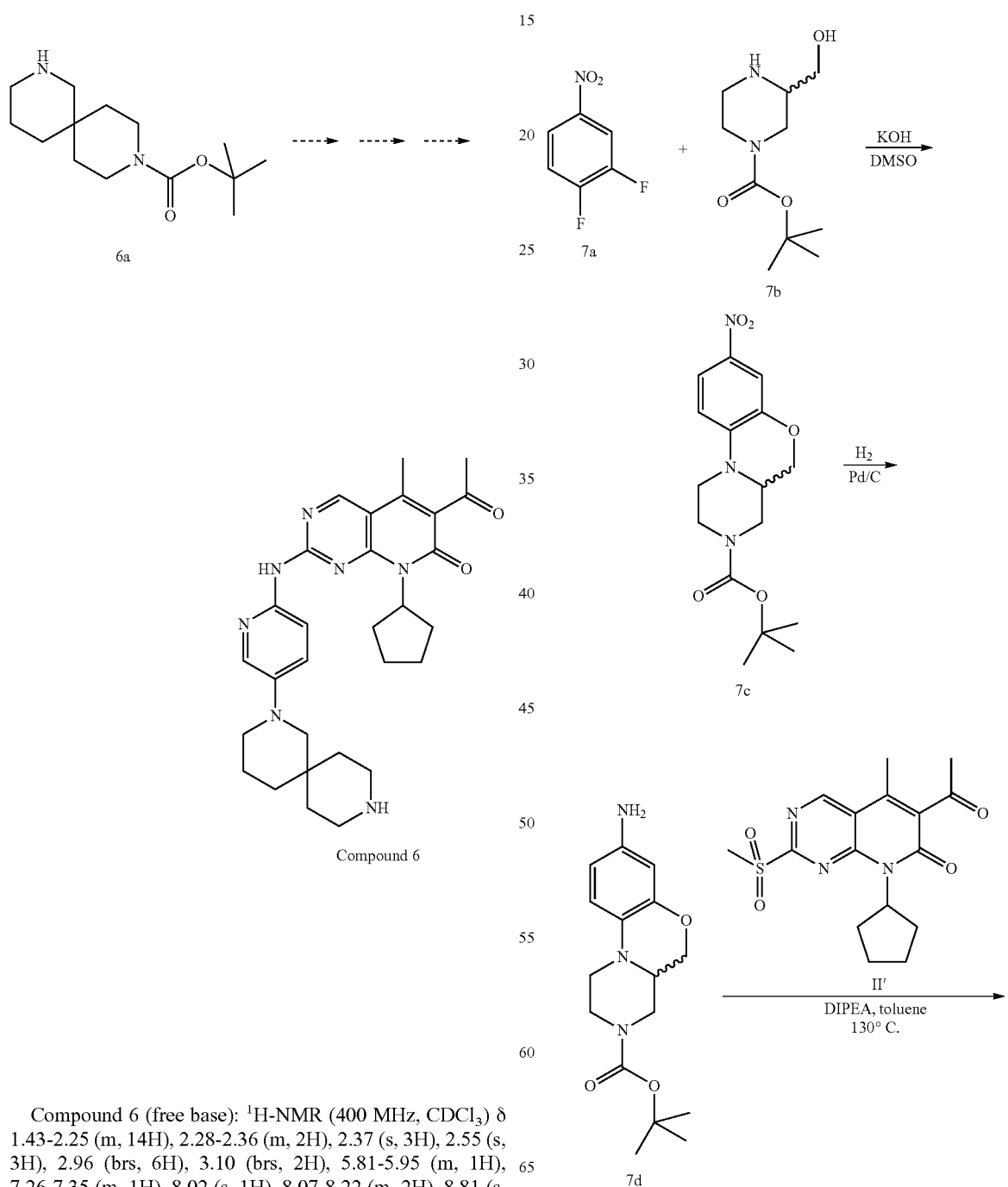

Compound 6 (free base): $^1$H-NMR (400 MHz, CDCl$_3$) δ 1.43-2.25 (m, 14H), 2.28-2.36 (m, 2H), 2.37 (s, 3H), 2.55 (s, 3H), 2.96 (brs, 6H), 3.10 (brs, 2H), 5.81-5.95 (m, 1H), 7.26-7.35 (m, 1H), 8.02 (s, 1H), 8.07-8.22 (m, 2H), 8.81 (s, 1H). LC-MS 516.3 (M+H)$^+$.

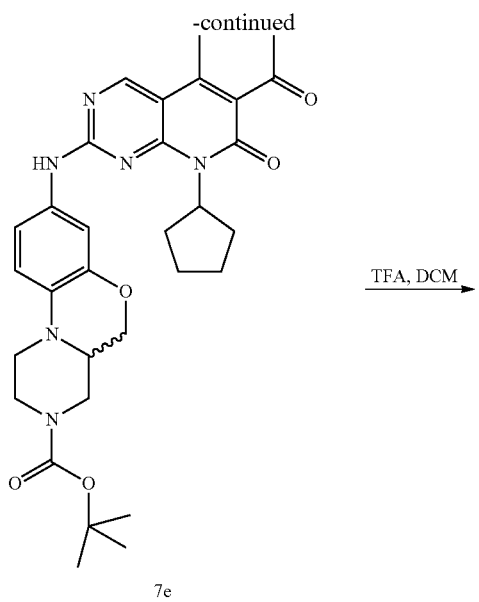

7e

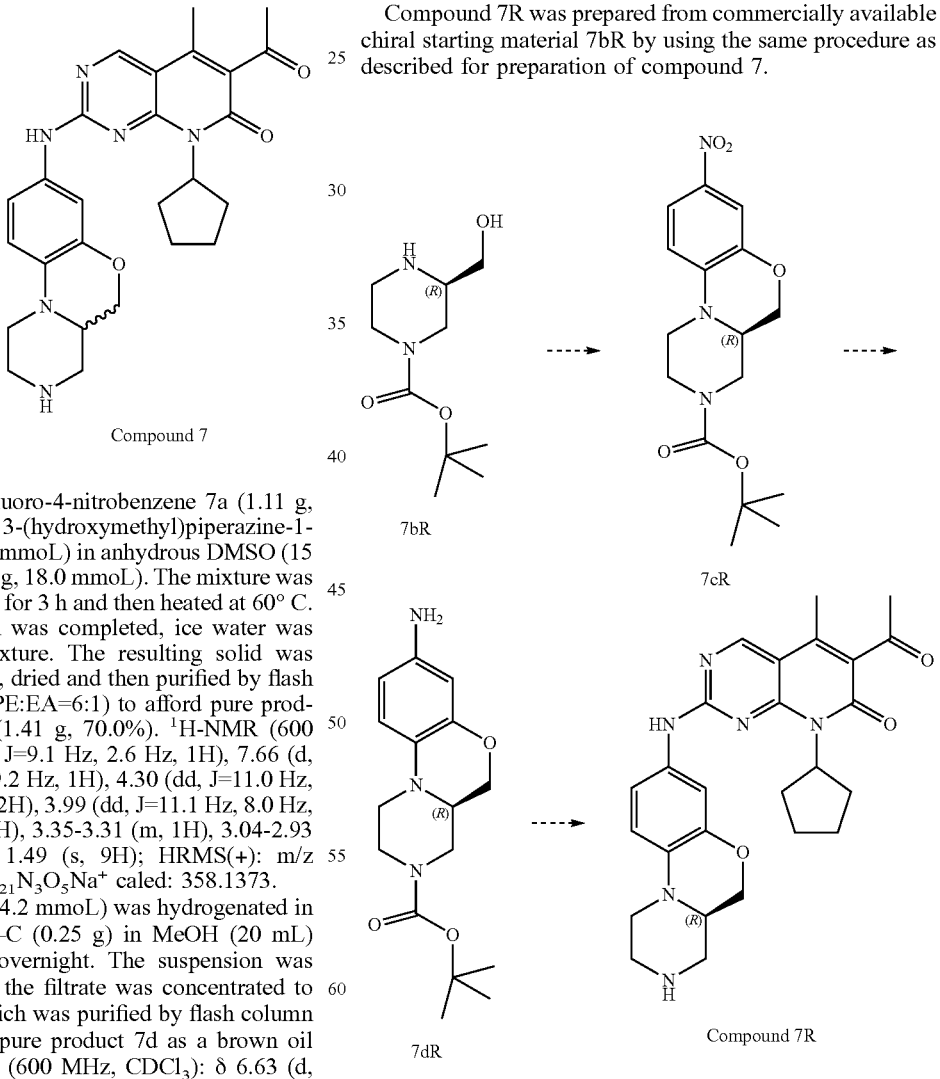

To a solution of compound 7d (60 mg, 0.20 mmol) in toluene (1 mL) was added DIPEA (29.6 mg, 0.23 mmol) and compound II' (40 mg, 0.11 mmol). After the addition, the reaction was stirred at RT for 3 hours. The reaction was diluted with $CH_2Cl_2$ (50 mL), and the organic phase was washed with water (5 mL×2), followed by brine (5 mL×1). The organic layer was dried ($Na_2SO_4$), filtered, and concentrated. The residue was purified by Combi-Flash (12 g silica gel, eluting with 0% to 60% of EtOAc in petroleum ether) to afford compound 7e (25 mg, yield 38%) as a yellow solid. LC-MS: 575 $(M+1)^+$.

To a solution of compound 7e (22 mg, 0.038 mmol) in DMC (8 mL) was added TFA (1 mL). The mixture was stirred at RT for 1 hour. The reaction was concentrated and the residue was purified by PREP-HPLC to afford compound 7 (9 mg, yield 49%) as a yellow solid (free base). $^1$H-NMR (400 MHz, $CDCl_3$) δ 1.53-1.63 (m, 2H), 1.77-1.86 (m, 2H), 1.88-1.94 (m, 2H), 2.19-2.27 (m, 2H), 2.28 (s, 3H), 2.44-2.51 (m, 1H), 2.50 (s, 3H), 2.62 (t, 1H), 2.85-3.02 (m, 3H), 3.12 (d, 1H), 3.58 (d, 1H), 3.94 (t, 1H), 4.11 (d, 1H), 5.72-5.85 (m, 1H), 6.70 (d, 1H), 6.90 (d, 1H), 7.05 (br, s, 2H), 8.63 (s, 1H). LC-MS: 475 $(M+H)^+$.

Compound 7R was prepared from commercially available chiral starting material 7bR by using the same procedure as described for preparation of compound 7.

To a solution of 1,2-difluoro-4-nitrobenzene 7a (1.11 g, 7.0 mmoL) and tert-butyl 3-(hydroxymethyl)piperazine-1-carboxylate 7b (1.30 g, 6.0 mmoL) in anhydrous DMSO (15 mL) was added KOH (1.01 g, 18.0 mmoL). The mixture was stirred at room temperature for 3 h and then heated at 60° C. for 8 h. After the reaction was completed, ice water was added to the reaction mixture. The resulting solid was filtered, washed with water, dried and then purified by flash column chromatography (PE:EA=6:1) to afford pure product 7c as a yellow solid (1.41 g, 70.0%). $^1$H-NMR (600 MHz, $CDCl_3$): δ 7.79 (dd, J=9.1 Hz, 2.6 Hz, 1H), 7.66 (d, J=2.6 Hz, 1H), 6.76 (d, J=9.2 Hz, 1H), 4.30 (dd, J=11.0 Hz, 3.0 Hz, 1H), 4.18-4.09 (m, 2H), 3.99 (dd, J=11.1 Hz, 8.0 Hz, 1H), 3.79 (d, J=11.0 Hz, 1H), 3.35-3.31 (m, 1H), 3.04-2.93 (m, 2H), 2.67 (br, 1H), 1.49 (s, 9H); HRMS(+): m/z 358.1370 ($[M+Na]^+$, $C_{16}H_{21}N_3O_5Na^+$ calcd: 358.1373.

Intermediate 7c (1.41 g, 4.2 mmoL) was hydrogenated in the presence of 10% Pd—C (0.25 g) in MeOH (20 mL) under hydrogen (1 atm) overnight. The suspension was filtered through celite and the filtrate was concentrated to give the crude product, which was purified by flash column chromatography to afford pure product 7d as a brown oil (1.09 g, 85.0%). $^1$H-NMR (600 MHz, $CDCl_3$): δ 6.63 (d, J=8.5 Hz, 1H), 6.26 (dd, J=8.3 Hz, 1.8 Hz, 1H), 6.22 (d, J=2.3 Hz, 1H), 4.18-4.16 (m, 2H), 3.98-3.94 (m, 2H), 3.56 (d, J=10.3 Hz, 1H), 3.04-2.93 (m, 2H), 2.62-2.58 (m, 3H), 1.48 (s, 9H).

Compound 7R (free base): $^1$H NMR ($CDCl_3$, 400 Hz): δ 8.70 (s, 1H), 7.14 (br, s, 1H), 7.12 (d, J=2.8 Hz, 1H), 6.96 (dd, J=8.8 Hz, 2.4 Hz, 1H), 6.76 (d, J=8.8 Hz, 1H), 5.90-5.80

(m, 1H), 4.19 (dd, J=10.4 Hz, 2.4 Hz, 1H), 4.01 (dd, J=10.4 Hz, 8.8 Hz, 1H), 3.64 (d, J=11.6 Hz, 1H), 3.18 (d, J=12.4 Hz, 1H), 3.10-2.96 (m, 3H), 2.70 (td, J=11.6 Hz, 3.2 Hz, 1H), 2.57-2.52 (m, 1H), 2.54 (s, 3H), 2.35 (s, 3H), 2.35-2.29 (m, 2H), 1.98-1.90 (m, 2H), 1.88-1.80 (m, 2H), 1.66-1.58 (m, 2H); MS (ESI): 475.3 (M+H)$^+$; e.e.>95%.

Compound 7S was prepared from commercially available chiral starting material 7bS by using the same procedure as described for preparation of compound 7.

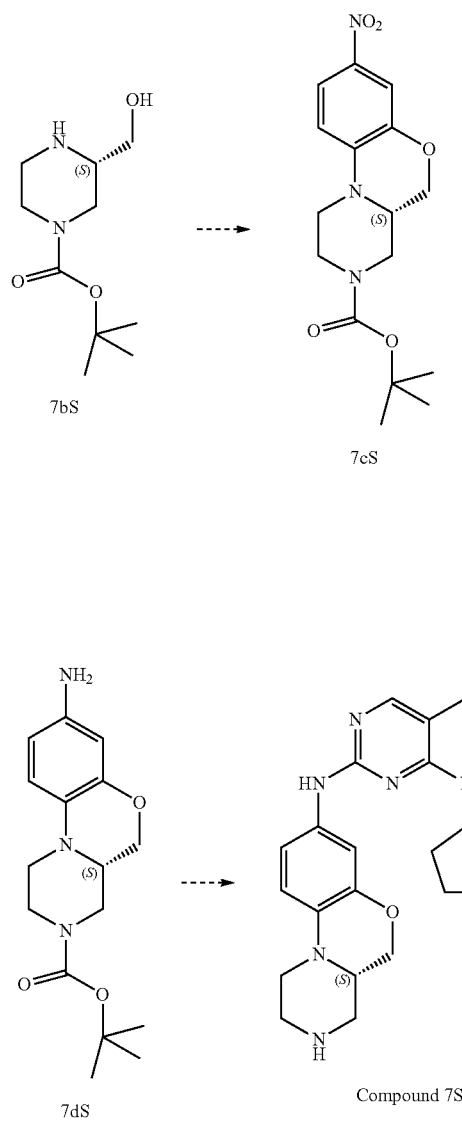

Example 8: Preparation of 6-acetyl-8-cyclopentyl-5-methyl-2-(5,6,7,8-tetrahydro-1,6-naphthyridin-2-ylamino)pyrido[2,3-d]pyrimidin-7(8H)-one (Compound 8)

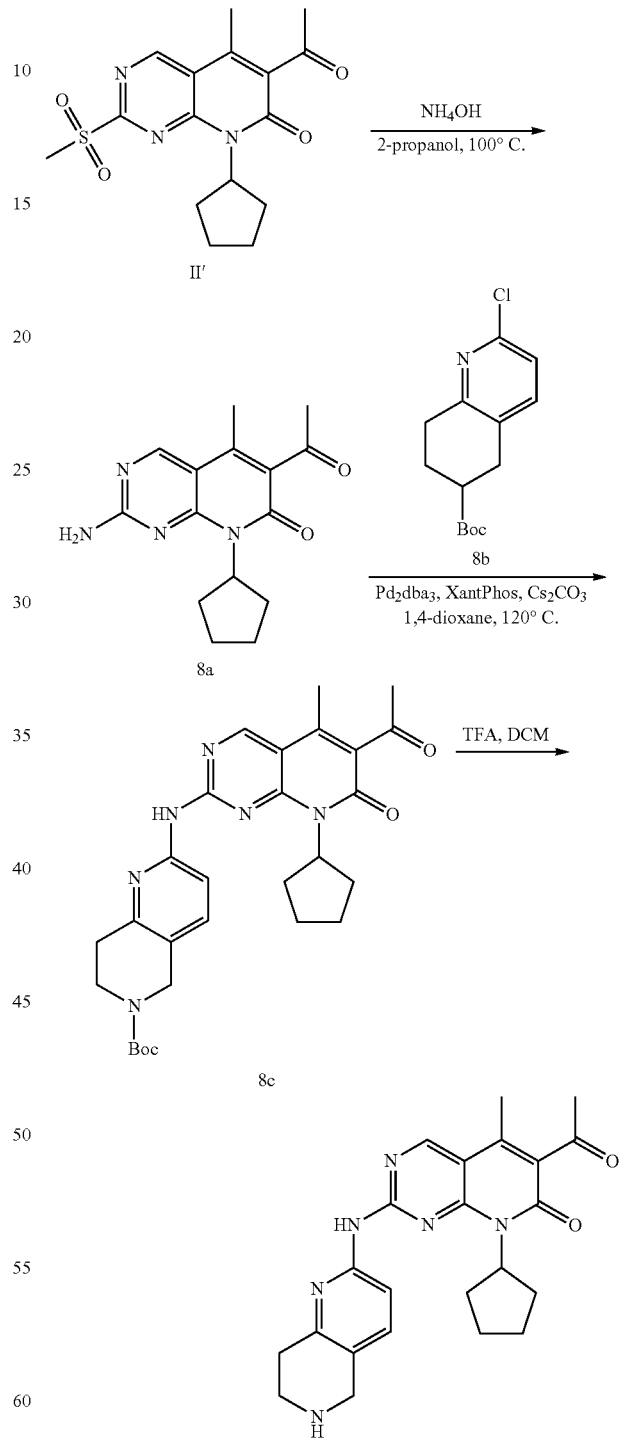

Compound 7S (free base): $^1$H NMR (CDCl$_3$, 400 Hz): δ 8.71 (s, 1H), 7.12 (br, s, 1H), 7.12 (d, J=2.4 Hz, 1H), 6.96 (dd, J=8.8 Hz, 2.4 Hz, 1H), 6.77 (d, J=8.8 Hz, 1H), 5.90-5.80 (m, 1H), 4.19 (dd, J=10.4 Hz, 2.8 Hz, 1H), 4.01 (dd, J=10.4 Hz, 9.2 Hz, 1H), 3.64 (d, J=11.2 Hz, 1H), 3.18 (d, J=12.4 Hz, 1H), 3.11-2.96 (m, 3H), 2.70 (td, J=11.6 Hz, 3.2 Hz, 1H), 2.57-2.52 (m, 1H), 2.54 (s, 3H), 2.35 (s, 3H), 2.35-2.27 (m, 2H), 1.98-1.90 (m, 2H), 1.88-1.80 (m, 2H), 1.66-1.58 (m, 2H); MS (ESI): 475.3 (M+H)$^+$; e.e.>90%.

A mixture of compound II' (450 mg, 1.3 mmol), isopropyl alcohol (2.5 mL) and ammonium hydroxide (2.5 mL) was heated at 100° C. for 2 h. The mixture was concentrated and the residue was purified by Combi-Flash (20 g silica gel, eluting with MeOH in DCM from 0% to 10%) to afford 290 mg of the title compound 8a (78.6% yield) as a white solid. LC-MS: 287 (M+H)⁺.

To a 50 mL flask was added compound 8a (290 mg, 1 mmol), tert-butyl 2-chloro-7,8-dihydro-1,6-naphthyridine-6(5H)-carboxylate (8b, 573 mg, 2 mmol), cesium carbonate (500 mg, 1.5 mmol), 1,4-dioxane (8 mL), Pd$_2$dba$_3$ (185.5 mg, 0.20 mmol), 4,5-Bis(diphenylphosphino)-9,9-dimethyl-xanthene (58.6 mg, 0.10 mmol). The reaction vessel was purged 3 times with nitrogen, and then the mixture was stirred at 120° C. overnight. The reaction was poured into 20 mL water, extracted with EA (50 mL×3). The combined organic phase was washed with brine, dried over Na$_2$SO$_4$, filtered and concentrated. The residue was purified by Combi-Flash (20 g silica gel, eluting with EtOAc in PE from 0% to 60%) to afford 290 mg of the compound 8c (55% yield) as a white solid. LC-MS: 519 (M+H)⁺. A solution of compound 4 (290 mg, 0.56 mmol) in dichloromethane (5 mL) was added trifluoroacetic acid (1 mL). The mixture was stirred at RT for 1 h. The mixture was concentrated and the residue was purified by Combi-Flash (20 g silica gel, eluting with 7N NH$_3$-MeOH in DCM from 0% to 10%) to afford 220 mg of compound 8 (94% yield) as a light yellow solid (free base). $^1$H-NMR (400 MHz, CDCl$_3$) δ 1.66-1.58 (m, 2H), 1.78-1.82 (m, 2H), 1.98-2.01 (m, 2H), 2.26-2.31 (m, 2H), 2.32 (s, 3H), 2.47 (s, 3H), 2.82 (t, 2H), 3.19 (t, 2H), 3.96 (s, 2H), 5.74-5.84 (m, 1H), 7.32 (d, 1H), 7.93 (s, 1H), 8.02 (d, 1H), 8.75 (s, 1H); LC-MS: 419 (M+H)⁺.

Example 12: Preparation of 8-(4-(6-(6-acetyl-8-cyclopentyl-5-methyl-7-oxo-7,8-dihydropyrido[2,3-d]pyrimidin-2-ylamino)pyridin-3-yl)piperazin-1-yl)-N-hydroxy-8-oxooctanamide (Compound 12)

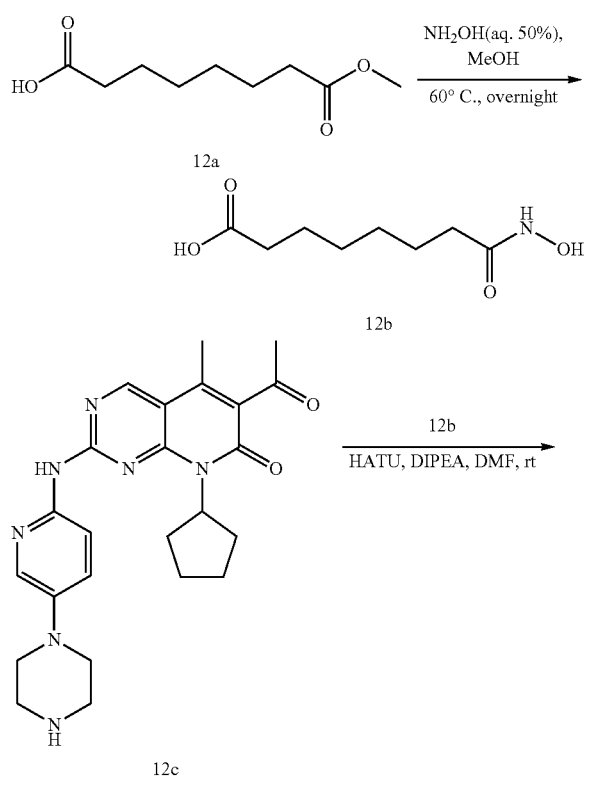

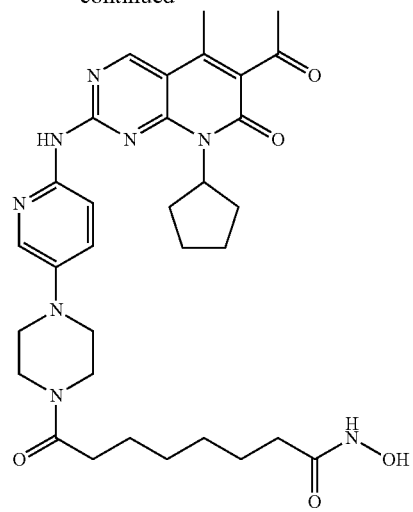

Compound 12

To a solution of 8-methoxy-8-oxooctanoic acid 12a (170 mg, 0.899 mmol) in MeOH (2 mL) was added NH$_2$OH (50% in water, 1.5 mL). The reaction was stirred at 60° C. overnight. The mixture was concentrated in vacuo and the residue was stirred in MeOH (1 mL). The resulting mixture was filtered and the solid was dried in vacuo to afford 12b (110 mg, yield 64%) as a white solid.

A mixture of 12b (17 mg, 0.089 mmole), 12c (20 mg, 0.045 mmole, prepared according to *J. Med. Chem.* 2005, 48(7), 2388-2406), HATU (38 mg, 0.099 mmole) and DIPEA (25 mg, 0.198 mmole) in DMF (3 mL) was stirred at RT overnight. The mixture was directly purified by prep-HPLC (Sunfire™Prep C18 column, 10 um×19×150 mm; Mobile A: H$_2$O (0.1% HCOOH); Mobile B: ACN; Flow Rate (ml/min): 25) to afford Compound 12 (12.8 mg, yield 46%) as a yellow solid. $^1$H NMR (DMSO-d$_6$, 400 Hz): δ 10.34 (s, 1H), 10.17 (s, 1H), 8.96 (s, 1H), 8.67 (s, 1H), 8.08 (d, J=3.2 Hz, 1H), 7.89 (d, J=8.8 Hz, 1H), 7.51 (dd, J=8.8 Hz, 3.2 Hz, 1H), 5.88-5.77 (m, 1H), 3.61 (br, s, 4H), 3.16-3.11 (m, 4H), 2.42 (s, 3H), 2.35 (t, J=7.2 Hz, 2H), 2.31 (s, 3H), 2.27-2.21 (m, 2H), 1.95-1.88 (m, 4H), 1.80-1.74 (m, 2H), 1.60-1.57 (m, 2H), 1.52-1.44 (m, 4H), 1.30-1.24 (m, 4H); MS (ESI): 619.3 (M+H)⁺.

Example 13: Preparation of 5-(4-(6-(6-acetyl-8-cyclopentyl-5-methyl-7-oxo-7,8-dihydropyrido[2,3-d]pyrimidin-2-ylamino)pyridin-3-yl)piperazin-1-yl)-N-hydroxy-5-oxopentanamide (Compound 13)

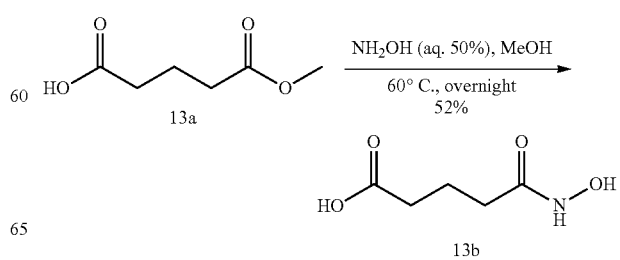

53
-continued

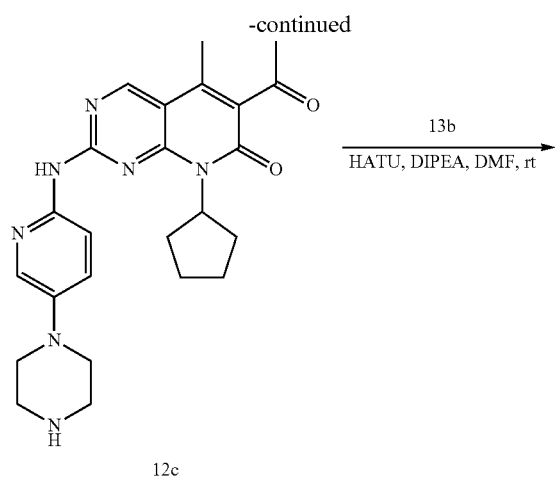

12c

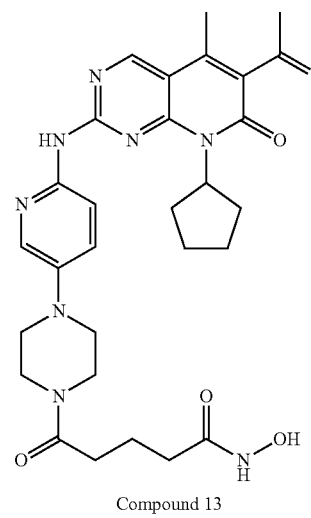

Compound 13

54

Example 14: Preparation of 7-(4-(6-(6-acetyl-8-cyclopentyl-5-methyl-7-oxo-7,8-dihydropyrido[2,3-d]pyrimidin-2-ylamino)pyridin-3-yl)piperazin-1-yl)-N-hydroxyheptanamide (Compound 14)

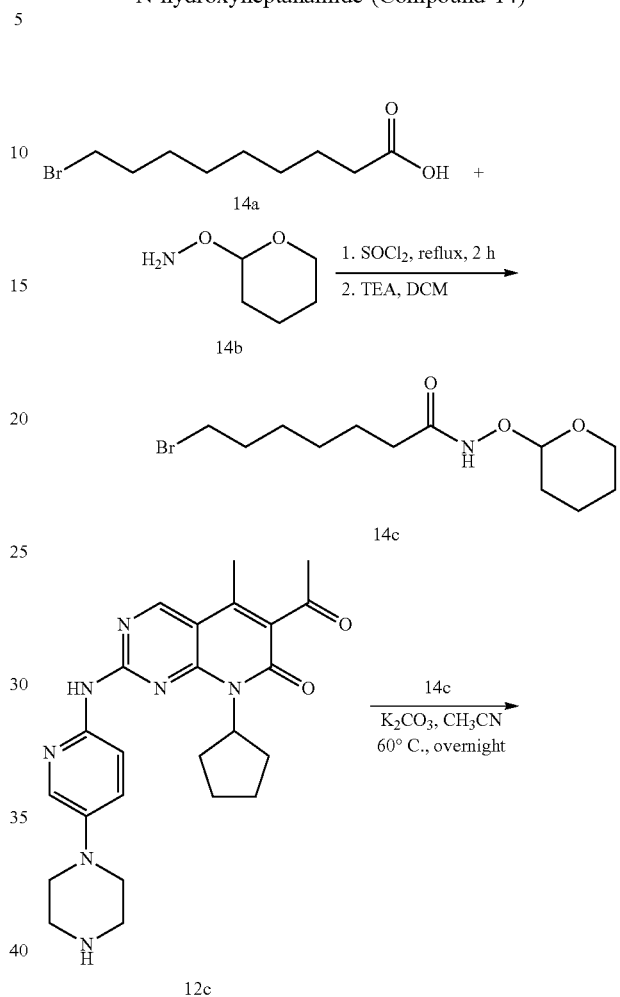

To a solution of 5-methoxy-5-oxopentanoic acid (13a, 300 mg, 2.055 mmol) in MeOH (2 mL) was added NH$_2$OH (50% in water, 1 mL). This reaction was stirred overnight at 60° C. The mixture was concentrated in vacuo, the residue was washed with EtOAc (1 mL) and the obtained colorless oil was concentrated in vacuo to afford the crude product 13b (160 mg, yield 52%) as a colorless oil, which was used for next step without further purification. MS: 148.1 [M+H]$^+$.

To a mixture of compound 13b (39 mg, 0.268 mmol), compound 12c (30 mg, 0.067 mmol) and DIPEA (43 mg, 0.335 mmol) in DMF (1 mL) were added HATU (26 mg, 0.067 mmol) at room temperature. The reaction mixture was stirred at room temperature overnight. The mixture was purified by prep-HPLC (conditions as described in Example 12) to afford Compound 13 as a yellow solid (6 mg, yield 16%). $^1$H NMR (DMSO-d$_6$, 400 Hz): δ 10.15 (s, 1H), 8.95 (s, 1H), 8.44 (s, 1H), 8.08 (s, 1H), 7.88-7.85 (m, 1H), 7.50 (d, J=8.8 Hz, 1H), 6.68 (br, 1H), 5.85-5.81 (m, 1H), 3.60-3.02 (m, 8H), 2.42 (s, 3H), 2.37-2.24 (m, 7H), 1.89-1.88 (m, 2H), 1.77-1.71 (m, 4H), 1.65-1.50 (m, 4H); MS: 577.3 [M+H]$^+$.

-continued

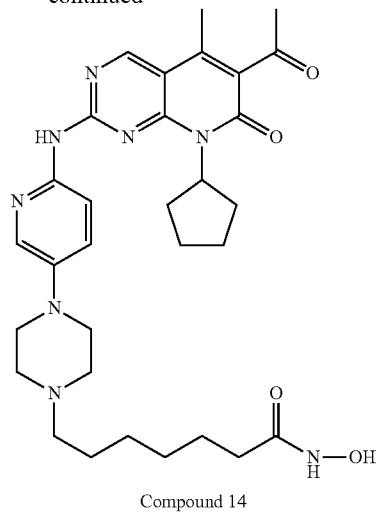

Compound 14

7-Bromoheptanoic acid (14a, 500 mg, 2.392 mmol) was dissolved in SOCl₂ (2 mL), and this solution was stirred at reflux for 2 h. Then the solution was concentrated in vacuo. The residue was dissolved in CH₂Cl₂ (10 mL), then the mixture of O-(tetrahydro-2H-pyran-2-yl)hydroxylamine (14b, 280 mg, 2.932 mmol) and TEA (483 mg, 4.784 mmol) in DCM (6 mL) was added dropwise at 0° C. The resulting reaction mixture was stirred for 2 h at room temperature. The mixture was purified by column chromatography on silica gel (petroleum ether/EtOAc=2/1) to afford the product 14c (260 mg, yield 35%) as a white solid. MS: 224.0 [M−84+H]⁺.

A mixture of compound 12c (45 mg, 0.101 mmol), compound 14c (43 mg, 0.141 mmol) and K₂CO₃ (21 mg, 0.152 mmol) in CH₃CN (1.5 mL) was stirred overnight at 60° C. The mixture was cooled to room temperature and filtered, and the filtrate was concentrated to dryness. The resulting residue was purified by Prep-TLC (DCM/MeOH=10/1) to afford the product 14d (50 mg, yield 67%) as a yellow solid. MS: 675.4 [M+H]⁺.

To a solution of compound 14d (40 mg, 0.059 mmol) in anhydrous THF (2 mL) was added a solution of HCl in 1,4-dioxane (4 M, 0.1 mL, 0.394 mmol) at 0° C. The reaction was stirred for 1.5 h at 0° C. This mixture was concentrated in vacuo at RT, and the residue was purified by Prep-HPLC (conditions as described in Example 12) to afford the product Compound 14 (10.25 mg, yield: 29%) as a yellow solid. ¹H NMR (DMSO-d₆, 400 Hz): δ 10.33 (s, 1H), 10.11 (s, 1H), 8.95 (s, 1H), 8.66 (s, 1H), 8.04 (d, J=3.2 Hz, 1H), 7.84 (d, J=9.6 Hz, 1H), 7.46 (dd, J=9.2 Hz, J=3.2 Hz, 1H), 5.86-5.78 (m, 1H), 3.54-3.45 (m, 4H), 3.17-3.14 (m, 4H), 2.42 (s, 3H), 2.33-2.18 (m, 4H), 2.28 (s, 3H), 1.94 (t, J=7.2 Hz, 2H), 1.91-1.83 (m, 2H), 1.80-1.73 (m, 2H), 1.60-1.55 (m, 2H), 1.52-1.41 (m, 4H), 1.29-1.26 (m, 4H); MS: 591.3 [M+H]⁺.

Example 15: Preparation of 8-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-hydroxyoctanamide (Compound 15)

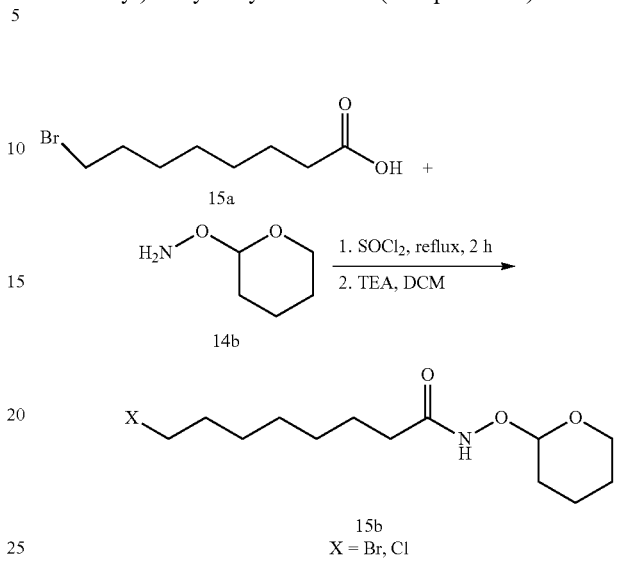

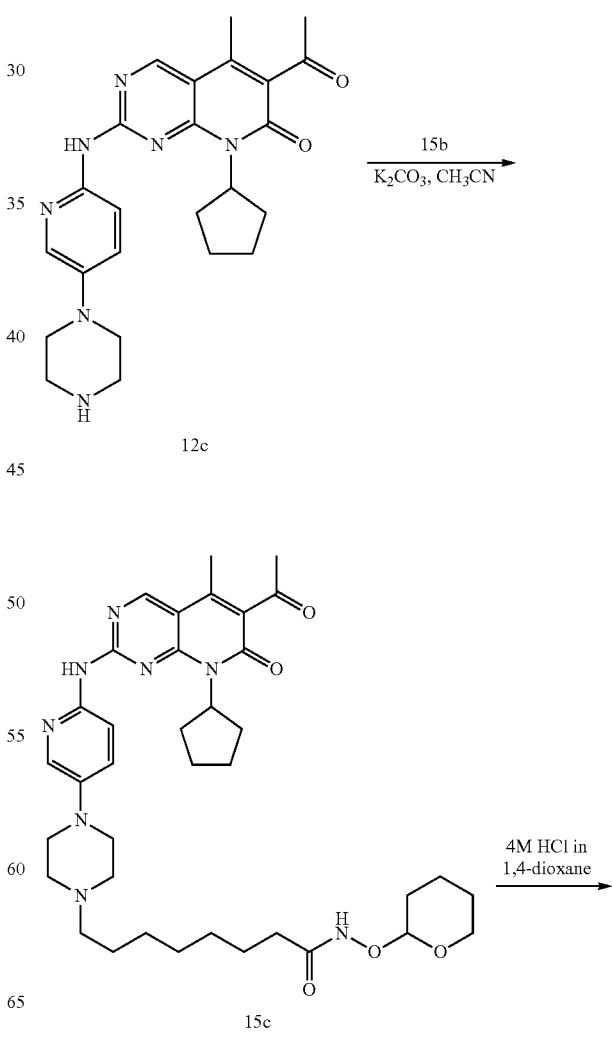

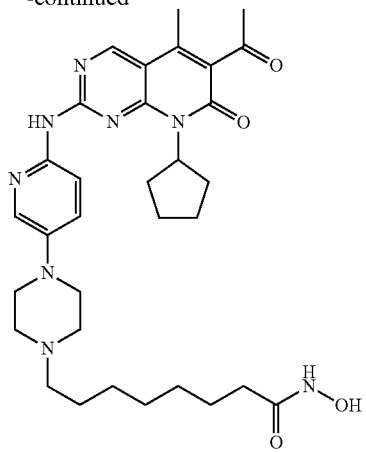

Compound 15

8-bromooctanoic acid (15a, 515 mg, 2.31 mmol) was dissolved in SOCl$_2$ (2 mL), and this solution was stirred at reflux for 2 h. Then the solution was concentrated in vacuo. The residue was dissolved in CHCl$_2$ (10 mL), then the mixture of O-(tetrahydro-2H-pyran-2-yl)hydroxylamine (14b, 406 mg, 3.46 mmol) and TEA (467 mg, 4.62 mmol) in CH$_2$Cl$_2$ (8 mL) was added dropwise at 0° C. The resulting reaction mixture was stirred for 16 h at room temperature. The mixture was concentrated in vacuo and the residue was purified by column chromatography on silica gel (petroleum ether/EtOAc=2/1) to afford the product 15b (400 mg, yield 59%) as a white solid. MS: 322.0 [M+H]$^+$, 324.0 [M+H]$^+$.

A mixture of compound 12c (45 mg, 0.10 mmol), compound 15b (90 mg, 0.30 mmol), KI (5 mg) and K$_2$CO$_3$ (42 mg, 0.30 mmol) in DMF (1.5 mL) was stirred for 16 h at 80° C. The mixture was cooled to room temperature and filtered, and the filtrate was diluted with water (4 mL), extracted with ethyl acetate (5 mL×3). The combined organic phase was washed with brine (5 mL), dried over anhydrous sodium sulfate, filtered, and concentrated to dryness. The resulting residue was purified by Prep-TLC (CH$_2$Cl$_2$/MeOH=15/1) to afford the product 15c (40 mg, yield 68%) as a yellow solid. MS: 689.4 [M+H]$^+$.

To a solution of compound 15c (30 mg, 0.044 mmol) in dichloromethane (1 mL) was added a solution of 4M HCl in 1, 4-dioxane (0.5 mL) at 0° C. The reaction was stirred for 3 h at room temperature. This mixture was concentrated in vacuo at room temperature, and the residue was purified by Prep-HPLC (conditions as described in Example 12) to afford the product Compound 15 (10 mg, yield 32%) as a yellow solid. $^1$H NMR (DMSO-d$_6$ and D$_2$O, 400 Hz) δ 8.98 (s, 1H), 8.08 (d, J=2.4 Hz, 1H), 7.86 (d, J=9.2 Hz, 1H), 7.69 (d, J=9.2 Hz, 1H), 5.90-5.75 (m, 1H), 3.87-3.80 (m, 2H), 3.65-3.55 (m, 2H), 3.25-2.99 (m, 6H), 2.45 (s, 3H), 2.35-2.18 (m, 2H), 2.33 (s, 3H), 1.94 (t, J=7.2 Hz, 2H), 1.90-1.75 (m, 4H), 1.75-1.40 (m, 6H), 1.35-1.25 (m, 6H); MS: 605.3 [M+H]$^+$.

Example 16: Preparation of 4-((4-(6-(((6-acetyl-8-cyclopentyl-5-methyl-7-oxo-7,8-dihydropyrido[2,3-d]pyrimidin-2-yl)amino)pyridin-3-yl)piperazin-1-yl)methyl)-N-hydroxybenzamide (Compound 16)

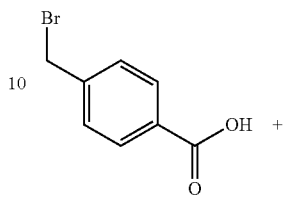

16a

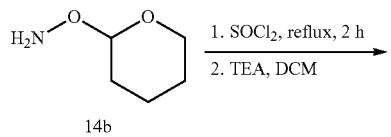

14b

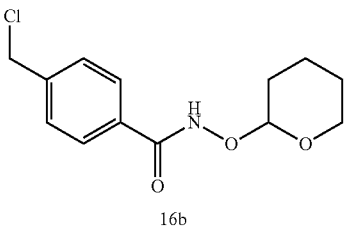

16b

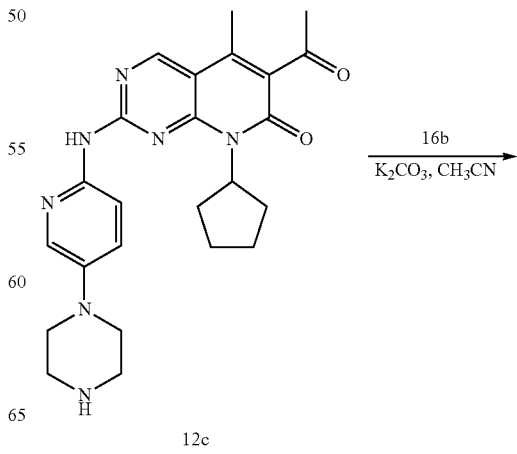

12c

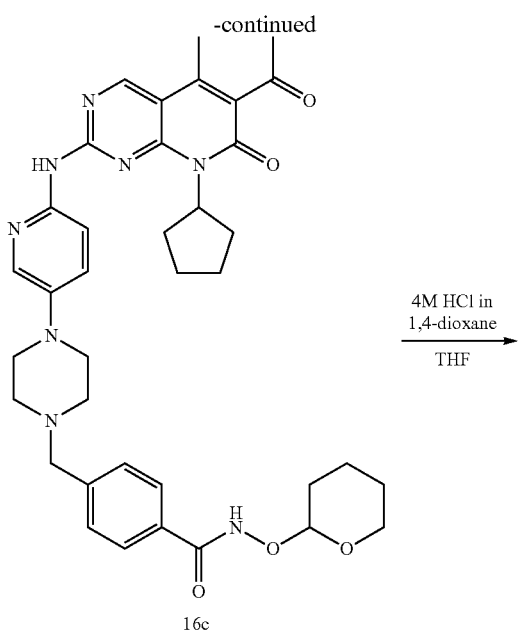

16c

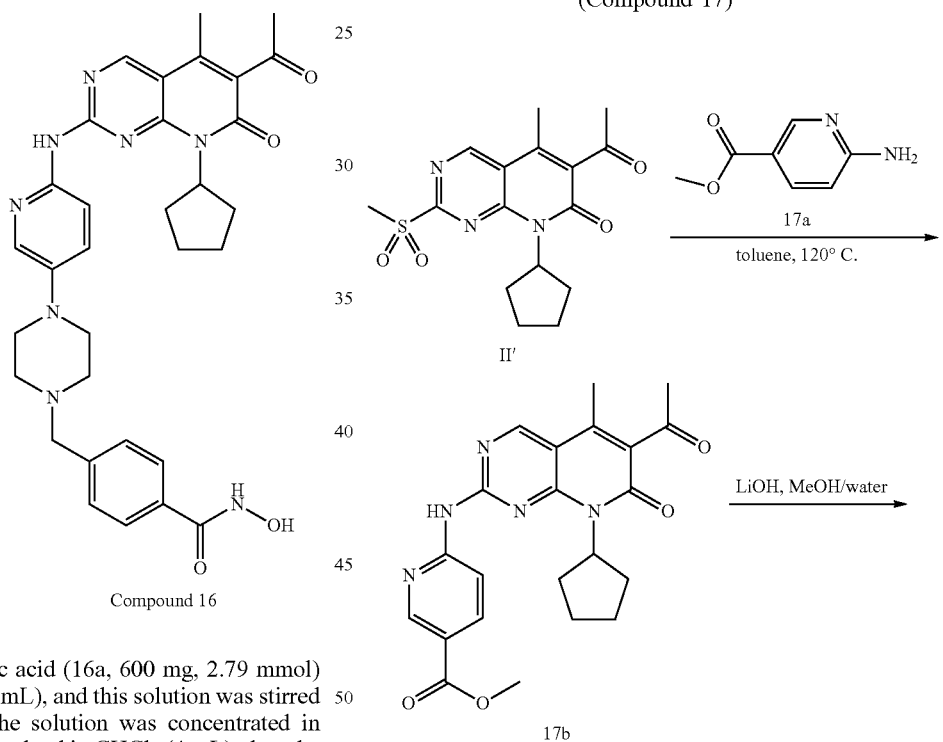

Compound 16

4-(bromomethyl)benzoic acid (16a, 600 mg, 2.79 mmol) was dissolved in SOCl₂ (2 mL), and this solution was stirred at reflux for 2 h. Then the solution was concentrated in vacuo. The residue was dissolved in CHCl₂ (4 mL), then the mixture of O-(tetrahydro-2H-pyran-2-yl) hydroxylamine (14b, 490 mg, 4.19 mmol) and TEA (564 mg, 5.58 mmol) in CH₂Cl₂ (8 mL) was added dropwise at 0° C. The resulting reaction mixture was stirred for 2 h at room temperature. The mixture was concentrated in vacuo and the residue was purified by column chromatography on silica gel (petroleum ether/EtOAc=50/1) to afford the product 16b (200 mg, yield 27%) as a white solid. MS: 186.2 [M−84+H]⁺.

A mixture of compound 12c (40 mg, 0.09 mmol), compound 16b (50 mg, 0.19 mmol), and DIPEA (25 mg, 0.19 mmol) in dichloromethane (2 mL) was stirred for 16 h at 50° C. The mixture was cooled to room temperature, diluted with water (4 mL), and extracted with ethyl acetate (5 mL×3). The combined organic phase was washed with brine (5 mL), dried over anhydrous sodium sulfate, filtered, and concentrated in vacuo to give a residue. The residue was purified by Prep-TLC (CH₂Cl₂/MeOH=15/1) to afford the product 16c (40 mg, yield 66%) as a yellow solid. MS: 681.3 [M+H]⁺.

To a solution of compound 16c (35 mg, 0.051 mmol) in dichloromethane (1 mL) was added a solution of 4M HCl in 1,4-dioxane (0.2 mL) at 0° C. The reaction was stirred for 3 h at room temperature. This mixture was concentrated in vacuo at room temperature, and the residue was purified by Prep-HPLC (conditions as described in Example 12) to afford the product Compound 16 (8.96 mg, yield 27%) as a yellow solid. ¹H NMR (DMSO-d₆, 400 Hz) δ 11.25-11.13 (br s, 1H), 10.10 (s, 1H), 8.97 (s, 1H), 8.29 (s, 1H), 8.04 (d, J=2.4 Hz, 1H), 7.87-7.65 (m, 3H), 7.50-7.33 (m, 3H), 5.87-5.75 (m, 1H), 3.58 (s, 2H), 3.60-3.50 (m, 2H), 3.28-3.03 (m, 6H), 2.42 (s, 3H), 2.31 (s, 3H), 2.29-2.16 (m, 2H), 1.94-1.71 (m, 4H), 1.64-1.51 (m, 2H); MS: 597.3 [M+H]⁺.

Example 17: Preparation of 6-((6-acetyl-8-cyclopentyl-5-methyl-7-oxo-7,8-dihydropyrido[2,3-d]pyrimidin-2-yl)amino)-N-hydroxynicotinamide (Compound 17)

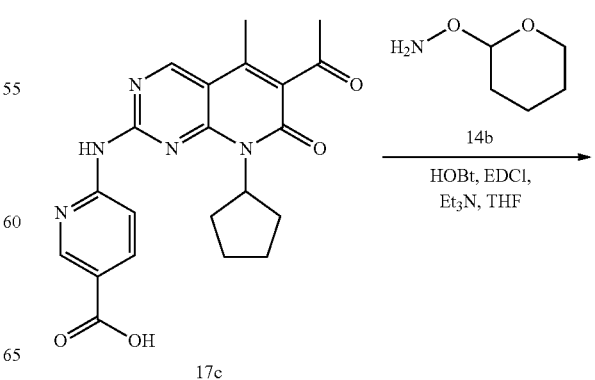

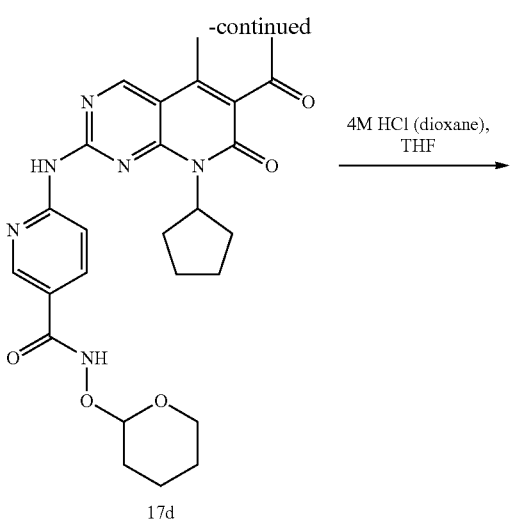

17d

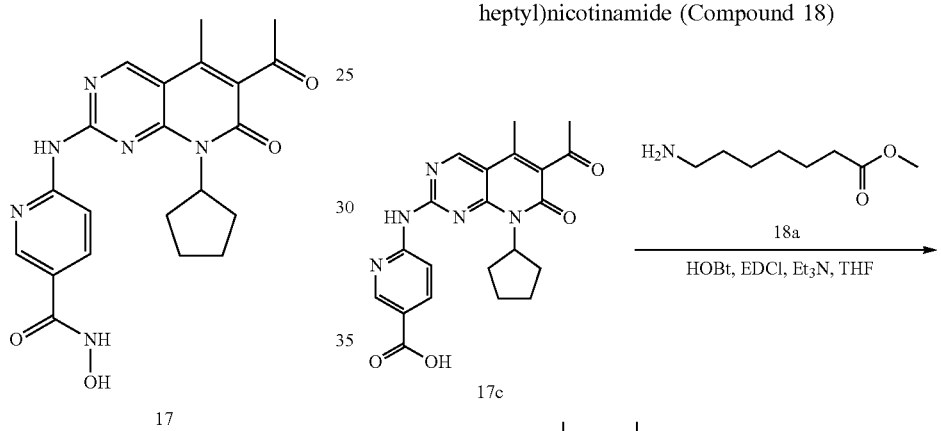

To a solution of compound 17a (131 mg, 0.860 mmol) in toluene (2 mL) was added compound II' (60 mg, 0.172 mmol) at room temperature. The reaction mixture was stirred at 120° C. for 16 h. The reaction mixture was cooled to room temperature, then concentrated in vacuo to dryness. The residue was purified by Combi-Flash (eluting with 30:1 DCM:MeOH) to afford 46 mg of compound 17b (64% yield) as a light brown solid. MS: 422.2 [M+H]$^+$.

To a mixture of solution of 17b (46 mg, 0.11 mmol) in 1:1 methanol and water (5 mL) was added LiOH (46 mg, 1.09 mmol) at room temperature, the mixture was stirred at 50° C. for 5 h. The reaction mixture was cooled to room temperature, then 2N HCl was added to adjust pH=5. The aqueous solution was extracted with ethyl acetate (5 mL×3). The combined organic phase was washed with brine (5 mL), dried over anhydrous sodium sulfate, filtered, and concentrated in vacuo to give the product 17c (44 mg, yield 99%) as a light brown solid. $^1$H NMR (DMSO-d$_6$, 400 Hz) δ 13.06 (br s, 1H), 10.84 (s, 1H), 9.09 (s, 1H), 8.85-8.84 (m, 1H), 8.31-8.24 (m, 2H), 5.93-5.83 (m, 1H), 2.44 (s, 3H), 2.34 (s, 3H), 2.31-2.21 (m, 2H), 2.01-1.92 (m, 2H), 1.88-1.76 (m, 2H), 1.68-1.59 (m, 2H).

To a solution of compound 17c (18.5 mg, 0.045 mmol) in anhydrous THF (1.5 mL) were added HOBt (9 mg, 0.068 mmol), EDCI (13 mg, 0.068 mmol), Et$_3$N (14 mg, 0.136 mmol) and O-(tetrahydro-2H-pyran-2-yl)-hydroxylamine (8 mg, 0.068 mmol), the resulting reaction mixture was stirred at room temperature for 16 h. The reaction mixture was concentrated in vacuo to give a residue, which was purified by Prep-TLC (eluting with 15:1 DCM/MeOH) to afford 11 mg of compound 17d (48% yield) as a white solid.

To a solution of compound 17 (10 mg, 0.020 mmol) in anhydrous THF (0.6 mL) was added a solution of 4M HCl in 1, 4-dioxane (0.2 mL) at 0° C. The reaction was stirred for 3 h at room temperature. This mixture was concentrated in vacuo at room temperature, and the residue was washed with acetonitrile and anhydrous ethyl ether to afford the product Compound 17 (3.8 mg, yield 42%) as a white solid. $^1$H NMR (DMSO-d$_6$, 400 Hz) δ 11.28 (br s, 1H), 10.78 (s, 1H), 9.07 (s, 1H), 8.72 (s, 1H), 8.21-8.15 (m, 2H), 5.92-5.82 (m, 1H), 2.44 (s, 3H), 2.34 (s, 3H), 2.33-2.22 (m, 2H), 2.02-1.91 (m, 2H), 1.87-1.78 (m, 2H), 1.67-1.57 (m, 2H); MS: 423.3 [M+H]$^+$.

Example 18: Preparation of 6-((6-acetyl-8-cyclopentyl-5-methyl-7-oxo-7,8-dihydropyrido[2,3-d]pyrimidin-2-yl)amino)-N-(7-(hydroxyamino)-7-oxoheptyl)nicotinamide (Compound 18)

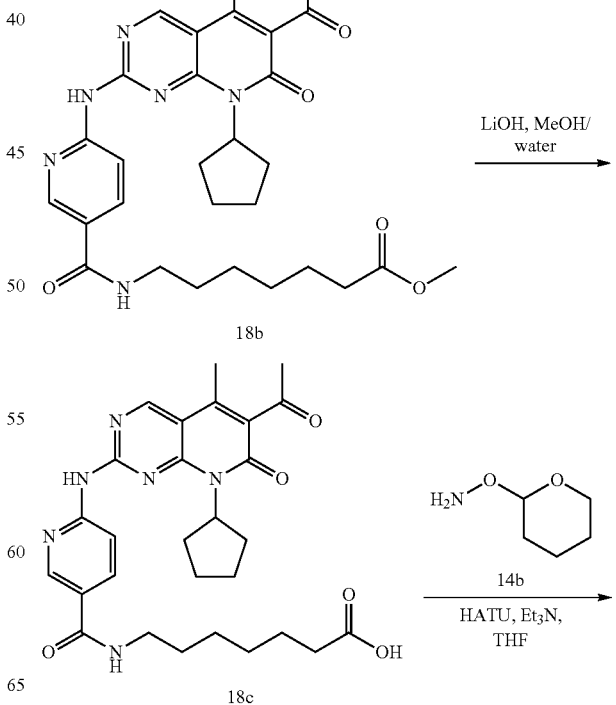

-continued

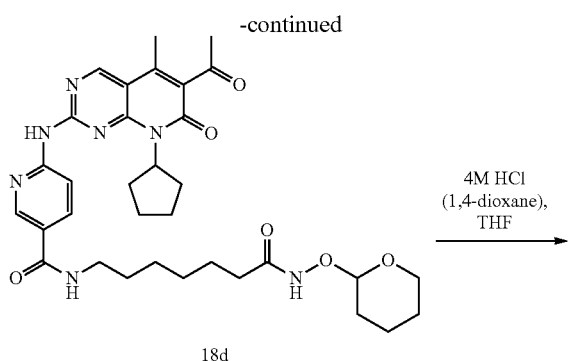

18d

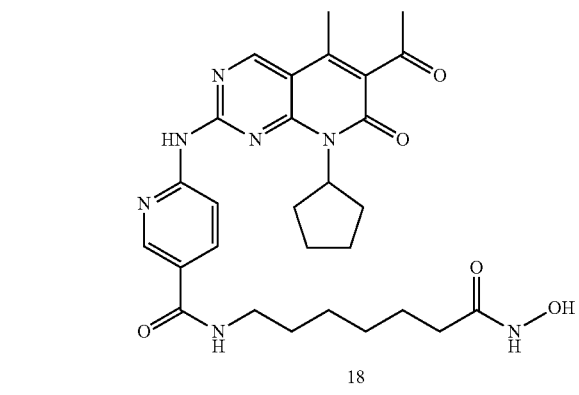

18

To a solution of compound 17c (45 mg, 0.111 mmol) in anhydrous THF (1.5 mL) were added HOBt (30 mg, 0.221 mmol), EDCI (42 mg, 0.221 mmol), Et₃N (34 mg, 0.332 mmol) and 18a (26 mg, 0.166 mmol), the resulting mixture was stirred at room temperature for 16 h. The reaction mixture was concentrated in vacuo to give a residue, which was purified by Prep-TLC (eluting with 15:1 DCM/MeOH) to afford 58 mg of compound 18b (96% yield) as a light yellow solid. MS: 549.4 [M+H]⁺.

To a mixture of solution of 18b (58 mg, 0.106 mmol) in 1:1 methanol and water (5 mL) was added LiOH (27 mg, 0.635 mmol) at room temperature, the mixture was stirred at room temperature for 16 h. The reaction mixture was neutralized with 2N HCl until pH=5. The aqueous solution was extracted with ethyl acetate (5 mL×3). The combined organic phase was washed with brine (5 mL), dried over anhydrous sodium sulfate, filtered. The filtrate was concentrated in vacuo to give the product 18c (55 mg, yield 97%) as white solid. MS: 535.2 [M+H]⁺.

To a solution of compound 18c (55 mg, 0.103 mmol) in anhydrous THF (2 mL) were added HATU (59 mg, 0.154 mmol), Et₃N (31 mg, 0.309 mmol) and O-(tetrahydro-2H-pyran-2-yl)-hydroxylamine (24 mg, 0.206 mmol), the resulting mixture was stirred at room temperature for 16 h. The reaction mixture was concentrated in vacuo to give a residue, which was purified by Prep-TLC (eluting with 12:1 DCM/MeOH) to afford 25 mg of compound 18d (38% yield) as a white solid. ¹H NMR (DMSO-d₆, 400 MHz) δ 10.91 (s, 1H), 10.73 (s, 1H), 9.07 (s, 1H), 8.80 (s, 1H), 8.54-8.49 (m, 1H), 8.27-8.19 (m, 2H), 5.94-5.83 (m, 1H), 4.82-4.78 (m, 1H), 3.95-3.87 (m, 1H), 3.52-3.46 (m, 1H), 3.30-3.21 (m, 2H), 2.44 (s, 3H), 2.34 (s, 3H), 2.30-2.22 (m, 2H), 2.02-1.92 (m, 4H), 1.89-1.77 (m, 2H), 1.68-1.58 (m, 5H), 1.57-1.46 (m, 7H), 1.37-1.22 (m, 4H); MS: 634.4 [M+H]⁺.

To a solution of compound 18d (20 mg, 0.032 mmol) in anhydrous THF (0.6 mL) was added a solution of 4M HCl in 1,4-dioxane (0.1 mL) at 0° C. The reaction was stirred for 1 h at room temperature. This mixture was concentrated in vacuo at room temperature, and the residue was washed with acetonitrile and anhydrous ethyl ether to afford the product Compound 18 (10.7 mg, yield 58%) as a white solid. ¹H NMR (DMSO-d₆, 400 MHz) δ 10.84 (s, 1H), 10.35 (s, 1H), 9.07 (s, 1H), 8.84-8.78 (m, 1H), 8.60-8.52 (m, 1H), 8.27 (dd, J=8.8 Hz, J=2.0 Hz, 1H), 8.19 (d, J=8.8 Hz, 1H), 5.94-5.82 (m, 1H), 3.30-3.20 (m, 2H), 2.44 (s, 3H), 2.34 (s, 3H), 2.33-2.20 (m, 2H), 2.03-1.90 (m, 4H), 1.89-1.77 (m, 2H), 1.68-1.58 (m, 2H), 1.56-1.43 (m, 4H), 1.37-1.21 (m, 4H); MS: 550.3 [M+H]⁺.

Example 19: Preparation of 8-(2-((6-acetyl-8-cyclopentyl-5-methyl-7-oxo-7,8-dihydropyrido[2,3-d]pyrimidin-2-yl)amino)-7,8-dihydro-1,6-naphthyridin-6(5H)-yl)-N-hydroxy-8-oxooctanamide (Compound 19)

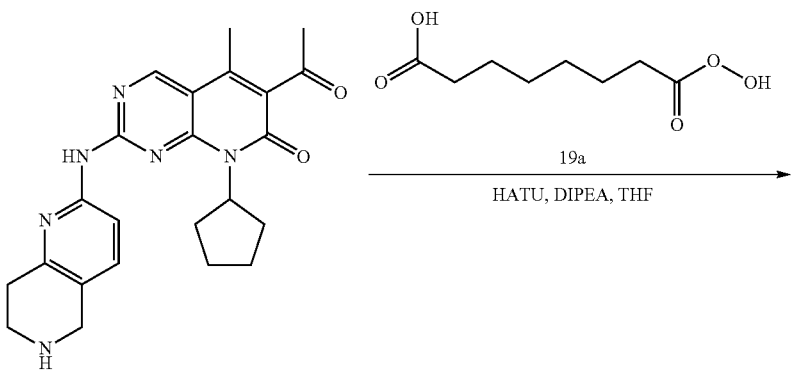

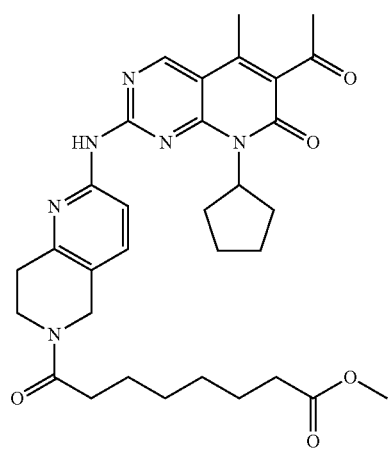

19b

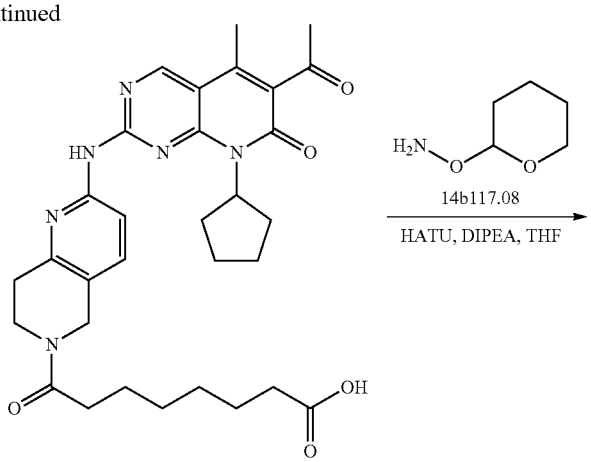

19c

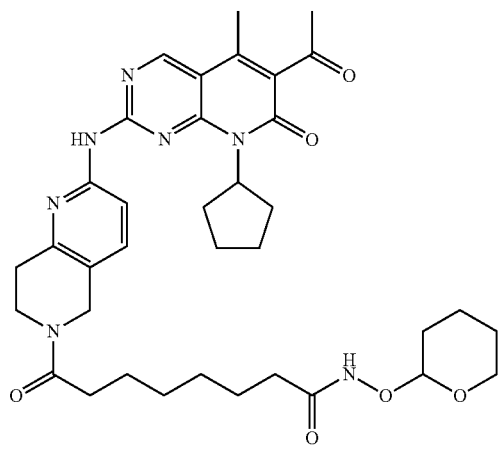

19d

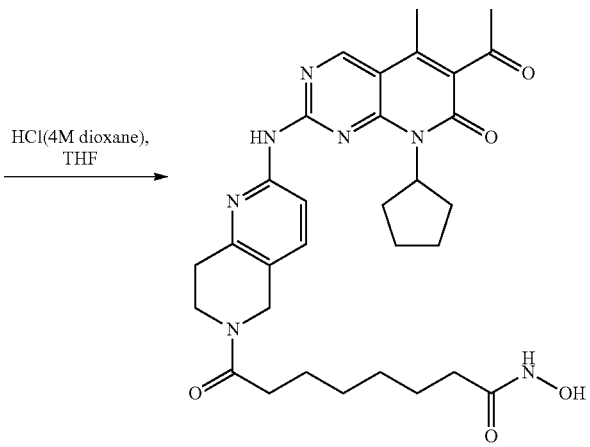

19

A mixture of 19a (40 mg, 0.215 mmol), Compound 8 (45 mg, 0.108 mmol), HATU (82 mg, 0.215 mmol) and DIPEA (42 mg, 0.323 mmol) in anhydrous THF (10 mL) was stirred at room temperature for 16 h. The mixture was diluted with water (20 mL), extracted with ethyl acetate (10 mL×3). The combined organic phase was washed with brine (10 mL), dried over anhydrous sodium sulfate, filtered, and the filtrate was concentrated in vacuo to dryness. The residue was purified by prep-TLC (CH$_2$Cl$_2$/MeOH=15/1) to afford Compound 19b as a light yellow solid (50 mg, yield 79%). MS: 589.3 [M+H]$^+$.

To a mixture of solution of 19b (50 mg, 0.085 mmol) in 1:1 methanol and water (10 mL) was added LiOH (71 mg, 1.70 mmol) at room temperature, the mixture was stirred at 50° C. for 1 h. The reaction mixture was cooled to room temperature, then 2N HCl was added to adjust pH=5. The aqueous solution was extracted with ethyl acetate (10 mL×3). The combined organic phase was washed with brine (10 mL), dried over anhydrous sodium sulfate, and filtered. The filtrate was concentrated in vacuo to give the product 19c (48 mg, yield 98%) as a white solid, which was used for the next step without further purification.

To a solution of compound 19c (48 mg, 0.084 mmol) in anhydrous THF (5 mL) were added HATU (48 mg, 0.125 mmol), DIPEA (32 mg, 0.251 mmol) and O-(tetrahydro-2H-pyran-2-yl)-hydroxylamine (15 mg, 0.125 mmo), the resulting reaction mixture was stirred at room temperature for 16 h. The reaction mixture was diluted with ethyl acetate (20 mL). The mixture was washed with brine (10 mL), dried over anhydrous sodium sulfate, and filtered. The filtrate was concentrated in vacuo to give the residue, which was purified by Prep-TLC (eluting with 25:1 DCM/MeOH) to afford 32 mg of compound 19d (57% yield) as a white solid. $^1$H NMR (DMSO-d$_6$, 400 Hz) δ 10.91 (s, 1H), 10.35 (d, J=10.8 Hz, 1H), 9.00 (s, 1H), 7.95-7.86 (m, 1H), 7.70-7.62 (m, 1H), 5.91-5.80 (m, 1H), 4.82-4.78 (m, 1H), 4.66 (s, 1H), 4.61 (s, 1H), 3.96-3.86 (m, 1H), 3.82-3.74 (m, 2H), 3.52-3.44 (m, 1H), 2.93-2.85 (m, 1H), 2.81-2.75 (m, 1H), 2.43 (s, 3H), 2.44-2.35 (m, 2H), 2.32 (s, 3H), 2.30-2.20 (m, 2H), 2.02-1.86 (m, 4H), 1.84-1.72 (m, 2H), 1.66-1.55 (m, 5H), 1.55-1.42 (m, 7H), 1.34-1.19 (m, 4H); MS: 674.4 [M+H]$^+$.

To a solution of compound 19d (32 mg, 0.048 mmol) in anhydrous THF (0.6 mL) was added a solution of 4M HCl in 1, 4-dioxane (1.0 mL) at 0° C. The reaction was stirred for 3 h at room temperature. This mixture was concentrated in vacuo at room temperature, and the residue was washed with acetonitrile and anhydrous ethyl ether to afford the product Compound 19 (20 mg, yield 71%) as a white solid. $^1$H NMR (DMSO-d$_6$, 400 Hz) δ 10.92 (br s, 1H), 10.36 (brs, 1H), 9.08 (s, 1H), 7.88-7.80 (m, 2H), 5.90-5.79 (m, 1H), 4.70 (s, 1H), 4.64 (s, 1H), 3.81 (t, J=5.8 Hz, 2H), 3.02-2.93 (m, 1H), 2.90-2.82 (m, 1H), 2.44 (s, 3H), 2.41-2.38 (m, 2H), 2.34 (s, 3H), 2.29-2.17 (m, 2H), 1.98-1.91 (m, 4H), 1.85-1.75 (m, 2H), 1.64-1.54 (m, 2H), 1.54-1.46 (m, 4H), 1.35-1.23 (m, 4H); MS: 590.3 [M+H]⁺.

Example 20: Preparation of 4-(4-(6-((6-acetyl-8-cyclopentyl-5-methyl-7-oxo-7,8-dihydropyrido[2,3-d]pyrimidin-2-yl)amino)pyridin-3-yl)piperazine-1-carbonyl)-N-hydroxybenzamide (Compound 20)

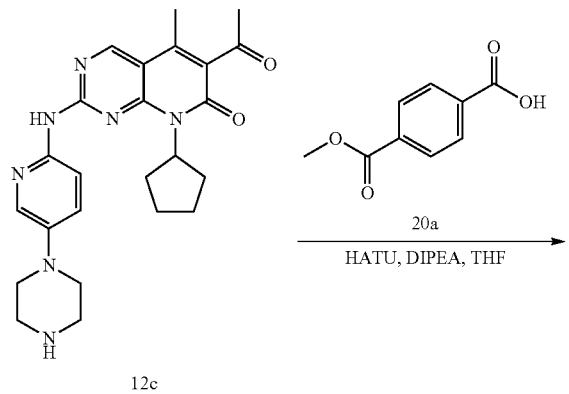

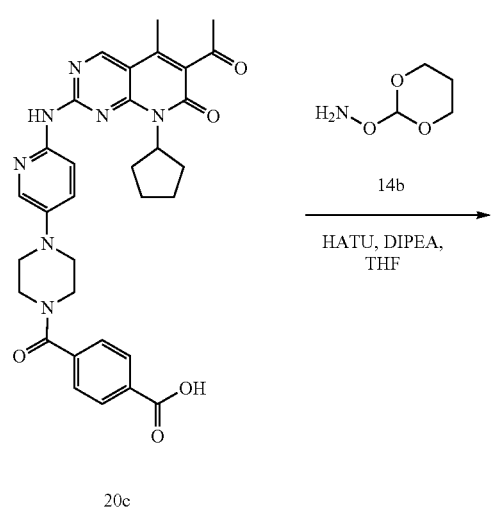

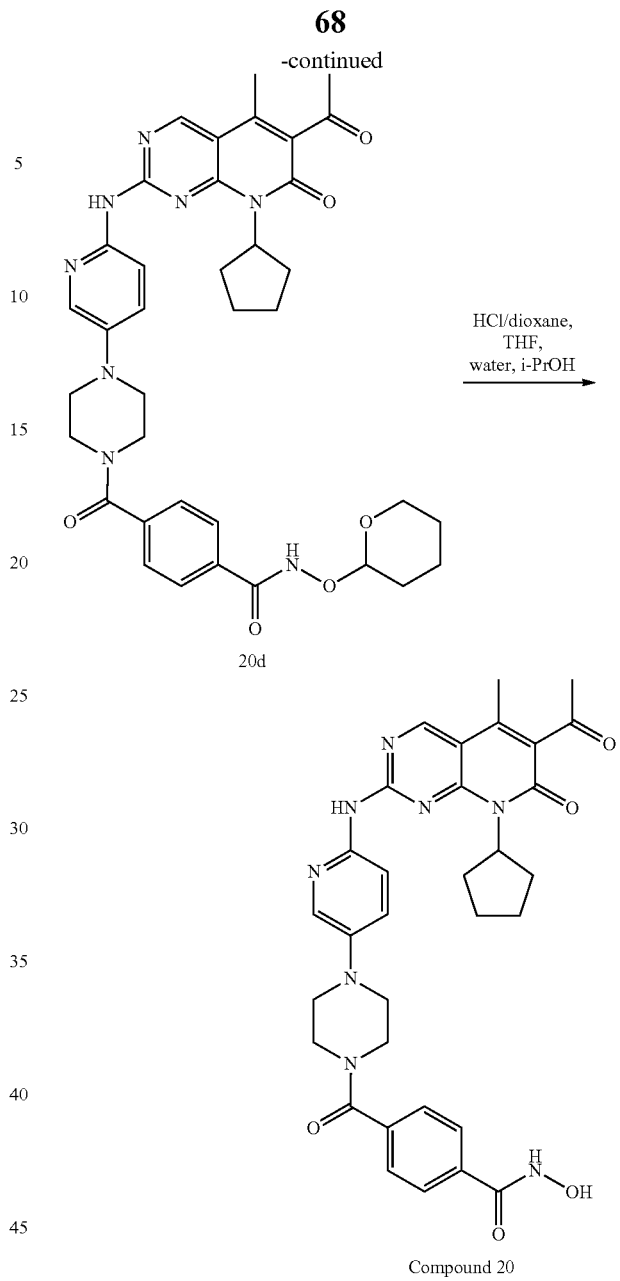

To a solution of compound 12c (45 mg, 0.089 mmol) in anhydrous THF (5 mL) were added HATU (51 mg, 0.134 mmol), DIPEA (35 mg, 0.268 mmol) and 4-(methoxy carbonyl)benzoic acid (24 mg, 0.134 mmol, the resulting mixture was stirred at room temperature for 16 h. The reaction mixture was diluted with water (10 mL), extracted with ethyl acetate (10 mL×3). The combined organic phase was washed with brine (10 mL), dried over anhydrous sodium sulfate, and filtered. The filtrate was concentrated in vacuo to dryness. The resulting residue was purified by Prep-TLC (eluting with 15:1 DCM/MeOH) to afford 42 mg of compound 20b (77% yield) as a light yellow solid. MS: 610.4 [M+H]⁺.

To a mixture of solution of 20b (42 mg, 0.069 mmol) in 1:1 methanol and water (10 mL) was added LiOH (58 mg, 1.38 mmol) at room temperature, the mixture was stirred at 50° C. for 1 h. The reaction mixture was cooled to room temperature, then 2N HCl was added to adjust pH=5. The mixture was extracted with ethyl acetate (10 mL×3). The combined organic phase was washed with brine (10 mL), dried over anhydrous sodium sulfate, and filtered. The filtrate was concentrated in vacuo to give the product 20c (40 mg, yield 98%) as a yellow solid. MS: 596.4 [M+H]$^+$.

To a solution of compound 20c (40 mg, 0.067 mmol) in anhydrous THF (10 mL) were added HATU (33 mg, 0.087 mmol), DIPEA (26 mg, 0.202 mmol) and O-(tetrahydro-2H-pyran-2-yl)-hydroxylamine (16 mg, 0.134 mmol) at room temperature. The resulting reaction mixture was stirred at room temperature for 16 h, then diluted with water (15 mL), extracted with ethyl acetate (10 mL×3). The combined organic phase was washed with brine (10 mL), dried over anhydrous sodium sulfate, and filtered. The filtrate was concentrated in vacuo to give a residue. The residue was purified by Prep-TLC (eluting with 15:1 DCM/MeOH) to afford 46 mg of compound 20d (99% yield) as a yellow solid. MS: 695.4 [M+H]$^+$.

To a solution of compound 20d (15 mg, 0.022 mmol) in anhydrous THF (3 mL) were added a solution of 4M HCl in 1, 4-dioxane (0.8 mL), water (0.1 mL) and isopropanol (1 mL). The reaction was stirred for 2 h at room temperature. The anhydrous ethyl ether was added to the above mixture, the solid precipitate out, filtered. The solid was dried in vacuo to afford the product Compound 20 (10 mg, yield 77%) as a light yellow solid. $^1$H NMR (DMSO-d$_6$, 400 Hz) δ 11.35 (s, 1H), 10.86 (br s, 1H), 9.00 (s, 1H), 8.03 (s, 1H), 7.87-7.77 (m, 4H), 7.53 (d, J=8.4 Hz, 2H), 5.93-5.78 (m, 1H), 3.88-3.75 (m, 2H), 3.53-3.42 (m, 2H), 3.36-3.13 (m, 4H), 2.44 (s, 3H), 2.34 (s, 3H), 2.29-2.16 (m, 2H), 1.98-1.89 (m, 2H), 1.86-1.74 (m, 2H), 1.66-1.54 (m, 2H). MS: 611.3 [M+H]$^+$.

Example 21: Preparation of 4-((2-(((6-acetyl-8-cyclopentyl-5-methyl-7-oxo-7,8-dihydropyrido[2,3-d]pyrimidin-2-yl)amino)-7,8-dihydro-1,6-naphthyridin-6(5H)-yl)methyl)-N-hydroxybenzamide (Compound 21)

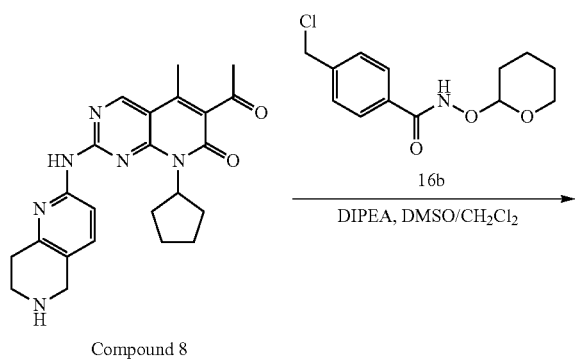

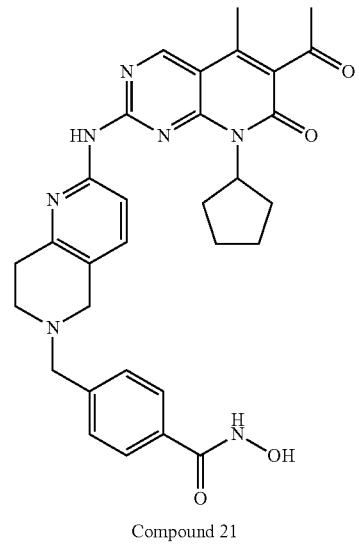

A mixture of compound 8 (45 mg, 0.108 mmol), compound 16b (58 mg, 0.215 mmol) and DIPEA (42 mg, 0.323 mmol) in 1:1 DMF:DCMdichloromethane (5 mL) was stirred for 16 h at 50° C. The mixture was cooled to room temperature, diluted with water (10 mL), and extracted with DCM (10 mL×3). The combined organic phase was washed with brine (5 mL), dried over anhydrous sodium sulfate, and filtered. The filtrate was concentrated in vacuo to give a residue. The residue was purified by Prep-TLC (CH$_2$Cl$_2$/MeOH=20/1) to afford the product 21a (46 mg, yield 66%) as a yellow solid. MS: 652.4 [M+H]$^+$.

To a solution of compound 21a (46 mg, 0.071 mmol) in anhydrous THF (8 mL) was added a solution of 4M HCl in 1, 4-dioxane (1.5 mL) at 0° C. The reaction was stirred for 3 h at room temperature. This mixture was concentrated in vacuo at room temperature, and the residue was washed with small amount of acetonitrile and anhydrous ether. The solid crude product was further purified by Prep-HPLC (conditions as described in Example 12) to afford the product Compound 21 (8.0 mg, yield 20%) as a light yellow solid. $^1$H NMR (DMSO-d$_6$, 400 Hz) δ 11.4-11.00 (br, 1H), 10.28 (s, 1H), 8.99 (s, 1H), 8.39 (s, 1H), 7.87-7.62 (m, 3H), 7.54-7.36 (m, 3H), 5.92-5.76 (m, 1H), 3.77 (s, 2H), 3.55 (s, 2H), 2.89-2.73 (m, 4H), 2.42 (s, 3H), 2.31 (s, 3H), 2.29-2.17 (m, 2H), 1.98-1.83 (m, 2H), 1.83-1.70 (m, 2H), 1.65-1.53 (m, 2H); 568.3 [M+H]⁺.
Example 22: Preparation of 4-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-hydroxybenzamide (Compound 22)
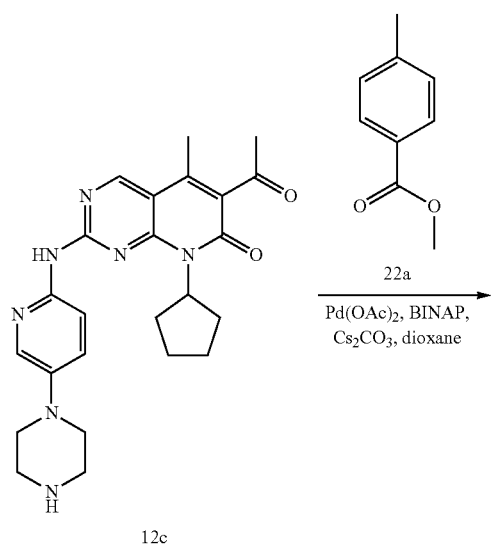
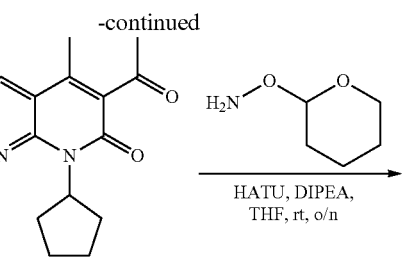
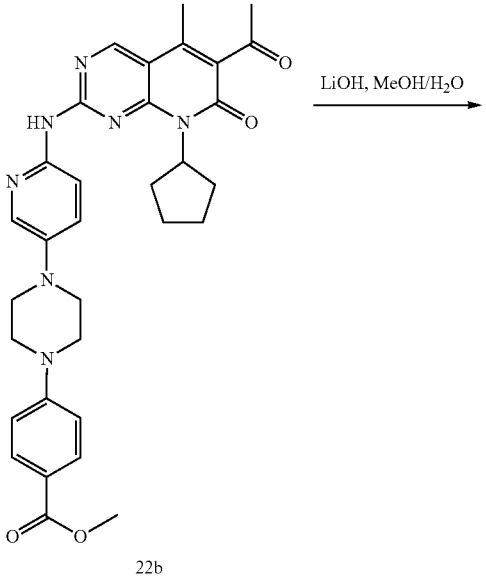
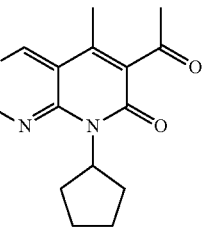
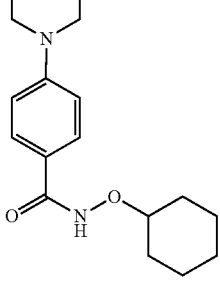

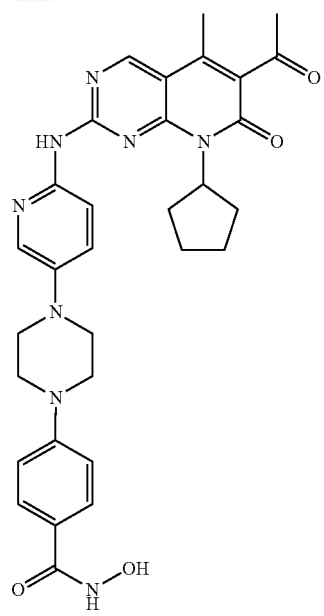
Compound 22
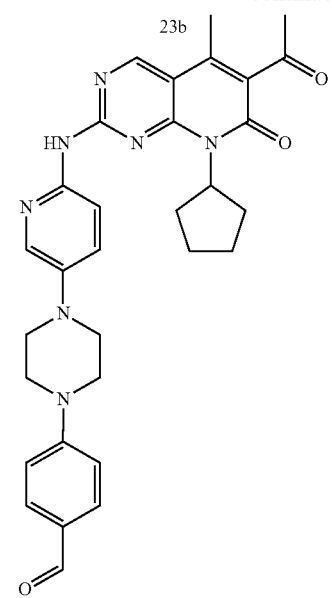
23b
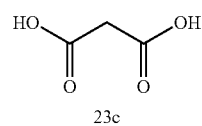
23c
Following the above scheme, Compound 22 was obtained. 583.2 [M+H]
Example 23: Preparation of (E)-3-(4-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)phenyl)-N-hydroxyacrylamide (Compound 23)
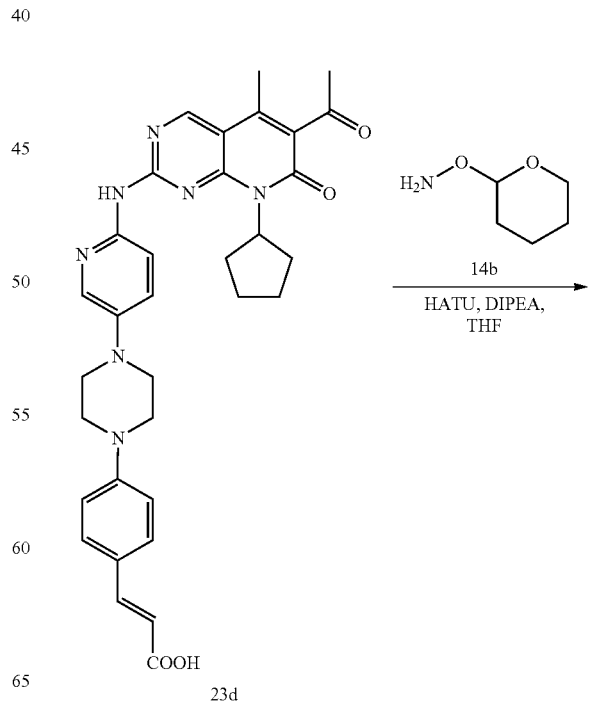

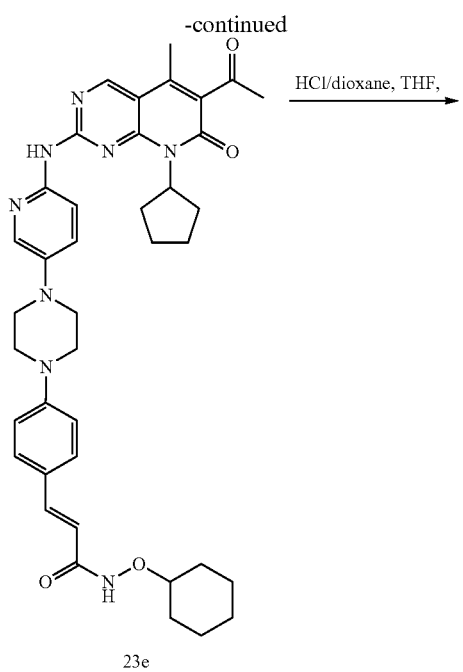

23e

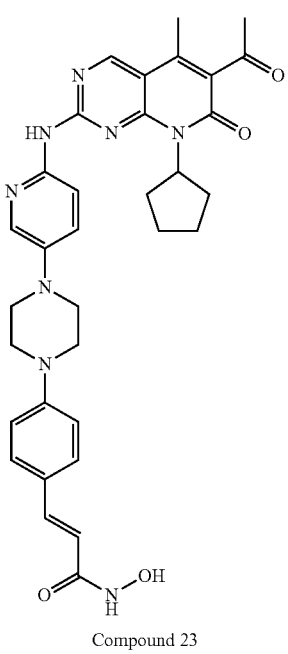

Compound 23

Following the above scheme, Compound 23 was obtained, MS: 609.3 [M+H]+.

Example 24: Biology Assays

1. CDK2, CDK4 and CDK6 Kinase Assays:

In vitro enzymatic activity of the CDK isoforms CDK2/CycA2, CDK4/CycD3 and CDK6/cycD3 were measured using Mobility Shift Assay that monitors phosphorylation ratio of FAM labelled peptide (Peptide 18 for CDK2/CycA2, Peptide 8 for CDK4/CycD3 and CDK6/cycD3). CDK2/CycA2 and CDK6/cycD3 were assayed under buffer conditions in the presence of 50 mM HEPES (pH 7.5), 10 mM MgCl2, 0.0015% Brij-35, and 2 mM dithiothreitol, CDK4/CycD3 with buffer condition of 20 mM HEPES (pH 7.5), 10 mM MgCl2, 0.01% Triton X-100, and 2 mM dithiothreitol.

Prepare compounds to 50× of the final desired highest inhibitor concentration by 100% DMSO and serial dilution in 3-fold for total of 10 concentrations. For each isoform, dosage of enzyme and substrate are CDK2/CycA2 12 nM, ATP Km 39 µM; CDK4/CycD3 10 nM, ATP Km 221 µM; CDK6/cycD3 15 nM, ATP Km 800 µM. After assay for 60 min, 180 min, 60 min respectively at 28° C., reactions were terminated with stop solution (50 mM EDTA, 0.015% Brij-35, 0.2% Coating Reagent #3 and 100 mM HEPES (pH 7.5)). Collect conversion on Caliper EZ Reader. IC50 values were calculated by fitting the dose-response curves with Xlfit excel add-in version 4.3.1.

The testing results of the representative compounds are listed in Table 1 below.

TABLE 1

CDK2, CDK4 and CDK6 assays

| Compound | CDK4(IC$_{50}$, nM) | CDK6(IC$_{50}$, nM) | CDK2(IC$_{50}$, µM) |
|---|---|---|---|
| 1 | <10 | <25 | >5 |
| 2 | <25 | <100 | >5 |
| 3 | <10 | <25 | >5 |
| 4-1 | <25 | <100 | <1 |
| 4-2 | <50 | <100 | |
| 5 | <10 | <25 | >5 |
| 6 | <10 | <25 | >5 |
| 7 | <10 | <25 | <1 |
| 7R | <10 | <25 | <1 |
| 7S | <10 | <25 | <1 |
| 8 | <10 | <100 | >1 |
| 12 | <10 | <25 | >10 |
| 13 | <25 | <50 | >1 |
| 14 | <10 | <10 | |
| 15 | <10 | <25 | >1 |
| 16 | <10 | <50 | >1 |
| 17 | <50 | <500 | >1 |
| 18 | <50 | <1000 | >1 |

2. HDAC-1, HDAC-2 and HDAC-6 Assays:

The inhibitory effect of compounds on HDAC-1, HDAC-2 and HDAC-6 function was determined in vitro using an optimized homogenous assay performed in 384-well plate format. In this assay, recombinant, full-length HDAC-1, HDAC-2 or HDAC-6 protein (BPS Biosciences) was incubated with Ac-peptide-AMC with concentration in Km plot. Reactions were performed in Tris-based assay buffer and followed for fluorogenic release of 7-amino-4-methylcoumarin from substrate upon deacetylase and trypsin enzymatic activity. Fluorescence measurements were obtained using a multilabel plate reader (Synergy MX with excitation at 355 nm and emission at 460 nm). Data were analyzed on a plate-by-plate basis for the linear range of fluorescence over time. Fit the data in GraphPad Prism V5.0 software to obtain IC$_{50}$ values using equation (Y=Bottom+(Top−Bottom)/(1+10^((Log IC50−X)*Hill Slope), Y is % inhibition and X is compound concentration).

The testing results of the representative compounds are listed in Table 1 below.

TABLE 2

HDAC-1 and HDAC-6 assays (IC$_{50}$, nM)

| Compound | HDAC1 | HDAC6 |
|---|---|---|
| 12 | <50 | <10 |
| 14 | <500 | <50 |
| 15 | <500 | <50 |

TABLE 2-continued

HDAC-1 and HDAC-6 assays (IC$_{50}$, nM)

| Compound | HDAC1 | HDAC6 |
|---|---|---|
| 16 | <500 | <10 |
| 17 | <500 | <50 |
| 18 | <50 | <10 |

OTHER EMBODIMENTS OF THE INVENTION

The invention has been described above with the reference to specific examples and embodiments, not to be constructed as limiting the scope of this invention in any way. It is understood that various modifications and additions can be made to the specific examples and embodiments disclosed without departing from the spirit of the invention, and such modifications and additions are contemplated as being part of the present invention.

What is claimed is:

1. A compound of Formula (I):

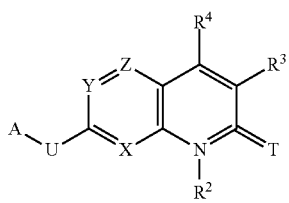

or a pharmaceutically acceptable salt, hydrate, or stereoisomer thereof,
wherein:
(i) A is Formula (II):

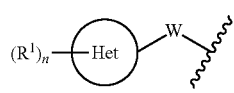

wherein:
W is pyridinyl;
Het is $C_{3-8}$ cycloalkyl or 4- to 15-membered heterocyclyl, wherein the 4- to 15-membered heterocyclyl contains 1, 2, 3, 4, or 5 heteroatoms independently selected from the group consisting of nitrogen, oxygen, and sulfur, and further wherein the $C_{3-8}$ cycloalkyl or the 4- to 15-membered heterocyclyl is monocyclic, polycyclic, bridged, or spirocyclic;
each $R^1$ is independently halogen, CN, $C_{1-8}$ alkyl, $(CH_2)_p$—V—$(CH_2)_q$—C(O)NHOH, $C_{2-8}$ alkenyl, $C_{2-8}$ alkynyl, C(O)$R^5$, C(O)NR$^5$R$^6$, C(O)OR$^5$, NR$^5$R$^6$, NR$^6$C(O)R$^5$, OR$^5$, OC(O)R$^5$, SR$^5$, S(O)$_2$R$^5$, $C_{3-8}$ cycloalkyl, 3- to 12-membered heterocyclyl, $C_{6-12}$ aryl, or 5- to 15-membered heteroaryl;
each V is independently —$C_{1-8}$ alkylene-, —CR$^{14}$R$^{15}$—, —CH=CH—, —C≡C—, —C(O)—, —C(O)NH—, —C(O)O—, —NR$^{13}$—, —NHC(O)—, —NHC(O)NH—, —NHS(O)$_2$—, —O—, —OC(O)—, —OC(O) O—, —S—, —S(O)—, —S(O)$_2$—, —S(O)$_2$NH—, $C_{3-8}$ cycloalkylene, 3- to 12-membered heterocyclylene, $C_{6-12}$ arylene, 5- to 15-membered heteroarylene, or —V$^1$—(CH$_2$)$_t$—V$^2$—;
each V$^1$ is independently —CH=CH—, —C≡C—, —C(O)NH—, —NR$^{13}$—, —NHC(O)—, —NHS(O)$_2$—, —O—, —S—, —S(O)$_2$—, —S(O)$_2$NH—, $C_{3-8}$ cycloalkylene, 3- to 12-membered heterocyclylene, $C_{6-12}$ arylene, or 5- to 15-membered heteroarylene;
each V$^2$ is independently —CH=CH—, —C≡C—, —C(O)NH—, —NR$^{13}$—, —NHC(O)—, —NHS(O)$_2$—, —O—, —S—, —S(O)$_2$—, —S(O)$_2$NH—, $C_{3-8}$ cycloalkylene, 3- to 12-membered heterocyclylene, $C_{6-12}$ arylene, or 5- to 15-membered heteroarylene;
each $R^{13}$ is independently hydrogen, $C_{1-4}$ alkyl, C(O)$R^5$, or S(O)$_2$R$^5$;
each $R^{14}$ is independently hydrogen, halogen, CN, $C_{1-4}$ alkyl, $C_{2-4}$ alkenyl, $C_{2-4}$ alkynyl, C(O)$R^5$, C(O)NR$^5$R$^6$, C(O)OR$^5$, NR$^5$R$^6$, NR$^6$C(O)R$^5$, OR$^5$, OC(O)R$^5$, SR$^5$, S(O)$_2$R$^5$, $C_{3-8}$ cycloalkyl, 3- to 12-membered heterocyclyl, $C_{6-12}$ aryl, or 5- to 15-membered heteroaryl;
each $R^{15}$ is independently hydrogen, halogen, CN, $C_{1-4}$ alkyl, $C_{2-4}$ alkenyl, $C_{2-4}$ alkynyl, C(O)$R^5$, C(O)NR$^5$R$^6$, C(O)OR$^5$, NR$^5$R$^6$, NR$^6$C(O)R$^5$, OR$^5$, OC(O)R$^5$, SR$^5$, S(O)$_2$R$^5$, $C_{3-8}$ cycloalkyl, 3- to 12-membered heterocyclyl, $C_{6-12}$ aryl, or 5- to 15-membered heteroaryl; or
each $R^{14}$ and $R^{15}$, together with the carbon atom to which they are attached, independently forms a 3- to 9-membered ring, wherein each 3- to 9-membered ring optionally and independently contains 1, 2, or 3 heteroatoms independently selected from the group consisting of nitrogen, oxygen, and sulfur;
n is 1, 2, or 3;
each p is independently 0, 1, 2, 3, 4, 5, 6, 7, 8, 9, or 10;
each q is independently 0, 1, 2, 3, 4, 5, 6, 7, 8, 9, or 10;
each t is independently 0, 1, 2, 3, 4, or 5; and
〜 is the point of attachment to U; or
(ii) A is Formula (III):

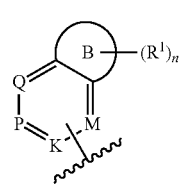

wherein:
(a) K is CR$^8$;
M is N;
P is CR$^8$; and
Q is CR$^8$; or
(b) K is CR$^8$;
M is CR$^8$;
P is N; and
Q is CR$^8$;
B is a 5- to 15-membered heterocyclyl, wherein the 5- to 15-membered heterocyclyl contains 1, 2, 3, 4, or 5 heteroatoms independently selected from the group consisting of nitrogen, oxygen, and sulfur;

each $R^1$ is independently halogen, CN, $C_{1-8}$ alkyl, $(CH_2)_p$—V—$(CH_2)_q$—C(O)NHOH, $C_{2-8}$ alkenyl, $C_{2-8}$ alkynyl, $C(O)R^5$, $C(O)NR^5R^6$, $C(O)OR^5$, $NR^5R^6$, $NR^6C(O)R^5$, $OR^5$, $OC(O)R^5$, $SR^5$, $S(O)_2R^5$, $C_{3-8}$ cycloalkyl, 3- to 12-membered heterocyclyl, $C_{6-12}$ aryl, or 5- to 15-membered heteroaryl;

each V is independently —$C_{1-8}$ alkylene-, —$CR^{14}R^{15}$—, —CH═CH—, —C≡C—, —C(O)—, —C(O)NH—, —C(O)O—, —$NR^{13}$—, —NHC(O)—, —NHC(O)NH—, —$NHS(O)_2$—, —O—, —OC(O)—, —OC(O)O—, —S—, —S(O)—, —$S(O)_2$—, —$S(O)_2NH$—, $C_{3-8}$ cycloalkylene, 3- to 12-membered heterocyclylene, $C_{6-12}$ arylene, 5- to 15-membered heteroarylene, or —$V^1$—(CH)—$V^2$—;

each $V^1$ is independently —CH═CH—, —C≡C—, —C(O)NH—, —$NR^{13}$—, —NHC(O)—, —$NHS(O)_2$—, —O—, —S—, —$S(O)_2$—, —$S(O)_2NH$—, $C_{3-8}$ cycloalkylene, 3- to 12-membered heterocyclylene, $C_{6-12}$ arylene, or 5- to 15-membered heteroarylene;

each $V^2$ is independently —CH═CH—, —C≡C—, —C(O)NH—, —$NR^{13}$—, —NHC(O)—, —$NHS(O)_2$—, —O—, —S—, —$S(O)_2$—, —$S(O)_2NH$—, $C_{3-8}$ cycloalkylene, 3- to 12-membered heterocyclylene, $C_{6-12}$ arylene, or 5- to 15-membered heteroarylene;

each $R^{13}$ is independently hydrogen, $C_{1-4}$ alkyl, $C(O)R^5$, or $S(O)_2R^5$;

each $R^{14}$ is independently hydrogen, halogen, CN, $C_{1-4}$ alkyl, $C_{2-4}$ alkenyl, $C_{2-4}$ alkynyl, $C(O)R^5$, $C(O)NR^5R^6$, $C(O)OR^5$, $NR^5R^6$, $NR^6C(O)R^5$, $OR^5$, $OC(O)R^5$, $SR^5$, $S(O)_2R^5$, $C_{3-8}$ cycloalkyl, 3- to 12-membered heterocyclyl, $C_{6-12}$ aryl, or 5- to 15-membered heteroaryl;

each $R^{15}$ is independently hydrogen, halogen, CN, $C_{1-4}$ alkyl, $C_{2-4}$ alkenyl, $C_{2-4}$ alkynyl, $C(O)R^5$, $C(O)NR^5R^6$, $C(O)OR^5$, $NR^5R^6$, $NR^6C(O)R^5$, $OR^5$, $OC(O)R^5$, $SR^5$, $S(O)_2R^5$, $C_{3-8}$ cycloalkyl, 3- to 12-membered heterocyclyl, $C_{6-12}$ aryl, or 5- to 15-membered heteroaryl; or each $R^{14}$ and $R^{15}$, together with the carbon atom to which they are attached, independently forms a 3- to 9-membered ring, wherein each 3- to 9-membered ring optionally and independently contains 1, 2, or 3 heteroatoms independently selected from the group consisting of nitrogen, oxygen, and sulfur;

n is 1, 2, or 3;

each p is independently 0, 1, 2, 3, 4, 5, 6, 7, 8, 9, or 10;

each q is independently 0, 1, 2, 3, 4, 5, 6, 7, 8, 9, or 10;

each t is independently 0, 1, 2, 3, 4, or 5; and

~~~ is the point of attachment to U; or (iii) A is Formula (V):

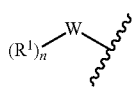

(V)

wherein:

W is pyridinyl;

each $R^1$ is independently halogen, CN, $C_{1-8}$ alkyl, $(CH_2)_p$—V—$(CH_2)_q$—C(O)NHOH, $C_{2-8}$ alkenyl, $C_{2-8}$ alkynyl, $C(O)R^5$, $C(O)NR^5R^6$, $C(O)OR^5$, $NR^5R^6$, $NR^6C(O)R^5$, $OR^5$, $OC(O)R^5$, $SR^5$, $S(O)_2R^5$, $C_{3-8}$ cycloalkyl, 3- to 12-membered heterocyclyl, $C_{6-12}$ aryl, or 5- to 15-membered heteroaryl;

each V is independently —$C_{1-8}$ alkylene-, —$CR^{14}R^{15}$—, —CH═CH—, —C≡C—, —C(O)—, —C(O)NH—, —C(O)O—, —$NR^{13}$—, —NHC(O)—, —NHC(O)NH—, —$NHS(O)_2$—, —O—, —OC(O)—, —OC(O)O—, —S—, —S(O)—, —$S(O)_2$—, —$S(O)_2NH$—, $C_{3-8}$ cycloalkylene, 3- to 12-membered heterocyclylene, $C_{6-12}$ arylene, 5- to 15-membered heteroarylene, or —$V^1$—$(CH_2)_t$—$V^2$—;

each $V^1$ is independently —CH═CH—, —C≡C—, —C(O)NH—, —$NR^{13}$—, —NHC(O)—, —$NHS(O)_2$—, —O—, —S—, —$S(O)_2$—, —$S(O)_2NH$—, $C_{3-8}$ cycloalkylene, 3- to 12-membered heterocyclylene, $C_{6-12}$ arylene, or 5- to 15-membered heteroarylene;

each $V^2$ is independently —CH═CH—, —C≡C—, —C(O)NH—, —$NR^{13}$, —NHC(O)—, —$NHS(O)_2$—, —O—, —S—, —$S(O)_2$—, —$S(O)_2NH$—, $C_{3-8}$ cycloalkylene, 3- to 12-membered heterocyclylene, $C_{6-12}$ arylene, or 5- to 15-membered heteroarylene;

each $R^{13}$ is independently hydrogen, $C_{1-4}$ alkyl, $C(O)R^5$, or $S(O)_2R^5$;

each $R^{14}$ is independently hydrogen, halogen, CN, $C_{1-4}$ alkyl, $C_{2-4}$ alkenyl, $C_{2-4}$ alkynyl, $C(O)R^5$, $C(O)NR^5R^6$, $C(O)OR^5$, $NR^5R^6$, $NR^6C(O)R^5$, $OR^5$, $OC(O)R^5$, $SR^5$, $S(O)_2R^5$, $C_{3-8}$ cycloalkyl, 3- to 12-membered heterocyclyl, $C_{6-12}$ aryl, or 5- to 15-membered heteroaryl;

each $R^{15}$ is independently hydrogen, halogen, CN, $C_{1-4}$ alkyl, $C_{2-4}$ alkenyl, $C_{2-4}$ alkynyl, $C(O)R^5$, $C(O)NR^5R^6$, $C(O)OR^5$, $NR^5R^6$, $NR^6C(O)R^5$, $OR^5$, $OC(O)R^5$, $SR^5$, $S(O)_2R^5$, $C_{3-8}$ cycloalkyl, 3- to 12-membered heterocyclyl, $C_{6-12}$ aryl, or 5- to 15-membered heteroaryl; or each $R^{14}$ and $R^{15}$, together with the carbon atom to which they are attached, independently forms a 3- to 9-membered ring, wherein each 3- to 9-membered ring optionally and independently contains 1, 2, or 3 heteroatoms independently selected from the group consisting of nitrogen, oxygen, and sulfur;

n is 1, 2, or 3;

each p is independently 0, 1, 2, 3, 4, 5, 6, 7, 8, 9, or 10;

each q is independently 0, 1, 2, 3, 4, 5, 6, 7, 8, 9, or 10;

each t is independently 0, 1, 2, 3, 4, or 5; and

~~~ is the point of attachment to U;

U is —$NR^7$—, —O—, or —S—;

T is O;

X is N;

Y is N;

Z is $CR^8$;

$R^2$ is hydrogen, $C_{1-8}$ alkyl, $C_{2-8}$ alkenyl, $C_{2-8}$ alkynyl, $C_{3-8}$ cycloalkyl, 3- to 12-membered heterocyclyl, $C_{6-12}$ aryl, or 5- to 15-membered heteroaryl;

$R^3$ is hydrogen, halogen, CN, $NO_2$, $C_{1-8}$ alkyl, $(CR^9R^{10})_mC(O)R^5$, $(CR^9R^{10})_mC(O)NR^5R^6$, $(CR^9R^{10})_mC(O)OR^5$, $(CR^9R^{10})_mNR^5R^6$, $(CR^9R^{10})_mNR^7C(O)R^5$, $(CR^9R^{10})_mNR^7C(O)NR^5R^6$, $(CR^9R^{10})_mNR^7C(O)OR^5$, $(CR^9R^{10})_mOR^5$, $(CR^9R^{10})_mOC(O)R^5$, $(CR^9R^{10})_mOC(O)NR^5R^6$, $(CR^9R^{10})_mOC(O)OR^5$, $(CR^9R^{10})_mSR^5$, $(CR^9R^{10})_mS(O)R^5$, $(CR^9R^{10})_mS(O)_2R^5$, $C_{2-8}$ alkenyl, $C_{2-8}$ alkynyl, $C_{3-8}$ cycloalkyl, 3- to 12-membered heterocyclyl, $C_{6-12}$ aryl, or 5- to 15-membered heteroaryl;

$R^4$ is hydrogen, halogen, CN, $C_{1-8}$ alkyl, $C_{2-8}$ alkenyl, $C_{2-8}$ alkynyl, $NR^5R^6$, $OR^5$, $C_{3-8}$ cycloalkyl, 3- to 12-membered heterocyclyl, $C_{6-12}$ aryl, or 5- to 15-membered heteroaryl;

each $R^5$ is independently hydrogen, $C_{1-8}$ alkyl, $C_{2-8}$ alkenyl, $C_{2-8}$ alkynyl, $C_{3-8}$ cycloalkyl, 3- to 12-membered heterocyclyl, $C_{6-12}$ aryl, or 5- to 15-membered heteroaryl;

each $R^6$ is independently hydrogen, $C_{1-8}$ alkyl, $C_{2-8}$ alkenyl, $C_{2-8}$ alkynyl, $C_{3-8}$ cycloalkyl, 3- to 12-membered heterocyclyl, $C_{6-12}$ aryl, or 5- to 15-membered heteroaryl; or each $R^5$ and $R^6$, together with the nitrogen atom to which they are attached, independently forms a 3- to 9-membered ring, wherein each 3- to 9-membered ring optionally and independently contains 1, 2, or 3 additional heteroatoms independently selected from the group consisting of nitrogen, oxygen, and sulfur;

$R^7$ is hydrogen or $C_{1-4}$ alkyl;

$R^8$ is hydrogen, halogen, CN, $C_{1-8}$ alkyl, $C_{2-8}$ alkenyl, $C_{2-8}$ alkynyl, $C(O)R^5$, $C(O)OR^5$, $NR^5R^6$, $OR^5$, or $SR^5$;

each $R^9$ is independently hydrogen or $C_{1-8}$ alkyl;

each $R^{10}$ is independently hydrogen or $C_{1-8}$ alkyl; or each $R^9$ and $R^{10}$, together with the carbon atom to which they are attached, independently forms a 3- to 9-membered ring, wherein each 3- to 9-membered ring optionally and independently contains 1, 2, or 3 additional heteroatoms independently selected from the group consisting of nitrogen, oxygen, and sulfur; and m is 0, 1, 2, or 3;

wherein each alkyl, alkenyl, alkynyl, cycloalkyl, heterocyclyl, aryl, or heteroaryl is optionally and independently substituted with 1, 2, or 3 substituents independently selected from the group consisting of halogen, CN, $NO_2$, $C_{1-8}$ alkyl, $C_{2-8}$ alkenyl, $C_{2-8}$ alkynyl, $C(O)R^5$, $C(O)NR^5R^6$, $C(O)OR^5$, $NR^5R^6$, $OR^5$, $SR^5$, $S(O)_2R^5$, $C_{3-10}$ cycloalkyl, 3- to 12-membered heterocyclyl, $C_{6-12}$ aryl, and 5- to 15-membered heteroaryl;

with the provisos that:
(1) if A is Formula (II), Formula (III), or Formula (V) and n is 1, then $R^1$ is $(CH_2)_p-V-(CH_2)_q-C(O)NHOH$;
(2) if A is Formula (II), Formula (III), or Formula (V) and n is 2, then one $R^1$ is $(CH_2)_p-V-(CH_2)_q-C(O)NHOH$ and the other $R^1$ is other than $(CH_2)_p-V-(CH_2)_q-C(O)NHOH$; and
(3) if A is Formula (II), Formula (III), or Formula (V) and n is 3, then one $R^1$ is $(CH_2)_p-V-(CH_2)_q-C(O)NHOH$ and the other two $R^1$ substituents are each independently other than $(CH_2)_p-V-(CH_2)_q-C(O)NHOH$.

2. The compound of claim 1, or a pharmaceutically acceptable salt, hydrate, or stereoisomer thereof, wherein:
each $R^1$ is independently $(CH_2)_p-V-(CH_2)_q-C(O)NHOH$;

each V is independently $-CH_2-$, $-CH=CH-$, $-C\equiv C-$, $-C(O)-$, $-C(O)NH-$, $-C(O)O-$, $-NR^{13}-$, $-O-$, $-S(O)_2-$, $-S(O)_2NH-$, $C_{3-8}$ cycloalkylene, 3- to 12-membered heterocyclylene, $C_{6-12}$ arylene, 5- to 15-membered heteroarylene, or $-V^1-(CH_2)_t-V^2-$;

each $V^1$ is independently $-CH=CH-$, $-NR^{13}-$, $-O-$, $C_{3-8}$ cycloalkylene, 3- to 12-membered heterocyclylene, $C_{6-12}$ arylene, or 5- to 15-membered heteroarylene;

each $V^2$ is independently $-CH=CH-$, $-NR^{13}-$, $-O-$, $C_{3-8}$ cycloalkylene, 3- to 12-membered heterocyclylene, $C_{6-12}$ arylene, or 5- to 15-membered heteroarylene;

each $R^{13}$ is independently hydrogen or $C_{1-4}$ alkyl;

n is 1, 2, or 3;

each p is independently 0, 1, 2, 3, 4, 5, or 6;

each q is independently 0, 1, 2, 3, 4, 5, or 6; and each t is independently 0, 1, 2, or 3.

3. The compound of claim 1, or a pharmaceutically acceptable salt, hydrate, or stereoisomer thereof, wherein:
U is $-NH-$;
Z is CH;
$R^2$ is $C_{3-8}$ cycloalkyl;
$R^3$ is $C(O)C_{1-8}$ alkyl; and
$R^4$ is $C_{1-8}$ alkyl.

4. The compound of claim 1, or a pharmaceutically acceptable salt, hydrate, or stereoisomer thereof, wherein:
U is $-NH-$;
Z is CH;
$R^2$ is cyclopentyl;
$R^3$ is $C(O)CH_3$; and
$R^4$ is $CH_3$.

5. The compound of claim 1, or a pharmaceutically acceptable salt, hydrate, or stereoisomer thereof, wherein:
(i) A is Formula (II):

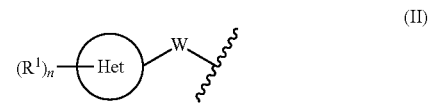

wherein:

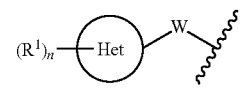

is:

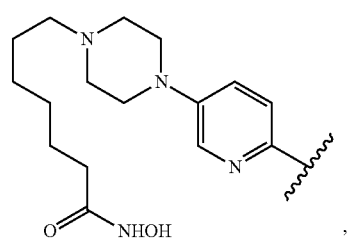

,

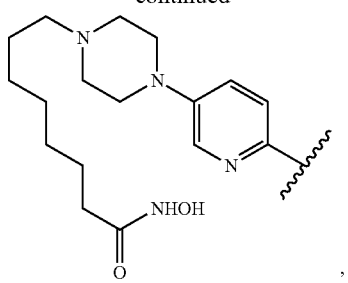
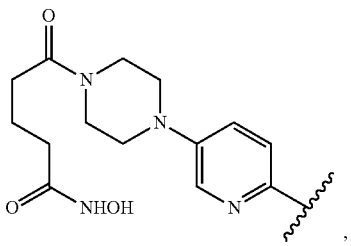
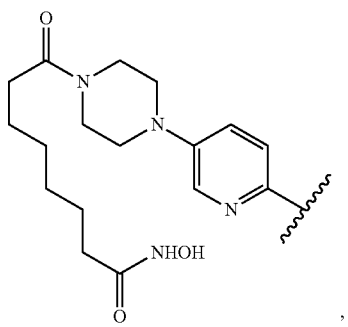
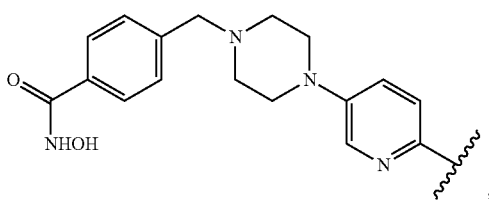
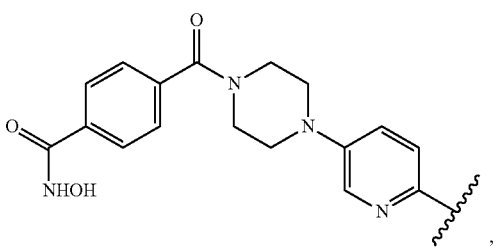
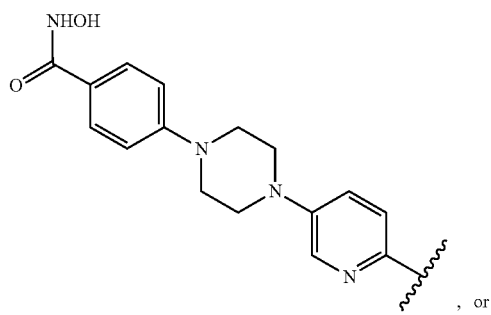, or
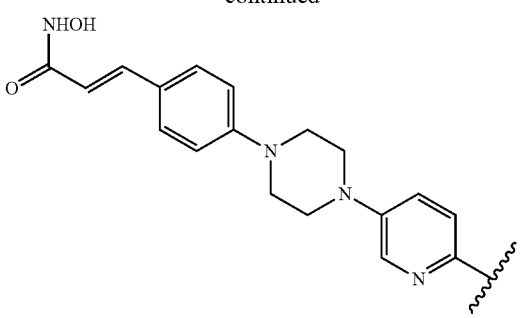
wherein:
⌇⌇⌇ is the point of attachment to U; or
(ii) A is Formula (III):
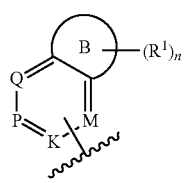
wherein:
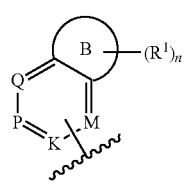
is:
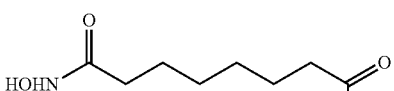 or -continued

[Structure: benzamide with NHOH, CH2-linked to tetrahydronaphthyridine]

wherein:
⁓ is the point of attachment to U; or (iii) A is Formula (V):

$$(R^1)_n\text{—}W\text{—}\sim$$  (V)

wherein:

$$(R^1)_n\text{—}W\text{—}\sim$$

is:

[Structure: HOHN-C(O)-(CH2)5-NH-C(O)-pyridine]

wherein:
⁓ is the point of attachment to U.

6. The compound of claim 1, or a pharmaceutically acceptable salt, hydrate, or stereoisomer thereof, wherein:

A is Formula (II):

$$(R^1)_n\text{—}\boxed{\text{Het}}\text{—}W\text{—}\sim$$  (II)

wherein:

$$(R^1)_n\text{—}\boxed{\text{Het}}\text{—}W\text{—}\sim$$

is

-continued

[Structure: R1-N-piperazine-N-phenyl]

$R^1$ is $(CH_2)_p\text{—}V\text{—}(CH_2)_q\text{—}C(O)NHOH$; and

⁓ the point of attachment to U.

7. The compound of claim 6, or a pharmaceutically acceptable salt, hydrate, or stereoisomer thereof, wherein:

V is $\text{—}CH_2\text{—}$, $\text{—}C(O)\text{—}$, $\text{—}C(O)NH\text{—}$, $C_{6-12}$ arylene, 5- to 15-membered heteroarylene, or $\text{—}V^1\text{—}(CH_2)_t\text{—}V^2\text{—}$;

$V^1$ is $\text{—}CH\text{=}CH\text{—}$, $C_{6-12}$ arylene, or 5- to 15-membered heteroarylene;

$V^2$ is $\text{—}CH\text{=}CH\text{—}$, $C_{6-12}$ arylene, or 5- to 15-membered heteroarylene;

p is 0, 1, 2, 3, 4, 5, or 6;

q is 0, 1, 2, 3, 4, 5, or 6; and t is 0, 1, or 2.

8. The compound of claim 1, or a pharmaceutically acceptable salt, hydrate, or stereoisomer thereof, wherein:

A is Formula (V):

$$(R^1)_n\text{—}W\text{—}\sim$$  (V)

wherein:

$R^1$ is $(CH_2)_p\text{—}V\text{—}(CH_2)_q\text{—}C(O)NHOH$;

n is 1; and

⁓ is the point of attachment to U.

9. The compound of claim 1, or a pharmaceutically acceptable salt, hydrate, or stereoisomer thereof, wherein:

A is Formula (V):

$$(R^1)_n\text{—}W\text{—}\sim$$  (V)

wherein:

$R^1$ is $(CH_2)_p\text{—}V\text{—}(CH_2)_q\text{—}C(O)NHOH$;

V is $\text{—}CH_2\text{—}$, $\text{—}C(O)\text{—}$, $\text{—}C(O)NH\text{—}$, $C_{6-12}$ arylene, or $\text{—}V^1\text{—}(CH_2)_t\text{—}V^2\text{—}$;

$V^1$ is $\text{—}CH\text{=}CH\text{—}$, $C_{6-12}$ arylene, or 5- to 15-membered heteroarylene;

$V^2$ is $\text{—}CH\text{=}CH\text{—}$, $C_{6-12}$ arylene, or 5- to 15-membered heteroarylene;

n is 1;

p is 0, 1, 2, 3, 4, 5, 6, or 7;

q is 0, 1, 2, 3, 4, 5, 6, or 7;

t is 0, 1, or 2; and

⁓ is the point of attachment to U.

10. The compound of claim 4, or a pharmaceutically acceptable salt, hydrate, or stereoisomer thereof, wherein:

A is Formula (II):

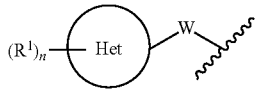

(II)

wherein:

Het is a monocyclic 4- to 8-membered heterocyclyl, a bicyclic 9- to 15-membered bridged heterocyclyl, or a bicyclic 9- to 15-membered spirocyclic heterocyclyl, wherein the monocyclic 4- to 8-membered heterocyclyl, the bicyclic 9- to 15-membered bridged heterocyclyl, or the bicyclic 9- to 15-membered spirocyclic heterocyclyl contains 1, 2, 3, or 4 heteroatoms independently selected from the group consisting of nitrogen and oxygen;

$R^1$ is $(CH_2)_p$—V—$(CH_2)_q$—C(O)NHOH; and n is 1.

11. The compound of claim 4, or a pharmaceutically acceptable salt, hydrate, or stereoisomer thereof, wherein:

A is Formula (III):

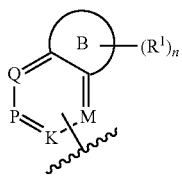

(III)

wherein:

B is a non-aromatic, monocyclic 5- to 12-membered heterocyclyl, wherein the 5- to 12-membered heterocyclyl contains 1, 2, 3, or 4 heteroatoms independently selected from the group consisting of nitrogen and oxygen;

$R^1$ is $(CH_2)_p$—V—$(CH_2)_q$—C(O)NHOH;

n is 1; and

〰 is the point of attachment to U.

12. The compound of claim 4, or a pharmaceutically acceptable salt, hydrate, or stereoisomer thereof, wherein:

A is Formula (III):

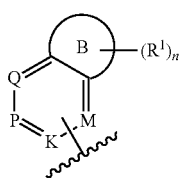

(III)

wherein:

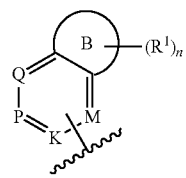

is:

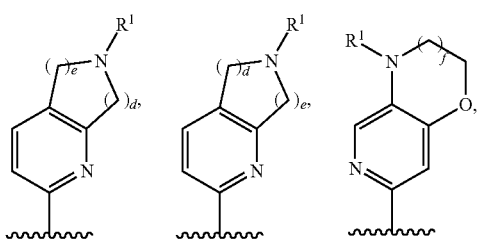

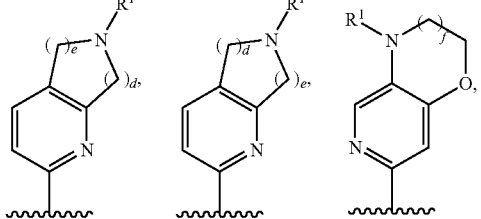

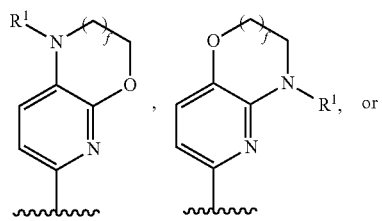

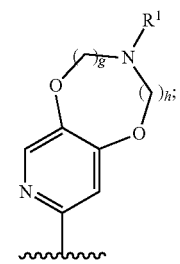

$R^1$ is $(CH_2)_p$—V—$(CH_2)_q$—C(O)NHOH;

d is 0, 1, 2, or 3;

e is 0, 1, 2, or 3;

f is 1, 2, or 3;

g is 2, 3, or 4;

h is 2, 3, or 4; and

〰 is the point of attachment to U;

with the proviso that the sum of d and e is equal to or greater than 2.

13. A pharmaceutical composition comprising a pharmaceutically acceptable carrier or excipient and the compound of claim 1, or a pharmaceutically acceptable salt, hydrate, or stereoisomer thereof.

14. A compound selected from the group consisting of:
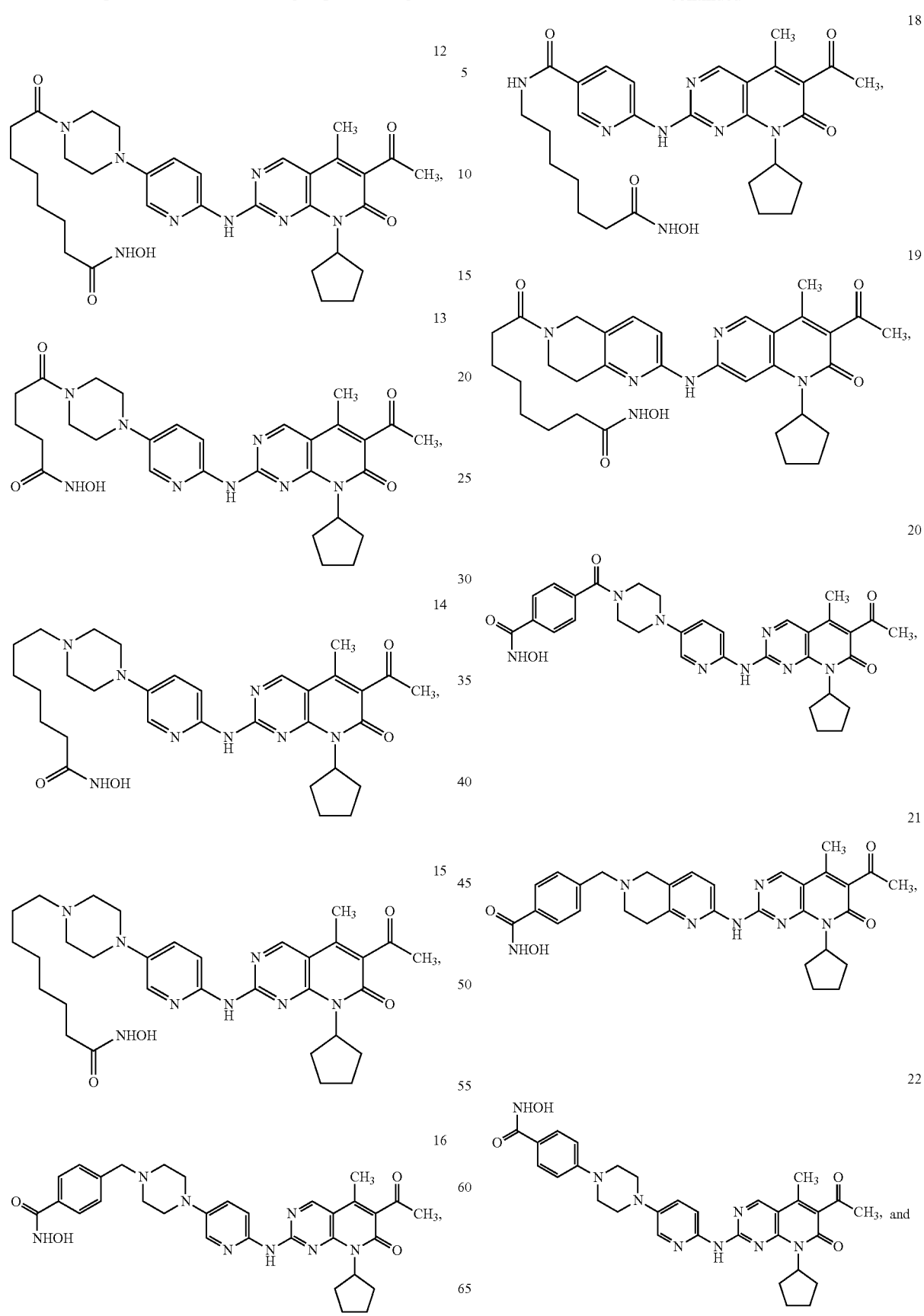
and

23
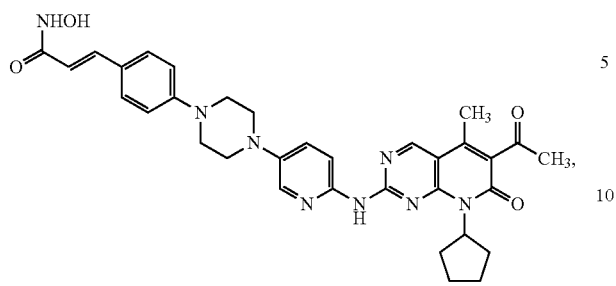
or a pharmaceutically acceptable salt or hydrate thereof.
* * * * *